United States Patent [19]
Swartz

[11] Patent Number: 5,633,165
[45] Date of Patent: May 27, 1997

[54] FERMENTOR WITH VERTICAL SHAFT

[75] Inventor: James R. Swartz, Menlo Park, Calif.

[73] Assignee: Genentech, Inc., South San Francisco, Calif.

[21] Appl. No.: 451,241

[22] Filed: May 25, 1995

Related U.S. Application Data

[62] Division of Ser. No. 240,121, May 9, 1994, Pat. No. 5,487,980, which is a division of Ser. No. 989,844, Nov. 23, 1992, Pat. No. 5,342,763.

[51] Int. Cl.$^6$ .................................................. C12M 1/06
[52] U.S. Cl. ..................... 435/287.1; 435/287.5; 435/289.1; 435/286.7
[58] Field of Search ........................... 435/286.1, 286.5, 435/286.6, 286.7, 287.1, 287.5, 289.1, 302.1

[56] References Cited

U.S. PATENT DOCUMENTS

| | | | |
|---|---|---|---|
| 3,384,553 | 5/1968 | Caslavsky et al. | 435/289.1 |
| 3,445,341 | 5/1969 | Freedman et al. | 435/289.1 |
| 3,445,342 | 5/1969 | Freedman | 435/289.1 |
| 4,064,015 | 12/1977 | Nyiri et al. | 435/289.1 |
| 4,116,778 | 9/1978 | Belousov et al. | 195/139 |
| 4,476,224 | 10/1984 | Adler . | |
| 4,762,784 | 8/1988 | Keith et al. . | |
| 4,882,283 | 11/1989 | Gentry | 435/289.1 |
| 5,049,493 | 9/1991 | Khosla et al. . | |
| 5,182,195 | 1/1993 | Nakahama et al. . | |
| 5,342,763 | 8/1994 | Swartz | 435/69.1 |
| 5,487,980 | 1/1996 | Swartz | 435/29 |

OTHER PUBLICATIONS

Dahod. "Redox Potential as a Better Substitute for Dissolved Oxygen in Fermentation Process Control." Biotechnology and Bioengineering. vol. 24 (1982), pp. 2123–2125. 1982.

Memmert et al. "Continuous Production of Bacillus Exoenzymes through Redox-Regulation." Annals NY Academy of Sciences. vol. 506 (1987). pp. 631–636. 1987.

Shibai et al. "Simultaneous Measurement of Dissolved Oxygen and Oxidation-Reduction Potentials in the Aerobic Culture." Agr. Biol. Chem. vol. 38 (1974), pp. 2407–2411. 1974.

Anaraku and Gennis, "The Aerobic Respiratory Chain of *Escherichia coli*" TIBS 12:262–266 (Jul. 1987).

Andersson and Roth, "Redox Regulation of the Genes for Cobinamide Biosynthesis in *Salmonella typhimurium*" J. Bacteriology 171(12):6734–6739 (Dec. 1989).

Au et al., "Isolation and Characterization of an *Escherchia coli* Mutant Lacking the Cytochrome o Terminal Oxidase" J. Bacteriology 161(1):123–127 (1985).

Au et al., "Role Quinones in the Branch of the *Escherichia coli* Respiratory Chain that Terminates in Cytochrome o" J. Bacteriology 157(1):122–125 (1984).

Bi-Yan and Kwan, "Aminoglycoside-Resistant Mutants of *Pseudomonas aeruginosa* Deficient in Cytochrome d, Nitrite Reductase, and Aerobic Transport" Antimicrobial Agents and Chemotherapy 19(6):958–964 (Jun. 1981).

Brock et al. *Biology of Microorganisms*, NJ:Prentice Hall p. 673 (1988).

Castor et al., "Photochemical Determinations of the Oxidase of Bacteria" Journal of Biological Chemistry 234:1587–1592 (1959).

Center for Drugs and Biologics et al. *Guideline on General Principles of Process Validation* (May 1987).

(List continued on next page.)

Primary Examiner—William H. Beisner
Attorney, Agent, or Firm—Janet E. Hasak

[57] ABSTRACT

A process for producing a polypeptide of interest from fermentation of bacterial host cells comprising nucleic acid encoding the polypeptide is provided. In this method, the host cells employed have an inactivated electron transport chain. Further provided is a method for determining if a particular bacterial cell culture has a propensity for dissolved oxygen instability when fermented on a large scale.

2 Claims, 38 Drawing Sheets

OTHER PUBLICATIONS

Chepuri et al., "Recent Studies of the Cytochrome o Terminal Oxidase Complex of *Escherichia coli*" *Biochimica et Biophysica Acta* 1018:124–127 (1990).

Cotter et al., "Cytochrome o (cyoABCDE) and d (cydAB) oxidase gene expression in *Escherichia coli* is regulated by oxygen, pH, and the fnr gene product" *J. Bacteriol.* 172(11):6333–6338 (1990).

Daldal, F., "Cytochrome $c_2$-Independent Respiratory Growth of *Rhodobacter capsulatus*" *J. Bacteriology* 170(5):2388–2391 (1988).

Dassa et al., "A New Oxygen-Regulated Operon in *Escherichia coli* Comprises the Genes for a Putative Third Cytochrome Oxidase and for pH 2.5 Acid Phosphatase (appA)" *Mol. Gen. Genet.* 229:341–352 (1991).

Degn and Harrison, "Theory of Oscillations of Respiration Rate in Continuous Culture of *Klebsiella aerogenes*" *J. Theoret. Biol.* 22:238–248 (1969).

Denis et al., "Oxygen Regulation of Nitrate Transport by Diversion of Electron Flow in *Escherichia coli*" *J. Biological Chem.* 265(30):18095–18097 (1990).

Deutch, "Association of the PutA Protein with the Cell Membrane in *Escherichia coli* Requires Components of the Aerobic Electron Transport Chain" *92nd Gen. Mtg. of the American Society for Microbiology, May 26–30* (Ab. #K-97) p. 272 (1992).

Dikshit, "The Bacterial Hemoglobin from *Vitreoscilla* Can Support the Aerobic Growth of *Escherichia coli* Lacking Terminal Oxidases" *Arch. Biochem. and Biophys.* 293(2):241–245 (1992).

Doelle and Hollywood, "Transitional Steady-State Investigations during Aerobic-Anaerobic Transition of Glucose Utilization by *Escherichia coli* K-12" *European Journal of Biochemistry* 83:479–484 (1978).

Edwards et al., "Photochemical Action Spectra of Bacterial a- and o-Type Oxidases Using A Dye Laser" *FEBS Letters* 128(2):205–207 (1981).

Fang et al., "Location of Heme Axial Ligands in the Cytochrome d Terminal Oxidase Complex of *Escherichia coli* Determined by Site-directed Mutagenesis" *J. Biological Chem.* 264(14):8026–8032 (1989).

Fu et al., "The Requirement of ArcA and Fnr for Peak Expression of the cyd Operon in *Escherichia coli* Under Microaerobic Conditions" *Mol. Gen. Genet.* 226:209–213 (1991).

Georgiou et al., "Identification of the cydC Locus Required for Expression of the Functional Form of the Cytochrome d Terminal Oxidase Complex in *Escherichia coli*" *J. Bacteriology* 169(5):2107–2112 (1987).

Green and Gennis, "Biochemical and Genetic Characterization of an *Escherichia coli* Mutant Lacking Cytochrome d" *Fed. Proc.* (Ab. #3652) 41 (1982).

Green and Gennis, "Isolation and Characterization of an *Escherichia coli* Mutant Lacking Cytochrome d Terminal Oxidase" *J. Bacteriology* 154(3):1269–1275 (1983).

Green et al., "Identification of Subunit I as the Cytochrome $b_{558}$ Component of the Cytochrome d Terminal Oxidase Complex of *Escherichia coli*" *J. Biological Chem.* 259(12):7994–7997 (1984).

Green et al., "Isolation and Characterization of an *Escherichia coli* Mutant Lacking Cytochrome d" *Fed. Proc. (Ab. #749) 40:1669 (1981)*.

Green et al., "The Nucleotide Sequence of the cyd Locus Encoding the Two Subunits of The Cytochrome d Terminal Oxidase Complex of *Escherichia coli*" *J. Biological Chem.* 263(26):13138–13143 (1988).

Haddock and Schairer, "Electron-Transport Chains of *Escherichia coli*" *European Journal of Biochemistry* 35:34–45 (1973).

Haltia et al., "Deletion of the Gene for Subunit III Leads to Defective Assembly of Bacterial Cytochrome Oxidase" *The EMBO Journal* 8(12):3571–3579 (1989).

Harrison and Loveless, "The Effect of Growth Conditions on Respiratory Activity and Growth Efficiency in Facultative Anaerobes Grown in Chemostat Culture" *J. Gen. Microbiology* 68:35–43 (1971).

Harrison and Pirt, "The Influence of Dissolved Oxygen Concentration on the Respiration and Glucose Metabolism of *Klebsiella aerogenes* during Growth" *J. Gen. Microbiol.* 46:193–211 (1967).

Hashimoto and Hino, "Isolation of the Mutants of *Escherichia coli* that are Defective in Some Respiratory Enzymes" *J. Science of the Hiroshima University* 15:103–113 (1975).

Hoffman et al., "Respiratory-Chain Characteristics of Mutants of *Azotobacter vinelandii* Negative to Tetramethyl-p-phenylenediamine Oxidase" *European Journal of Biochemistry* 100:19–27 (1979).

Hoffman et al., "Studies of Photochemical Action Spectra on N,N,N',N'-Tetramethyl-p-phenylenediamine-Oxidase-Negative Mutants of *Azotobacter vinelandii*" *European Journal of Biochemistry* 105:177–185 (1980).

Hopkins et al., "Effects of Dissolved Oxygen Shock on the Stability of Recombinant *Escherichia coli* Containing Plasmid pKN401" *Biotechnology and Bioengineering* 29:85–91 (1987).

Iuchi et al, "Requirement for Terminal Cytochromes in Generation of the Aerobic Signal for the arc Regulatory System in *Escherichia coli*: Study Utilizing Deletions and lac Fusions of cyo and cyd" *J. Bacteriology* 172(10):6020–6025 (1990).

James et al., "The Cytochrome Oxidases of *Bacillus subtilis*: Mapping of a Gene Affecting Cytochrome $aa_3$ and its Replacement by Cytochrome o in a Mutant Strain" *FEMS Microbiol. Letters* 58:277–282.

Kelly et al., "Cloning and Mutagenesis of Genes Encoding the Cytochrome bd Terminal Oxidase Complex in *Azotobacter vinelandii*: Mutants Deficient in the Cytochrome d Complex are Unable to Fix Nitrogen in Air" *J. Bacteriology* 172(10):6010–6019 (1990).

Kranz and Gennis, "Immunological Investigation of the Distribution of Cytochromes Related to the Two Terminal Oxidases of *Escherichia coli* in Other Gram-Negative Bacteria" *J. Bacteriology* 161(2):709–713 (1985).

Kranz et al., "Immunological Characterization of an *Escherichia coli* Strain Which is Lacking Cytochrome d" *J. Bacteriology* 156(1):115–121 (1983).

Kwong et al., "On-Line Assessment of Metabolic Activities Based on Culture Redox Potential and Dissolved Oxygen Profiles During Aerobic Fermentation" *Biotechnol. Prog.* 8:576–579 (1992).

Laszlo et al., "Cytochrome o as a Terminal Oxidase and Receptor for Aerotaxis in *Salmonella typhimurium*" *J. Bacteriology* 159(2):663–667 (1984).

Lemieux et al., "Determination of the Ligands of the Low Spin Heme of the Cytochrome o Ubiquinol Oxidase Complex Using Site-directed Mutagenesis" *J. Biological Chem.* 267(3):2105–2113 (1992).

Li et al., "Effect of the Levels of Dissolved Oxygen on the Expression of Recombinant Proteins in Four Recombinant *Escherichia coli* Strains" *J. Industrial Microbiol.* 9:1–10 (1992).

Lin and Swartz, "Production of Heterologous Proteins from Recombinant DNA *Escherichia coli* in Bench Fermentors" *Methods: A Companion to Methods in Enzymology* 4:159–168 (1992).

Lorence et al., "Potentiometric Analysis of the Cytochromes of an *Escherichia coli* Mutant Strain Lacking the Cytochrome d Terminal Oxidase Complex" *J. Bacteriology* 157(1):115–121 (1984).

Matsushita and Kaback, "D-Lactate Oxidation and Generation of the Proton Electrochemical Gradient in Membrane Vesicles from *Escherichia coli* GR19N and in Proteoliposomes Reconstituted with Purified $_D$-Lactate Dehydrogenase and Cytochrome o Oxidase" *Biochemistry* 25:2321–2327 (1986).

Matsushita et al., "Reconstitution of Active Transport in Proteoliposomes Containing Cytochrome o Oxidase and lac Carrier Protein Purified from *Escherichia coli*" *Proc. Natl. Acad. Sci. USA* 80:4889–4893 (1983).

McInerney et al., "Respiratory Mutants of *Azotobacter vinelandii* with Elevated Levels of cytochrome d" *European Journal of Biochemistry* 141:447–452 (1984).

Minagawa et al., "Identification of Heme and Copper Ligands in Subunit I of the Cytochrome bo Complex in *Escherichia coli*" *J. Biological Chem.* 267(3):2096–2104 (1992).

Mogi et al., "Exploring Molecular Mechanism of Redox-Coupled Proton Pumping by Terminal Oxidases: Site-directed Mutagenesis Studies on Subunit I of the *E. coli* Cytochrome Bo Complex" *Biophys. J.* (Ab. #1631) 61:A284 (1992).

O'Brian and Maier, "Expression of Cytochrome o in Hydrogen Uptake Constitutive Mutants of *Rhizobium japonicum*" *J. Bacteriology* 161(2):507–514 (1985).

Oden and Gennis, "Isolation and Characterization of a Cytochrome d Terminal Oxidase Mutant from *Escherichia coli*" *Journal of Cell Biology* (Ab. #3540) 107:624A (1988).

Oden and Gennis, "Isolation and Characterization of a New Class of Cytochrome d Terminal Oxidase Mutants of *Escherichia coli*" *J. Bacteriology* 173(19):6174–6183 (1991).

Oden et al., "Genomic Replacement in *Escherichia coli* K-12 Using Covalently Closed Circular Plasmid DNA" *Gene.* 96:29–36 (1990).

Poole and Ingledew, "Pathways of Electrons to Oxygen" *Escherichia coli and Salmonella typhimurium: Cellular and Molecular Biology*, Neidhardt et al., eds., American Society for Microbiology vol. 1:170–200 (1987).

Poole and Williams, "Formation of the 680 nm-Absorbing Form of the Cytochrome bd Oxidase Complex of *Escherichia coli* by Reaction of Hydrogen Peroxide with the Ferric Form" *FEBS Letters* 231(1):243–246 (Apr. 1988).

Poole et al., "Bacterial Cytochrome Oxidases: A Structurally and Functionally Diverse Group of Electron-Transfer Proteins" *Biochimica et Biophysica Acta* 726:205–243 (1983).

Poole et al., "Microbial Metabolism of Oxygen: The Binding and Reduction of Oxygen by Bacterial Cytochrome Oxidases" *Microbial Gas Metabolism*, Poole and Dow, eds., Academic Press, Chapter Two, pp. 31–62 (1985).

Poole et al., "Mutations Affecting the Cytochrome d-Containing Oxidase Complex of *Escherichia coli* K12: Identification and Mapping of a Fourth Locus, cydD" *J. Gen. Microbiol.* 135:1865–1874 (1989).

Puustinen et al., "Cytochrome o (bo) is a Proton Pump in *Paracoccus denitrificans* and *Escherichia coli*" *FEBS Letters* 249(2):163–167 (Jun. 1989).

Puustinen et al., "Properties of the Two Terminal Oxidases of *Escherichia coli*" *Biochemistry* 30:3936–3942 (1991).

Sasarman, "Donnees Preliminaires Sur Un Mutant Cytochrome d Deficient de *Salmonella typhimurium* LT2" *Rev. Can. Biol.* 31(4):317–319 (1972).

Sharma et al., "Cytochrome Pattern of Effective Rhizobium Strains of Cowpea Misc. and Their Ineffective Mutants" *Indian J. of Microbiology* 27(1–4):26–31 (1987).

Shioi et al., "Signal Transduction in Chemotaxis to Oxygen in *Escherichia coli* and *Salmonella typhimurium*" *J. Bacteriology* 170(12):5507–5511 (1988).

Soberon et al., "Isolation of a *Rhizobium phaseoli* Cytochrome Mutant with Enhanced Respiration and Symbiotic Nitrogen Fixation" *J. Bacteriology* 171(1):465–472 (1989).

Soberon et al., "Isolation of *Rhizobium phaseoli* Tn5-Induced Mutants with Altered Expression of Cytochrome Terminal Oxidases o and aa3" *J. Bacteriology* 172(3):1676–1680 (1990).

Swartz, J., "Scale-up of Genetically Engineered Products" *World Biotech Reporter* 2:367–379 (1984).

Tamura-Lis and Webster, "Cyanide- and Carbon Monoxide-Resistant Mutants of Vitreoscilla: Altered Cytochromes and Respiratory Properties" *Arch. Biochem. and Biophys.* 244(1):285–291 (1986).

Tamura-Lis and Webster, "Respiration in Carbon Monoxide and Cyanide Resistant Strains of Vittreoscilla" *Fed. Proc.* (Ab. #2799) 41(3):749 (1982).

Terriere et al., "Hydroxylation of 2-Octaprenylphenol in *Escherichia coli* K12" *Biochem. and Biophys. Res. Comm.* 111(3):830–839 (1983).

Tron and Lemesle-Meunier, "Two Substitutions at the Same Position in the Mitochondrial Cytochrome b Gene of *S. cerevisiae* Induce a Mitochondrial Myxothiazol Resistance and Impair the Respiratory Growth of the Mutated Strains Albeit Maintaining a Good Electron Transfer Activity" *Current Genetics* 18:413–419 (1990).

van der Oost et al., "Restoration of a Lost Metal-Binding Site: Construction of Two Different Copper Sites into a Subunit of the *E. coli* Cytochrome o Quinol Oxidase Complex" *The EMBO Journal* 11(9):3209–3217 (1992).

Wallace and Young, "Role of Quinones in Electron Transport to Oxygen and Nitrate in *Escherichia coli*" *Biochimica et Biophysica Acta* 461:84–100 (1977).

Webster et al., "Cytochromes O and D in Wild Type and Mutant Vitreoscilla" *Fed. Proc.* (Abst. #1564) 44(3):678 (1985).

Williams et al., "Functional Size Measurements of the Ubiquinol Oxidase Activity of the Cytochrome o Terminal Oxidase Complex of *Escherichia coli*" *Biochemical Journal* 276:555–557 (1991).

Willison and Haddock, 37 The Efficiency of Energy Conservation in Cytochrome c-Deficient Mutants of *Paracoccus denitrificans*" *FEMS Microbiol. Letters* 10:53–57 (1981).

Willison and John, "Mutants of *Paracoccus dentrificans* Deficient in c-type Cytochromes" *J. Gen. Microbiol.* 115:443–450 (1979).

Willison et al., "A Mutant of *Paracoccus denitrificans* Deficient in Cytochrome a + a3" *FEMS Microbiol. Letters* 10:249–255 (1981).

Wu et al., "Isolation and Characterization of *Escherichia coli* Mutants Affected in Aerobic Respiration: The Cloning and Nucleotide Sequence of ubiG" *J. Gen. Microbiol.* 138:2101–2112 (1992).

Yang, T., "Isolation and Characterization of TMPD-Oxidase Mutants of *Pseudomonas aeruginosa*" *Arch. Microbiol.* 144:228–232 (1986).

Yegneswaran et al., "Experimental Simulation of Dissolved Oxygen Fluctuations in Large Fermentors: Effect on *Streptomyces clavuligerus*" *Biotech. and Bioeng.* 38:1203–1209 (1991).

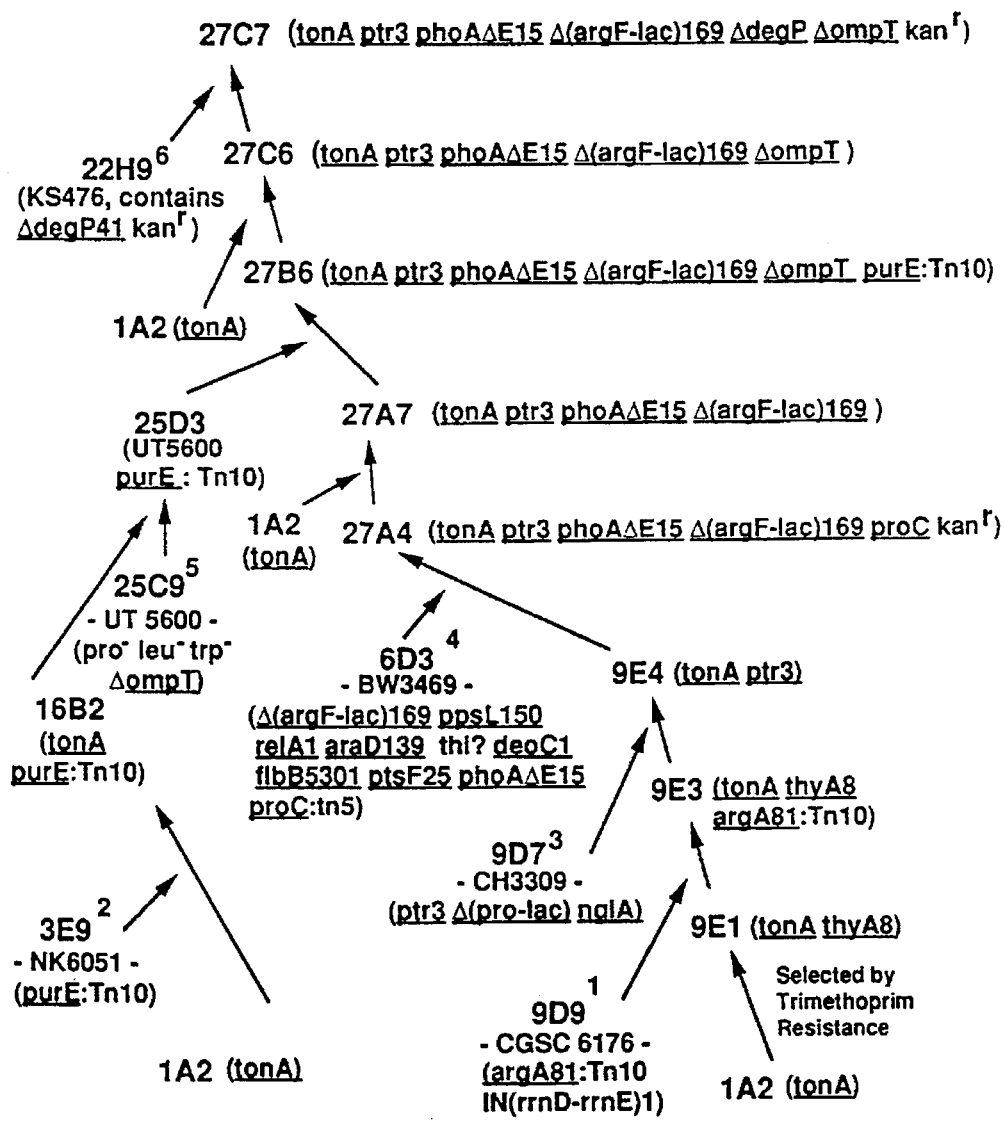

FIG.2

Lineage of E.coli W3110 Strain 27C7

27C7 (tonA ptr3 phoAΔE15 Δ(argF-lac)169 ΔdegP ΔompT kan^r)

22H9^6 27C6 (tonA ptr3 phoAΔE15 Δ(argF-lac)169 ΔompT)
(KS476, contains ΔdegP41 kan^r)

27B6 (tonA ptr3 phoAΔE15 Δ(argF-lac)169 ΔompT purE:Tn10)

1A2 (tonA)

25D3         27A7 (tonA ptr3 phoAΔE15 Δ(argF-lac)169)
(UT5600
purE:Tn10)

1A2      27A4 (tonA ptr3 phoAΔE15 Δ(argF-lac)169 proC kan^r)
25C9^5      (tonA)
- UT 5600 -
(pro⁻ leu⁻ trp⁻      6D3^4
ΔompT)              - BW3469 -        9E4 (tonA ptr3)
16B2               (Δ(argF-lac)169 ppsL150
(tonA              relA1 araD139 thi? deoC1
purE:Tn10)         flbB5301 ptsF25 phoAΔE15
                   proC:tn5)
                                      9E3 (tonA thyA8
                   9D7^3                  argA81:Tn10)
3E9^2             - CH3309 -
- NK6051 -        (ptr3 Δ(pro-lac) nglA)
(purE:Tn10)                           9E1 (tonA thyA8)
                                          Selected by
                          9D9^1           Trimethoprim
                        - CGSC 6176 -     Resistance
          1A2 (tonA)    (argA81:Tn10
                        IN(rrnD-rrnE)1)  1A2 (tonA)

1. Obtained from B. Bachman, E.coli Genetic Stock Center
2. From Dr. Nancy Kleckner's Laboratory, similar strain available from Dr. Carol Gros, University of Wisconsin
3. J.Bact. 140, 1979, p. 125.
4. Obtained from Professor Barry Wanner, Purdue University.
5. J.Bact. 153, 1983, p. 1104-1106.
6. Obtained from Harvard Medical School, Office of Technology Licensing and Industry-Sponsored Research.

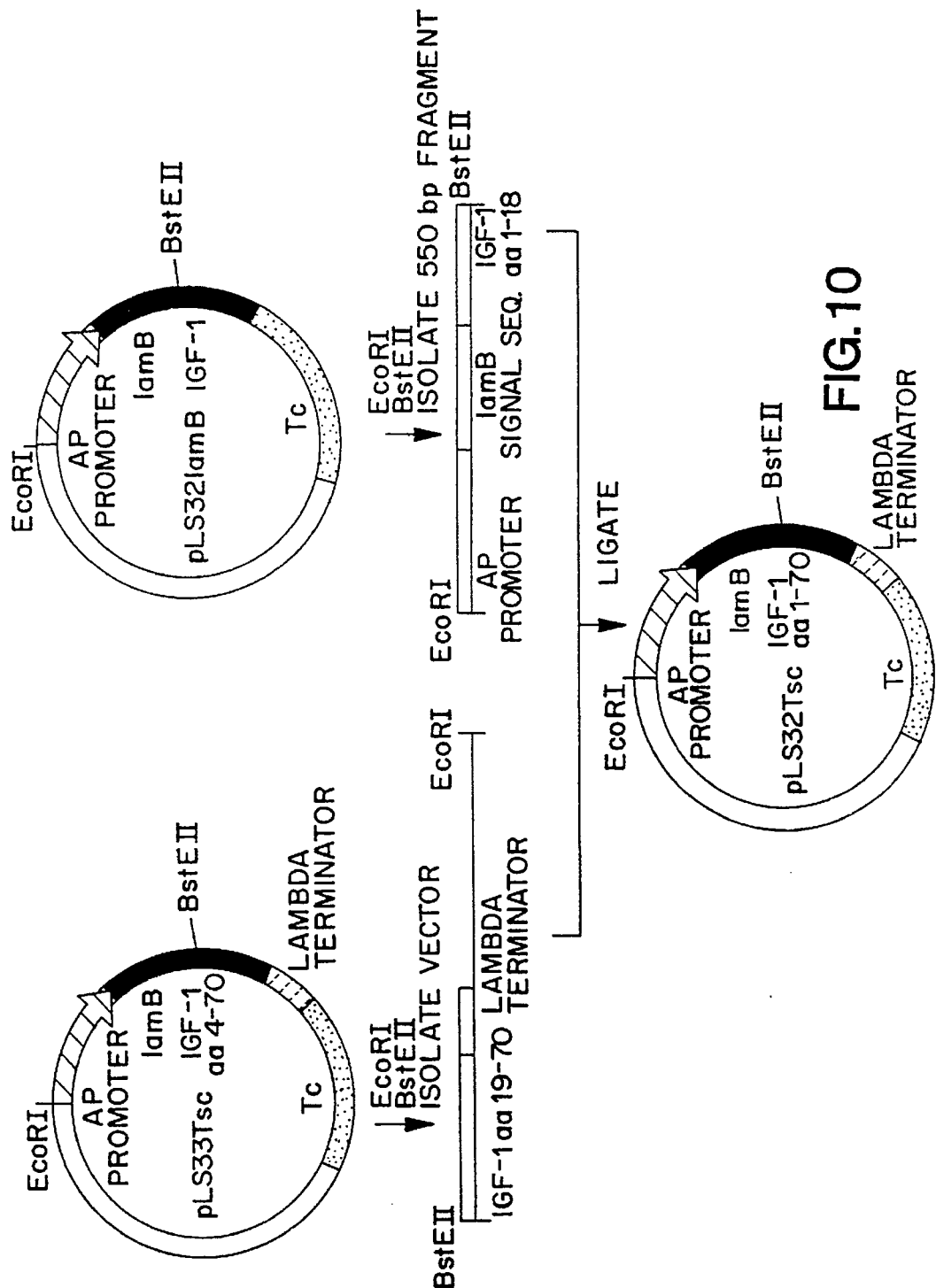

```
GAATTCAACT TCTCCATACT TTGGATAAGG AAATACAGAC ATGAAAAATC    50

TCATTGCTGA GTTGTTATTT AAGCTTGCCC AAAAAGAAGA AGAGTCGAAT   100

GAACTGTGTG CGCAGGTAGA AGCTTTGGAG ATTATCGTCA CTGCAATGCT   150

TCGCAATATG GCGCAAAAATG ACCAACAGCG GTTGATTGAT CAGGTAGAGG  200

GGGCGCTGTA CGAGGTAAAG CCCGATGCCA GCATTCCTGA CGACGATACG   250

GAGCTGCTGC GCGATTACGT AAAGAAGTTA TTGAAGCATC CTCGTCAGTA   300

AAAAGTTAAT CTTTTCAACA GCTGTCATAA AGTTGTCACG GCCGAGACTT   350

ATAGTCGCTT TGTTTTTATT TTTAAATGTA TTTGTAACTA GTACGCAAGT   400
```

FIG.11A

```
TCACGTAAAA AGGGTATCTA GAATTATG ATG ATT ACT CTG CGC  443
                                Met Ile Thr Leu Arg
                                -24              -20

AAA CTT CCT CTG GCG GTT GCC GTC GCA GCG GGC GTA ATG  482
Lys Leu Pro Leu Ala Val Ala Val Ala Ala Gly Val Met
                                              -10

TCT GCT CAG GCC ATG GCC GGT CCC GAA ACT CTG TGC GGT  521
Ser Ala Gln Ala Met Ala Gly Pro Glu Thr Leu Cys Gly
                         1

GCT GAA CTG GTT GAC GCT CTG CAG TTT GTT TGC GGT GAC  560
Ala Glu Leu Val Asp Ala Leu Gln Phe Val Cys Gly Asp
             10                                  20

CGT GGT TTT TAT TTT AAC AAA CCC ACT GGT TAT GGT TCT  599
Arg Gly Phe Tyr Phe Asn Lys Pro Thr Gly Tyr Gly Ser
                         30
```

FIG.11B

```
TCT TCT CGT CGT GCT CCC CAG ACT GGT ATT GTT GAC GAA  638
Ser Ser Arg Arg Ala Pro Gln Thr Gly Ile Val Asp Glu
                        40

TGC TGC TTT CGT TCT TGC GAC CTG CGT CGT CTG GAA ATG  677
Cys Cys Phe Arg Ser Cys Asp Leu Arg Arg Leu Glu Met
            50

TAT TGC GCT CCC CTG AAA CCC GCT AAA TCT GCT TAG AAGCTC  719
Tyr Cys Ala Pro Leu Lys Pro Ala Lys Ser Ala AM*
 60                                       70

CTAACGCTCGG TTGCCGCCGG GCGTTTTTA TTGTTAA  757

Position Number -24 signifies the start of the lamB signal sequence.
Position NUmber   1 signifies the start of the IGF-I protein.
```

FIG.11C

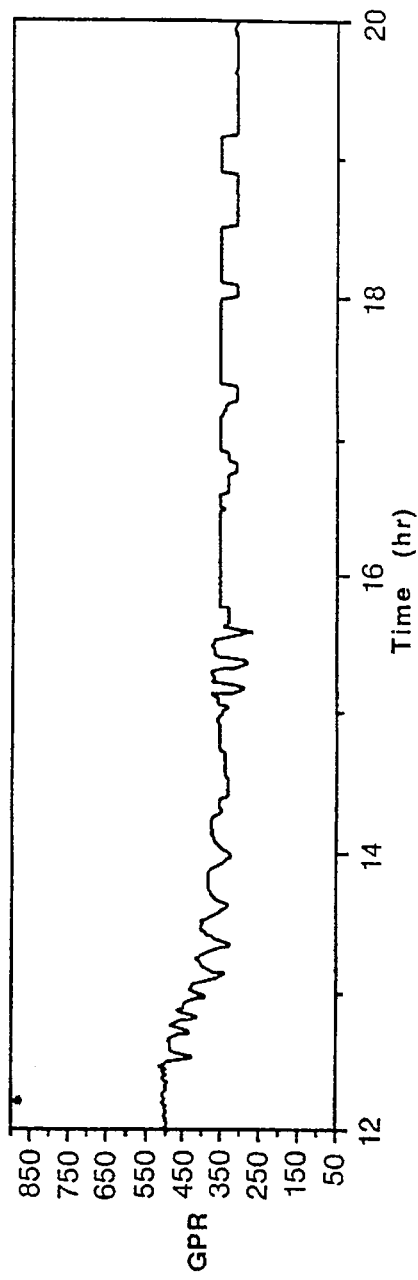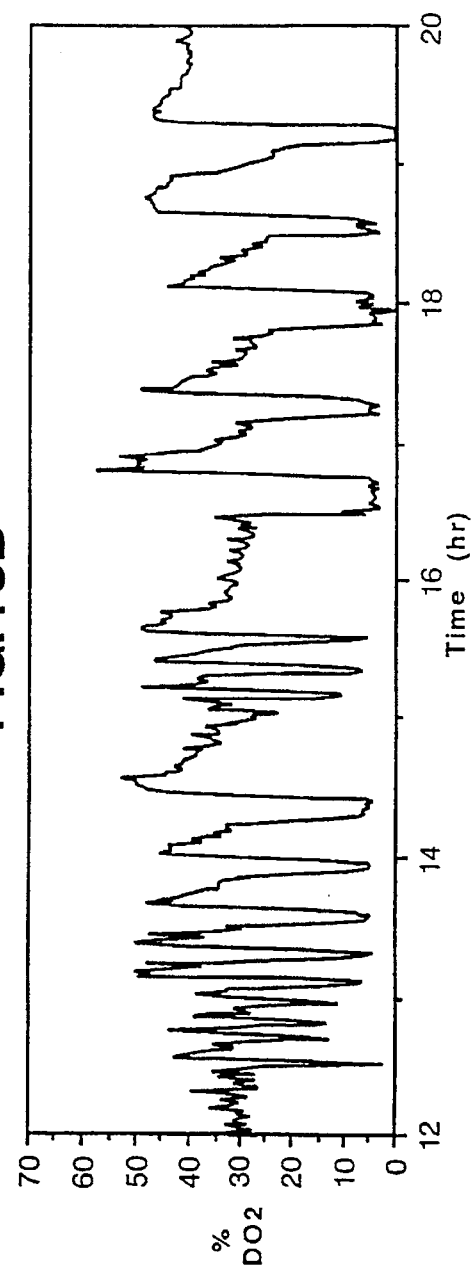

FIG. 18

EcoRI (1149)
5'-GAATTCATGAGATTTCCTTCAATTTTTACTGCAGTTTTATTCGCAGCATCCTCCGCATTAGC

TGCTCCAGTCAACACTACAACAGAAGATGAAACGGCACACAAATTCCGGCTGAAGCTGTCATCGGTT

ACTTAGAGATTTAGAAGGGGATTTCGATGTTGCTGTTTGCCATTTTCCAACAGCACAAATAACGGG

TTATTGTTTATAAATACTACTATTGCCAGCATTGCTGCTAAAGAAGAAGGGTATCTTTGGATAA

HaeII                  PstI
AAGAGGTCCGGAAACTCTGTGCGGCGCTGAGCTGGTTGACGCTCTGCAGTTCGTATGTGGTGATC

BamHI
GAGGCTTCTACTTCAACAAACCGACTGGGTACGGATCCTCCTCTCGTGCTCCGCAAACCGGC

ATCGTTGATGAATGCTGTTTTCGGTCCTGTGACCTTCGCCGTCTGAAAATGTACTGCGCTCCGCT

SalI   EcoRI (1633)
GAAACCGGCTAAGTCTGCATAGTCTGACGAATTC-3'

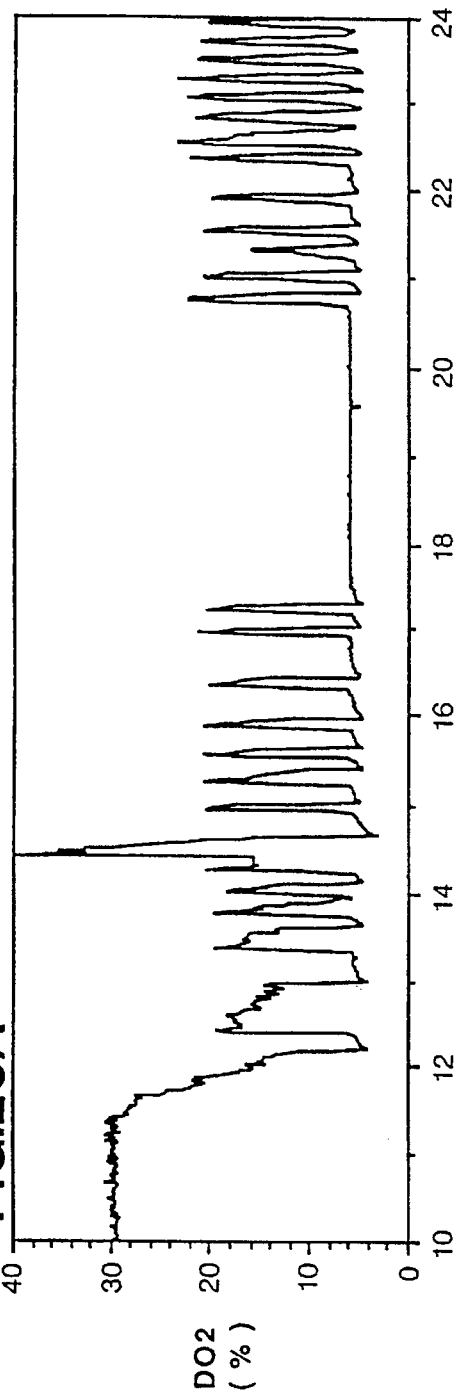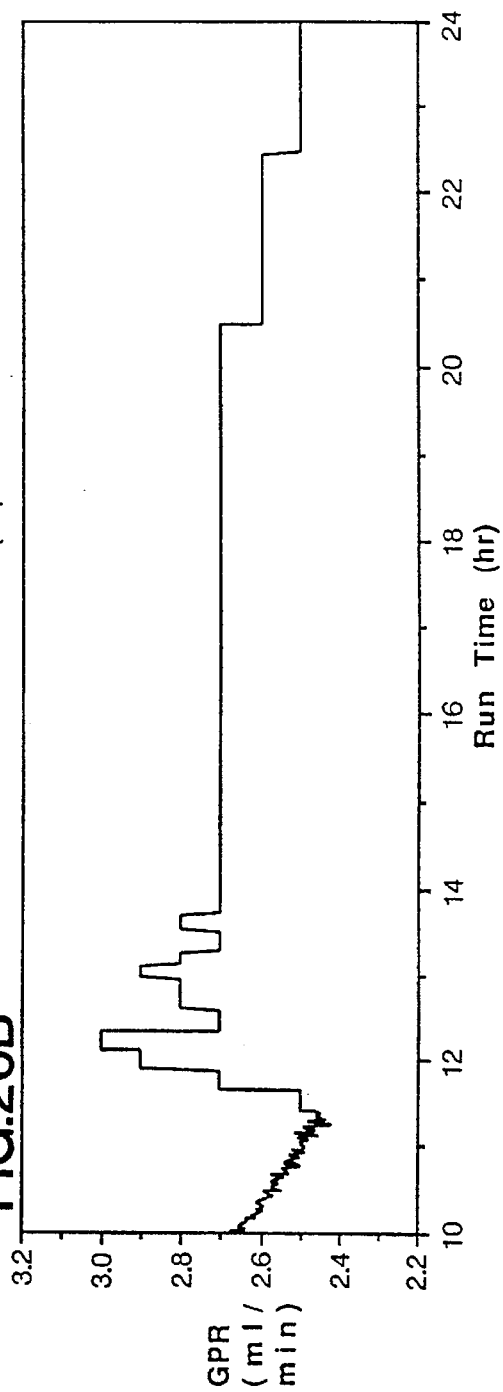

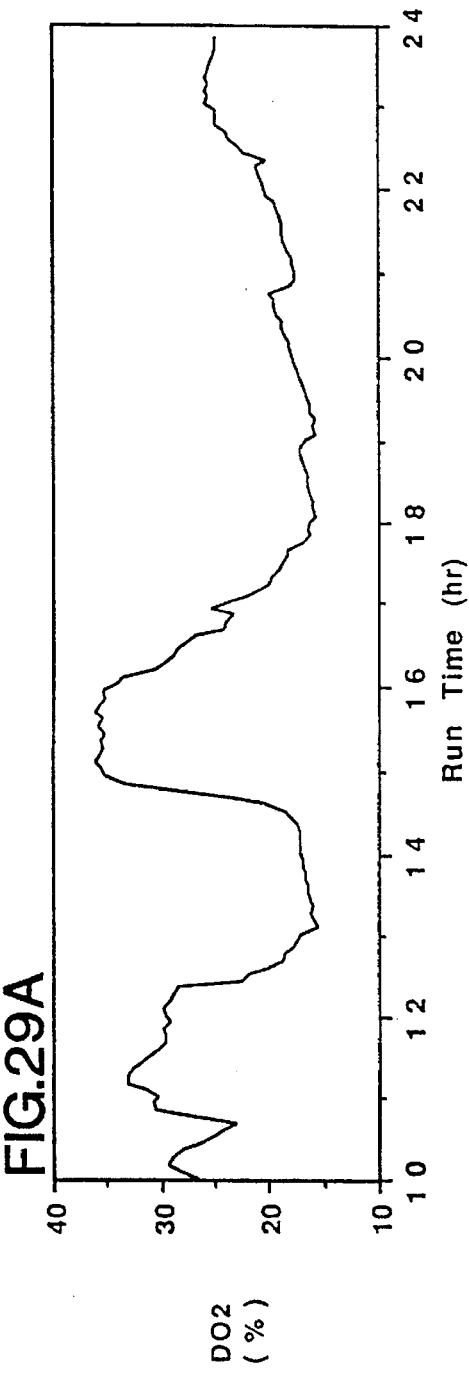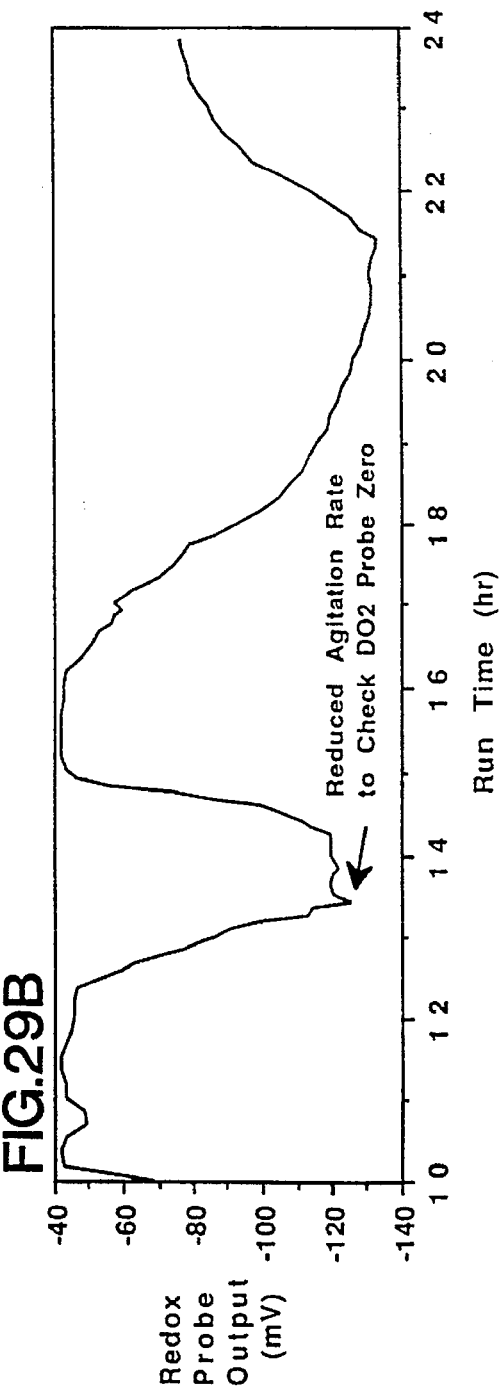

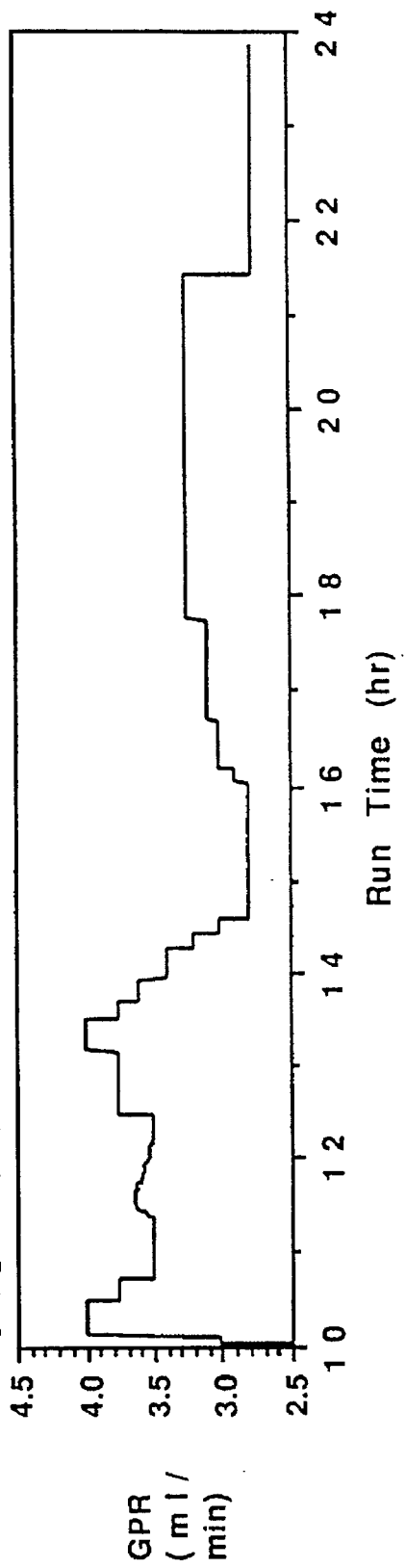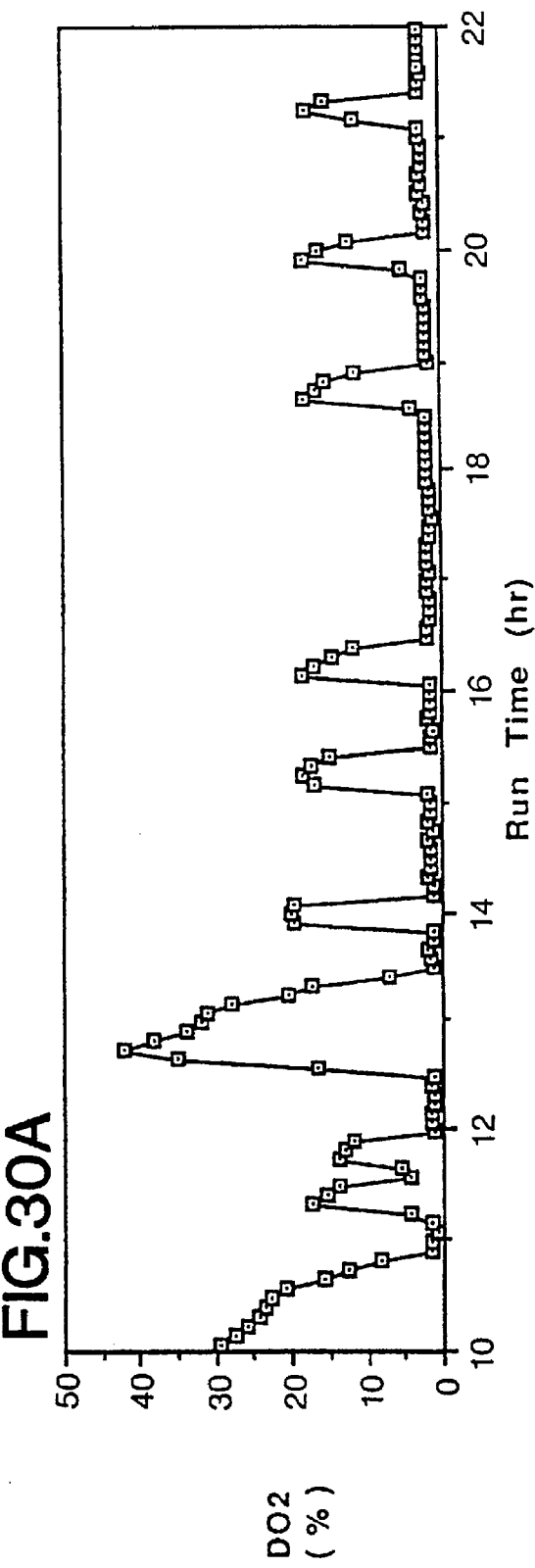

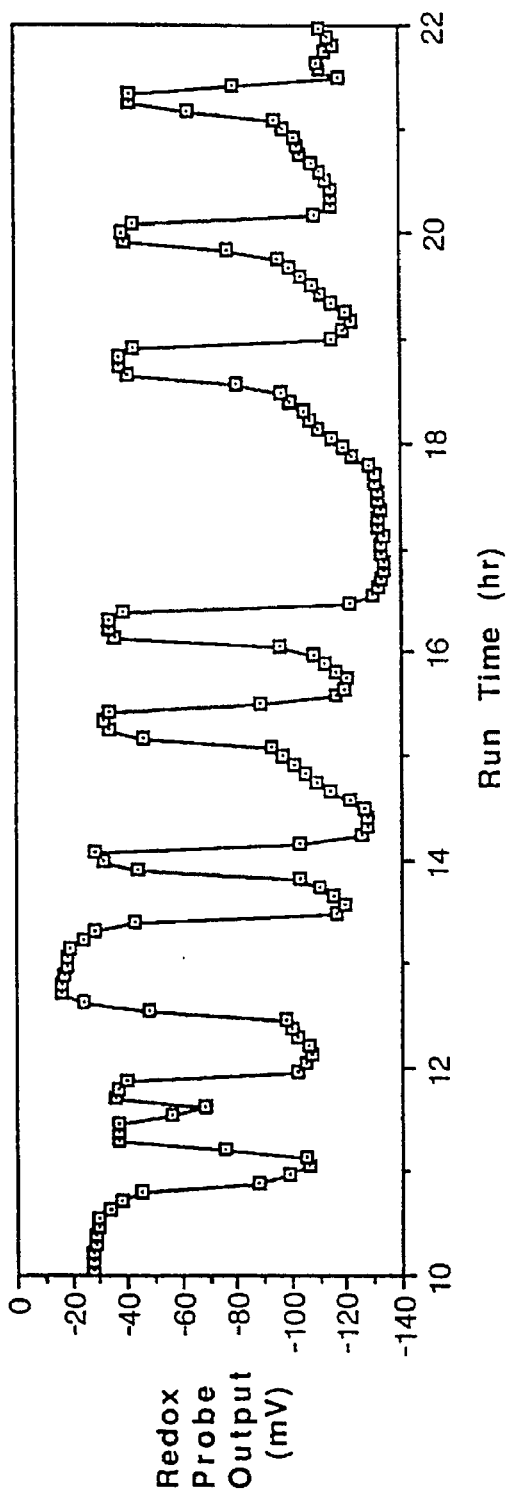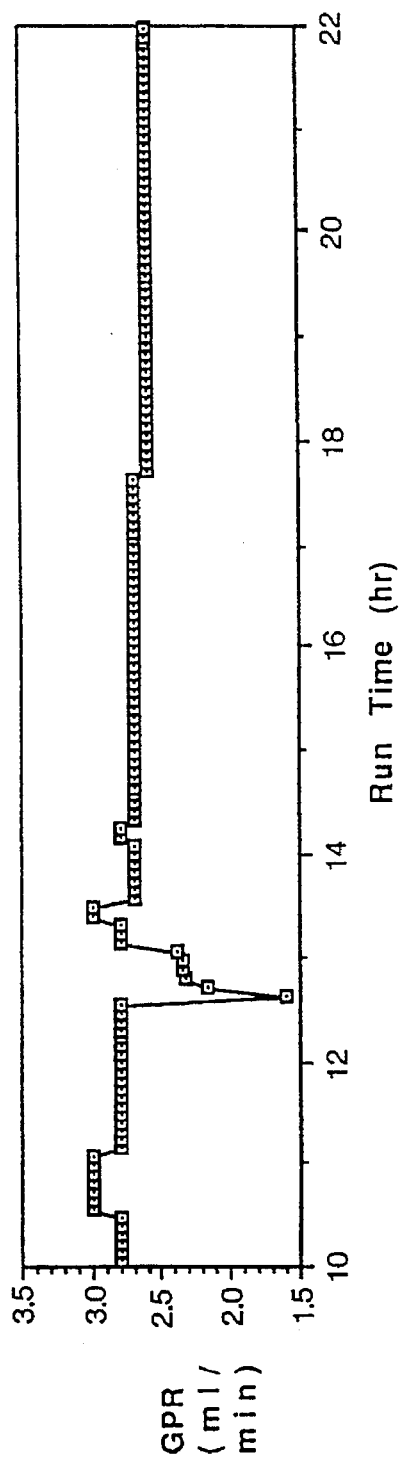

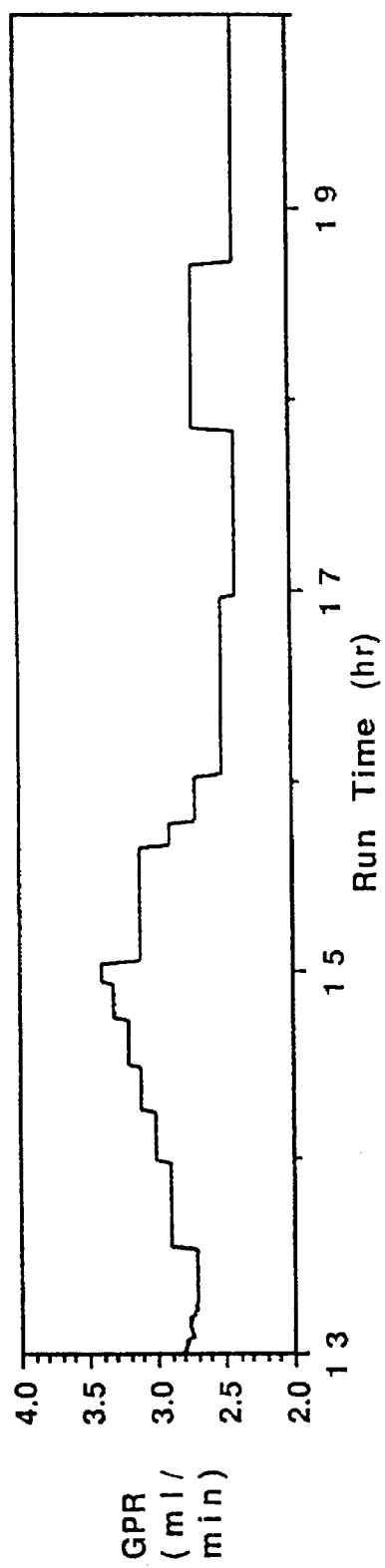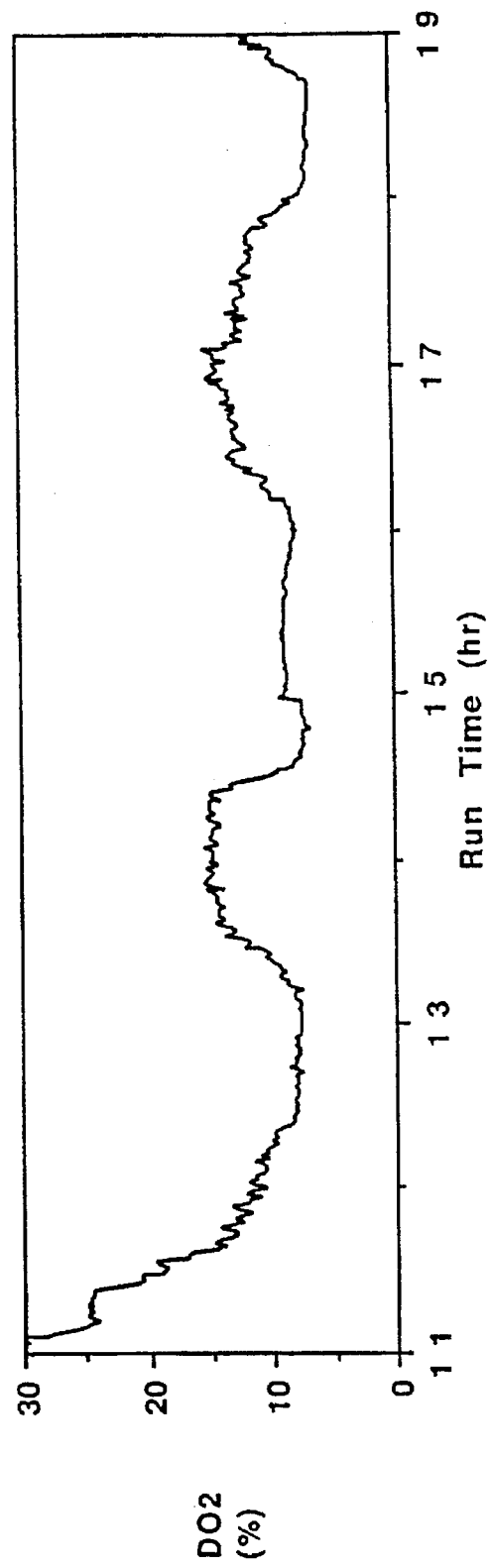

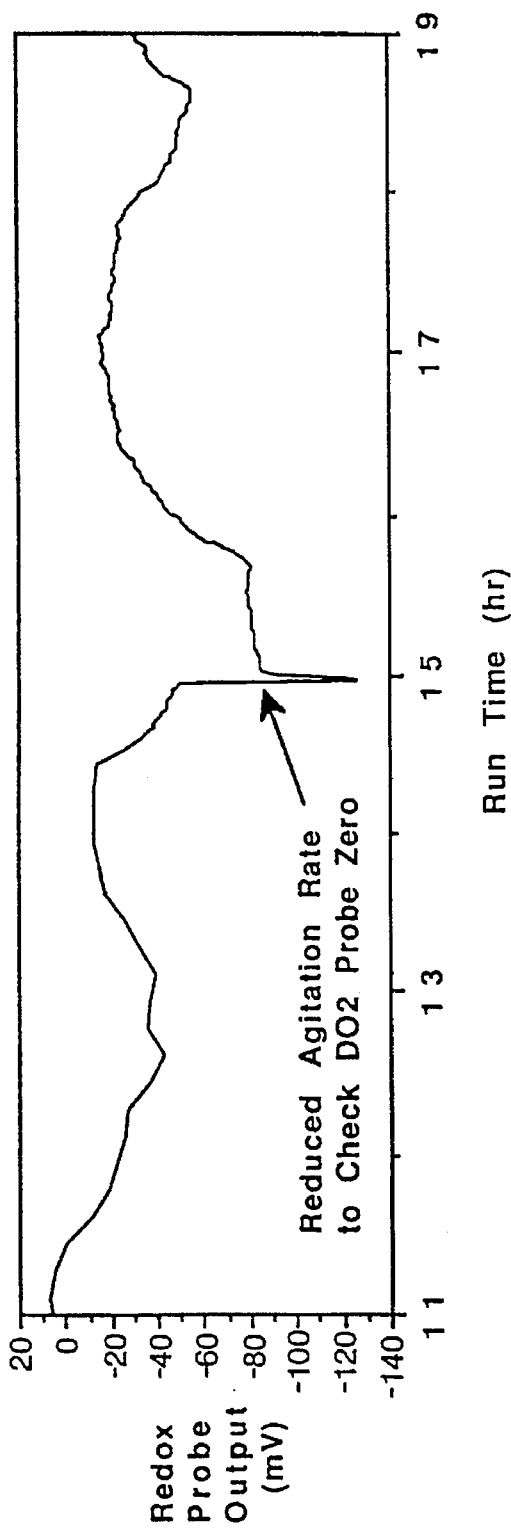
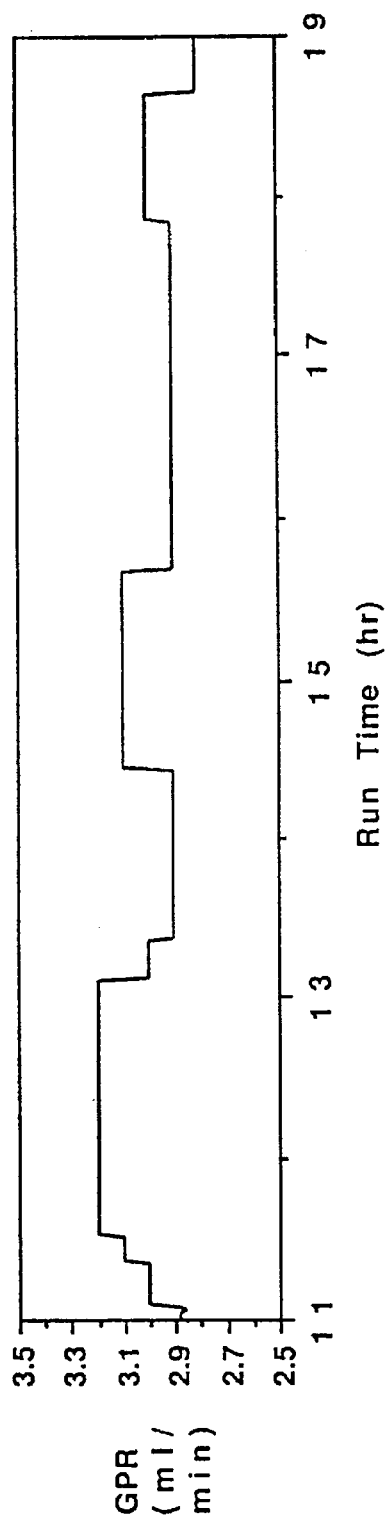

FERMENTOR WITH VERTICAL SHAFT

This is a divisional of application(s) Ser. No. 08/240,121 filed on 09 May 1994, now U.S. Pat. No. 5,487,980, which is a divisional of U.S. Ser. No. 07/989,844 filed on 23 Nov. 1992, now U.S. Pat. No. 5,342,763, which applications are incorporated herein by reference and to which applications priority is claimed under 35 USC §120.

BACKGROUND OF THE INVENTION

1. Field of the Invention

This invention relates to an improved method for producing polypeptides by bacterial fermentation. More specifically, this invention addresses the newly found problem of dissolved oxygen instability that is particularly manifest in large-scale bacterial fermentations.

2. Description of Related Art

The production of large quantities of relatively pure, biologically active polypeptides and proteins is important economically for the manufacture of human and animal pharmaceutical formulations, enzymes, and other specialty chemicals. For production of many proteins, recombinant DNA techniques have become the method of choice because large quantities of exogenous proteins can be expressed in bacteria and other host cells free of other contaminating proteins. The expression of proteins by recombinant DNA techniques for the production of cells or cell parts that function as biocatalysts is also an important application.

Producing recombinant protein involves transfecting host cells with DNA encoding the protein and growing the cells under conditions favoring expression of the recombinant protein. The prokaryote E. coil is favored as host because it can be made to produce recombinant proteins in high yields. Numerous U.S. patents on general bacterial expression of DNA encoding proteins exist, including U.S. Pat. No. 4,565,785 on a recombinant DNA molecule comprising a bacterial gene for an extracellular or periplasmic carrier protein and non-bacterial gene; U.S. Pat. No. 4,673,641 on co-production of a foreign polypeptide with an aggregate-forming polypeptide; U.S. Pat. No. 4,738,921 on an expression vector with a trp promoter/operator and trp LE fusion with a polypeptide such as IGF-I; U.S. Pat. No. 4,795,706 on expression control sequences to include with a foreign protein; and U.S. Pat. No. 4,710,473 on specific circular DNA plasmids such as those encoding IGF-I.

The electron transfer chain of bacterial organisms is capable of transferring electrons from substrates to molecular oxygen. The cytochromes are a group of iron-containing electron-transferring proteins on the electron transfer chain that act sequentially to transfer electrons from flavoproteins to molecular oxygen. The terminal cytochrome of the electron transfer chain is called cytochrome oxidase.

When a portion of a bacterial fermentor experiences a low dissolved oxygen ($DO_2$) concentration, the bacterial organism is induced for the production of the cytochrome d oxidase complex. Fu et al., Mol. Gen. Genetics, 226:209-213 (1991). This complex has a higher affinity for oxygen than the cytochrome o oxidase complex normally used. Anraku and Gennis, TIBS, 12: 262-266 (1987). Thus, when it is present, the cytochrome d complex allows the organism to continue with aerobic respiration under conditions of low oxygen concentration.

Ubiquinone is the electron transport mediator of the electron transport chain that is normally used by bacteria during vigorous aerobic growth. However, under conditions loosely defined as the approach of stationary phase [Poole and Ingledew, "Pathways of Electrons to Oxygen," in Neidhardt FC et al. (eds.) Escherichia coli and Salmonella typhimurium: Cellular and Molecular Biology, Vol. 1 (American Society for Microbiology, Washington, D.C., 1987) p. 180], the production of an alternative electron transport mediator, menaquinone, is induced. In most high-cell-density fermentations, a large portion of the procedure is conducted with the cells in a condition approximating stationary phase or the approach thereof. This may be caused by limitation of the carbon/energy source to avoid oxygen depletion, by measures used to induce product formation, or by the presence of the product.

The cytochrome d oxidass complex has a higher affinity for menaquinone than for ubiquinone (Anraku and Gennis, supra), and presumably uses menaquinone as its principal electron transport mediator when menaquinone is present. Unfortunately, organisms using menaquinone as their electron transport mediator grow with a much reduced efficiency. The aerobic growth yield of organisms missing ubiquinone is about 30% that of a wild-type organism. Wallace and Young, Biochim. Biophys. Acta, 461: 84-100 (1977).

Examples of microbial organisms with mutated electron transport mediators such as cytochrome d oxidase or cytochrome o oxidase are reported by Oden et al., Gene, 96:29-36 (1990); Oden and Gennis, J. Bacteriol., 173:6174-6183 (1991); Kelly et al., J. Bacteriol., 172: 6010-6019 (1990); Iuchi et al., J. Bacteriol., 172: 6020-6025 (1990); Soberon et al., J. Bacteriol., 172: 1676-1680 (1990); Poole et al., J. Gen. Microbiol., 135: 1865-1874 (1989); Fang et al., J. Biol. Chem., 264:8026-8032 (1989); James et al., FEMS Microbiol. Lett., 58:277-281 (1989); Green et al., J. Biol. Chem., 263:13138-13143 (1988); Soberon et al., J. Bacteriol., 171: 465-472 (1989); Sharma et al., Indian J. Microbiol., 27:26-31 (1987); Yang, Arch. Microbiol, 144:228-232 (1986); Matsushita and Kaback, Biochemistry, 25:2321-2327 (1986); Tamura-Lis and Webster, Arch. Biochem. Biophys., 244:285-291 (1986); Au et al., J. Bacteriol., 161:123-127 (1985); McInerney et al., Eur. J. Blochem., 141:447-452 (1984); Lorence et al., J. Bacteriol,, 157:115-121 (1984); Kranz et al., J. Bacteriol., 156:115-121 (1983); Green and Gennis, J. Bacteriol., 154: 1269-1275 (1983); Bryan and Kwan, Antimicrob. Agents Chemother., 19:958-964 (1981); Willison et al., FEMS Microbiol. Lett., 10:249-255 (1981); Willison and Haddock, FEMS Microbiol. Lett., 10:53-57 (1981); Hoffman et al., Eur. J. Biochem., 105:177-185 (1980); Hoffman et al., Eur. J. Biochem., 100:19-27 (1979); Haddock and Schairer, Eur. J. Biochem., 35:34-45 (1973); Haltia et al., EMBO J., 8:3571-3579 (1989); Dikshit et al., Arch. Biochem. Biophys., 293:241-245 (1992); Lemieux et al., J. Biol. Chem., 267: 2105-2113 (1992); Minagawa et al., J. Biol. Chem., 267:2096-2104 (1992); Dassa et al., Mol. Gen. Genet., 229:341-352 (1991); Williams et al., Biochem. J., 276:555-557 (1991); Puustinen et al., Biochemistry, 30:3936-3942 (1991); Denis et al., J. Biol. Chem., 265:18095-18097 (1990); Chepuri et al., Biochim. Biophys. Acta, 1018:124-127 (1990); Andersson and Roth, J. Bacteriol., 171: 6734-6739 (1989); Puustinen et al., FEBS Lett., 249:163-167 (1989); Daldal, J. Bacteriol., 170:2388-2391 (1988); Poole and Williams, FEBS Lett., 231:243-246 (1988); Georgiou et al., J. Bacteriol., 369:2107-2112 (1987); O'Brian and Maier, J. Bacteriol., 161:507-514 (1985); Green et al., J. Biol. Chem., 259:7994-7997 (1984); Au et al., J. Bacteriol., 157:122-125

(1984); Matsushita et al., *Proc. Natl. Acad. Sci. U.S.A.*, 80:4889–4993 (1983); Sasarman, *Rev. Can. Biol.*, 31:317–319 (1972); Van der Oost et al., *EMBO J.*, 11:3209–3217 (1992); Deutch, 92nd General Meeting of the American Society for Microbiology, New Orleans, La., May 26–30, 1992, Abstr. Gen. Meet. Am. Soc. Microbiol., 92:272 (1992); Mogi et al., *Biophys. J.*, 61:A284 (1992); Tron and Lemesle-Meunier, *Curr. Genet.*, 18:413–420 (1990); Shioi et al., *J. Bacteriol.*, 170: 5507–5511 (1988); Oden and Gennis, *J. Cell. Biol.*, 107:624A (1988); Webster and Georgiou, *Fed. Proc.*, 44: abstract 678 (1985); Terriere et al., *Biochem. Biophys. Res. Commun.*, 111:830–839 (1983); Green and Gennis, *Fed. Proc.*, 41: abstract 3652 (1982); Tamura-Lis and Webster, *Fed. Proc.*, 41: abstract 2799 (1982); Green et al., *Fed. Proc.*, 40:1669 (1981); Willison and John, *J. Gen. Microbiol.*, 115:443–450 (1979); and Hashimoto and Hino, *J. Sci. Hiroshima Univ. Ser. B Div. 2 (Bot)*, 15:103–114 (1975).

Fermentors for culturing bacteria are normally agitated to transfer oxygen from the gaseous phase to the liquid phase (i.e., the medium), and, secondarily, to maintain uniform concentrations of medium components, including $DO_2$, throughout the fermentor tank. The present invention is based on the unexpected finding that while during small-scale culturing to achieve DNA expression in bacteria the fermentation medium has a relatively stable $DO_2$ concentration, during large-scale bacterial fermentations sudden and dramatic, essentially uncontrollable changes in the $DO_2$ concentration of the medium may be experienced. These events prevent the successful and reproducible progression of large-scale fermentations, rendering them unsuitable for the production of high-quality protein or other products. When cultures are grown under glucose or other carbon/energy source limitation, feed control of the carbon/energy source can be programmed to provide adequate $DO_2$ concentration under most circumstances; however, in large reactors, this control action is found by the present invention not to be sufficient to counteract precipitous biological events.

Accordingly, it is an object of this invention to provide an effective and reliable method for avoiding the problem of $DO_2$ instabilities newly observed in bacterial fermentations.

It is a particular object to attain successful and reproducible progression of bacterial fermentations, especially large-scale bacterial fermentations, to produce high-quality polypeptides in an improved GMP process for FDA approval, and/or to produce the polypeptides in higher yield.

It is another object to provide a method for determining a culture's propensity for $D_2$ instability during the course of a bacterial fermentation.

These and other objects will be apparent to those of ordinary skill in the art.

SUMMARY OF THE INVENTION

This invention is based on the unexpected finding that the sudden changes in $DO_2$ content are of biological origin and are related to the switching of the organism between different respiration pathways. A thorough understanding of these events suggests that they can be prevented by careful design and operation of the fermentation vessel and/or the fermentation process.

One solution is to ensure that the region of maximum oxygen delivery to the liquid phase, i.e., the bottom of the vessel, is also the region of maximum entry of glucose. Thus, the fermentor is designed so as to have the glucose inlet at the bottom thereof.

In an alternative fermentor configuration, the points and rates of glucose entry can be distributed throughout the vessel to match approximately the rate of oxygen availability in the various regions of the vessel.

For fed-batch fermentations in which the increasing broth volume often significantly changes the geometric relationship between the agitator impellers and the liquid volume, and in larger fermentors, i.e., those having at least approximately 1000 liters of capacity, preferably about 1000 to 100,000 liters of capacity, the preferred solution to the problem addressed by this invention to allow the most efficient use of the fermentation vessel is to mutate the host organism to inactivate a key element of one of the respiration pathways (e.g., cytochrome d oxidase complex, cytochrome o oxidase complex, menaquinone, or one of the NADH dehydrogenases) so that the organism can no longer switch between the two electron transport pathways.

Specifically, the present invention provides a process for producing a polypeptide of interest from a fermentation of bacterial host cells comprising nucleic acid encoding the polypeptide which method comprises conducting the fermentation using bacterial host cells having an impaired electron transport chain, i.e., an inactivation in one of their respiratory chains.

In another aspect, the invention provides a method for determining the propensity of a bacterial cell culture for $DO_2$ instability in a large-scale fermentor comprising (a) culturing the cell culture in the presence of a carbon/energy source introduced at a set feed rate in a small-scale fermentor configured so that the $DO_2$ concentration throughout the cell culture is not homogeneous during fermentation, (b) after significant cell mass has been produced, increasing the feed rate of the carbon/energy source, and (c) determining if non-linearity occurs in the slope of $DO_2$ concentration versus time or if oscillations in $D_2$ concentration are induced after the feed rate of the carbon/energy source is increased.

BRIEF DESCRIPTION OF THE DRAWINGS

FIG. 2 illustrates the lineage of protease-deficient *E. coli* W3110 host strain designated 27C7.

FIG. 10 depicts the construction of pLS32Tsc from pLS33Tsc and pLS321amB.

FIG. 11 depicts the nucleotide sequence of the expression cassette and amino acid sequence encoded by the lamB signal sequence and the IGF-I gene in plasmid pLS32Tsc (SEQ. ID NOS. 11 and 12, respectively).

FIG. 13A and FIG. 13B illustrate the glucose pump rate in g/min. (FIG. 13A) and the percent $DO_2$ (FIG. 13B) versus time during a 1000-L fermentation of strain 27C7 transformed with pLS32Tsc.

FIG. 18 depicts the nucleotide sequence of the EcoRI—EcoRI fragment (from positions 1149 to 1633) of p200 containing the MF alpha I prepro and IGF-I gene sequences (SEQ. ID NO. 13).

FIG. 26A and FIG. 26B illustrate % $DO_2$ (FIG. 26A) and glucose pump rate (ml/min) (FIG. 26B) versus time in the modified 10-L fermentor shown in FIG. 1 with an organism derived from strain 27C7, designated 37D6, transformed with expression vector pBKIGF-2B.

FIG. 29A, FIG. 29B and FIG. 29C illustrate % $DO_2$ (FIG. 29A), redox probe output (mV) (FIG. 29B), and glucose pump rate (ml/min) (FIG. 29C) versus time in the modified 10-L fermentor with an untransformed cytochrome d oxidase deletion mutant of the host W3110tonA.

FIG. 30A, FIG. 30B and FIG. 30C illustrate % $DO_2$ (FIG. 30A), redox probe output (mV) (FIG. 30B), and glucose pump rate (ml/min) (FIG. 30C) versus time in the modified 10-L fermentor with a kanamycin-sensitive IGF-I production organism designated 40B4 transformed with pBKIGF-2B.

FIG. 31A, FIG. 31B and FIG. 31C illustrate % $DO_2$ (FIG. 31A), redox probe output (mV) (FIG. 31B), and glucose pump rate (ml/min) (FIG. 31C) versus time in the modified 10-L fermentor with a cytochrome d oxidase deletion mutant of strain 40B4 transformed with pBKIGF-2B.

FIG. 32A, FIG. 32B and FIG. 32C illustrate % $DO_2$ (FIG. 32A), redox probe output (mV) (FIG. 32B), and glucose pump rate (ml/min) (FIG. 32C) versus time in the modified 10-L fermentor with a cytochrome o oxidase deletion mutant of strain 40B4 transformed with pBKIGF-2B.

DESCRIPTION OF THE PREFERRED EMBODIMENTS

A. Definitions

Figure 1:
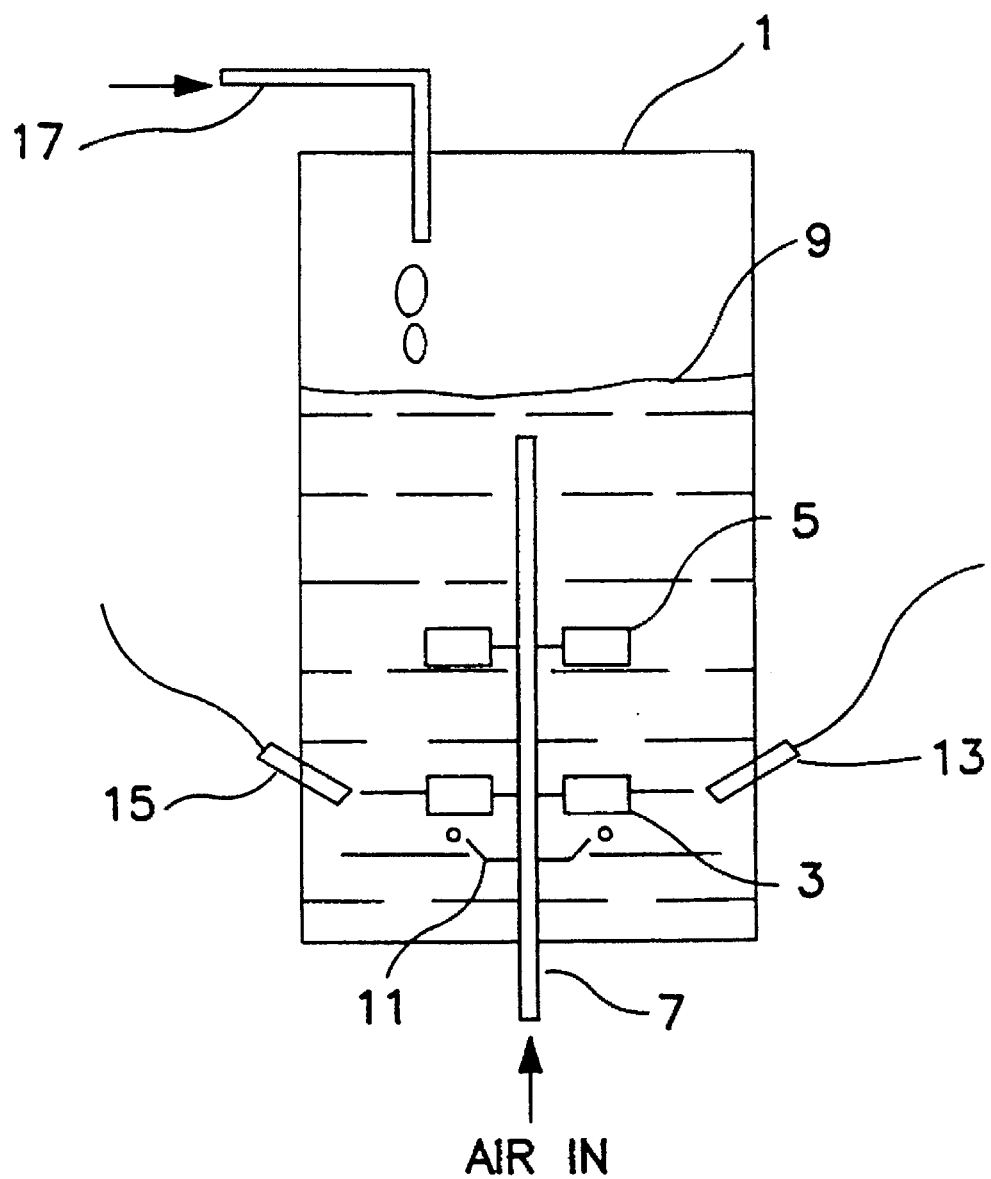
FIG. 1 illustrates the configuration of a 10-L fermentor designed to mimic large-scale $DO_2$ instabilities.

As used herein, "polypeptide of interest" refers generally to peptides and proteins having more than about 10 amino acids. The polypeptides may be endogenous to the bacterial host cell, or preferably, may be exogenous to the host cell, such as yeast polypeptides, or more preferably, mammalian polypeptides. Examples of bacterial polypeptides include, e.g., alkaline phosphatase and β-lactamase. Examples of mammalian polypeptides include molecules such as, e.g., renin, a growth hormone, including human growth hormone, des-N-methionyl human growth hormone, and bovine growth hormone; growth hormone releasing factor; parathyroid hormone; thyroid stimulating hormone; thyroxine; lipoproteins; α1-antitrypsin; insulin A-chain; insulin B-chain; proinsulin; follicle stimulating hormone; calcitonin; leutinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombssin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor; receptors for hormones or growth factors; integrin; thrombopoietin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF)

such as TGF-alpha and TGF-beta, including TGF-β1, TGF-β2, TGF-β3, TGF-β4, or TGF-β5; insulin-like growth factor-I and -II (IGF-I and IGF-II); insulin-like growth factor binding proteins; CD proteins such as CD-3, CD-4, CD-8, and CD-19; erythropoietin; osteoinductive factors; immunotoxins; a bone morphogenetic protein (BMP); somatotropins; an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The preferred polypeptides of interest are those that are easily produced in bacterial cells with a minimum of proteolysis and a maximum in properly refolded or active material and need not be glycosylated for their intended utility. Examples of such mammalian polypeptides include IGF-I, growth hormone, DNase, relaxin, growth hormone releasing factor, insulin, urokinase, immunotoxins, and antigens. Particularly preferred mammalian polypeptides include IGF-I and growth hormone.

As used herein, "IGF-I" refers to insulin-like growth factor from any species, including bovine, ovine, porcine, equine, and preferably human, in native sequence or in variant form and recombinantly produced. In a preferred method, the IGF-I is cloned and its DNA expressed, e.g., by the process described in EP 128,733 published Dec. 19, 1984.

As used herein, the phrase "carbon/energy source" refers to a source of carbon and energy for the cells. Examples of such a source include glycerol, succinate, lactate, and sugars such as, e.g., glucose, lactose, sucrose, and fructose. The selection of the particular carbon/energy source to employ will depend mainly on the bacterium being utilized. The preferred carbon/energy source for *E. coli* fermentation is glucose.

As used herein, the phrase "electron transport chain" or "respiratory chain" refers to the chain consisting of a series of "electron carriers" in bacteria capable of transferring electrons from substrate molecules to molecular oxygen. They are thus involved in the aerobic respiration pathway of, and the promotion of oxygen transfer within, the bacteria. These electron carriers include, but are not limited to, a NADH dehydrogenase, a guinone such as ubiquinone and menaguinone, and a component of the cytochrome o oxidase complex or cytochrome d oxidase complex.

A bacterial organism with an "impaired" or "inactivated" electron transport chain refers to bacteria that are mutated so as to render inactive or disable at least one, but not all, of the electron carriers constituting its electron transport chains. This mutation may be by way of deletion of the genetic component representing an electron carrier, or alternatively, by alterations in the nucleotides of the genetic component such that it no longer functions in the way defined above. Thus, for example, if the genetic component is cytochrome o or d oxidase, the organism may produce the cytochrome o oxidase gene product but not the cytochrome d oxidass gene product, or the cytochrome d oxidass gene product but not the cytochrome o oxidase gene product. The preferred bacterial organism has an inactivated cytochrome d or o oxidase gene, more preferably an inactivated cytochrome o oxidase gene, and most preferably lacks the latter gene.

As used herein, "large-scale" fermentation refers to fermentation in a fermentor that is at least approximately 1000 liters in volumetric capacity, i.e., working volume, leaving adequate room for headspace. "Small-scale" fermentation refers generally to fermentation in a fermentor that is no more than approximately 100 liters in volumetric capacity, preferably no more than approximately 10 liters.

B. Modes for Carrying Out the Invention

For purposes of this invention, an altered host strain contains one or more nucleotide mutations within its electron transport chains, preferably its cytochrome o oxidase or cytochrome d oxidase complex gene, so that any one or more, but not all, of the electron carrier genes in the electron transport chains is inactivated. The strain is preferably an *E. coli* strain. Such strain variants are suitably prepared by introducing appropriate nucleotide changes into the bacterial strain DNA. The strain variants include, for example, deletions from, or insertions or substitutions of, nucleotides within the nucleic acid sequence of the native electron transport chain gene sufficient to prevent the gene from allowing the strain to switch from one aerobic respiratory chain to the other under conditions favoring $DO_2$ instability. Such genes can be readily identified by the methods outlined in Example III below. Any combination of deletion, insertion, and substitution can be made to arrive at the final strain, provided that the final strain possesses the desired characteristics.

For the design of variants of bacterial strains, the optimum characteristics will depend mainly on the nature of the mutation. The site(s) for mutation can be modified individually or in series, e.g., by (1) substituting first with nucleotides encoding conservative amino acid choices and then with more radical selections depending upon the results achieved, (2) deleting the target nucleotides, or (3) inserting nucleotides encoding amino acids of the same or a different class adjacent to the located site, or combinations of options 1–3.

The preferred method of nucleotide alteration is sequence deletions of or within the domain of the electron carrier gene. These deletions generally will be from at least two nucleotides up to approximately 5.8 kilobases or longer, depending on the particular gene or genes being deleted, and typically are contiguous. The length of the cytochrome o oxidase gene in *E. coli* is 5.8 kilobases. Chepuri et al., *J. Biol. Chem.*, 265:11185–11192 (1990). Contiguous deletions ordinarily are made in even numbers of residues, but single or odd numbers of deletions are within the scope hereof.

Nucleic acid sequence insertions are intraseguence insertions of single or multiple nucleotides within the electron carrier gene, generally ranging from about 1 to 5 nucleotides, most preferably 1 to 3. Insertions are preferably made in even numbers of residues, but this is not required.

A third group of variant strains herein, are nucleic acid substitution variants. These variants have at least one nucleic acid within the electron carrier gene of the native bacterial molecule removed and a different residue inserted in its place.

Substantial modifications in the activity of the electron carrier gene product are accomplished by selecting substitutions that differ significantly in their effect on maintaining (a) the structure of the chain's backbone in the area of the substitution, for example, as a sheet or helical conformation, (b) the charge or hydrophobicity of the molecule at the target site, or (c) the bulk of the side-chain. Naturally occurring residues are divided into groups based on common side-chain properties:

(1) hydrophobic: norleucine, cys, met, ala, val, leu, tyr, phe, trp, ile;

(2) neutral hydrophilic: ser, thr;

(3) acidic: asp, glu;

(4) basic: asn, gln, his, lys, arg; and (5) residues that influence chain orientation: gly, pro.

Preferably, the strain variants herein are those with an *E. coli* W3110tonA background in which the complete gene of the electron carrier molecule is deleted, and most preferably in which the complete gene for cytochrome o oxidase complex has been removed.

Variant genes introduced into a wild-type bacterial host are prepared by a variety of methods known in the art. These methods include, but are not limited to, transposon mutagenesis if the mutagenesis is done in vivo, or preparation in vitro by, e.g., oligonucleotide-mediated (or site-directed) mutagenesis, alanine-scanning mutagenesis, random mutagenesis, PCR mutagenesis, or cassette mutagenesis of an earlier prepared variant or a non-variant version of the electron carrier gene.

Transposon mutagenesis, a preferred method, typically involves transductions with phage P1kc, derived from P1, as described, for example, by Miller, *Experiments in Molecular Genetics* (Cold Spring Harbor, N.Y.: Cold Spring Harbor Laboratory, 1972). It also may involve transposon genetics, as described, e.g., by Kleckner et al., *J. Mol. Biol.*, 116:125–159 (1977).

Oligonucleotide-mediated mutagenesis represents a preferred in vitro method for preparing substitution, deletion, and insertion variants of the electron carrier gene, although other methods may be utilized as desired. This technique is well known in the art as described by Zoller and Smith, *Nucleic Acids Res.*, 10:6487 (1982). Briefly, the electron carrier DNA is altered by hybridizing an oligonucleotide encoding the desired mutation to a DNA template, where the template is the single-stranded form of a plasmid or bacteriophage containing the unaltered or native DNA sequence of the electron carrier gene. After hybridization, a DNA polymerase is used to synthesize an entire second complementary strand of the template that will thus incorporate the oligonucleotide primer, and will code for the selected alteration in the electron carrier DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75: 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153:3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, a single-stranded DNA template may be generated by denaturing double-stranded plasmid (or other) DNA using standard techniques.

A useful method for identification of certain nucleotides or regions of the electron carrier gene that are preferred locations for mutagenesis is called "alanine-scanning mutagenesis," as described by Cunningham and Wells, *Science*, 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine-scanning or random mutagenesis is conducted art he target codon or region and the expressed electron carrier variants are screened for the optimal combination of desired activity.

For alteration of the native DNA sequence, another method is the combination of oligonucleotide-directed mutagenesis and random mutagenesis as described by Kunkel et al., *Methods Enzymol.*, 154:367 (1987). In this method, oligonucleotide-directed mutagenesis is employed to randomize particular codons of the wild-type electron carrier gene to encode all possible residues. A pool of oligonucleotides with complementary sequence (about 10–15 bases) flanking the codon of choice is used. The codon of choice is replaced with the nucleotides NNS, where N is any nucleotide and S is G or C, to give a pool of oligonucleotides encoding all possible amino acids in 32 codons.

In this preferred method, a pBR322-derived plasmid with a single-stranded origin of replication is prepared as a single-stranded plasmid template in an *E. coli* dut- ung- strain such as CJ236 (Kunkel et al., supra). These two mutations in the strain cause the incorporation of one or more uracil nucleotides into the single-stranded DNA instead of thymine. The random oligonucleotides are annealed, filled in with *E. coli* phage T7 DNA polymerase, ligated, and transformed into a wild-type strain of *E. coli* such as W3110. The wild-type strain corrects the uracil misincorporation using the synthetic mutant strand as a template so as to produce about 90% mutants.

Mutant DNA may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis, a method well known in the art, is also suitable for making nucleotide variants of the electron carrier gene. The PCR technique generally refers to the procedure described by Erlich, ed., *PCR Technology*, (Stockton Press, N.Y., 1989), the chapter by R. Hiquchi, p. 61–70.

Another method for preparing variants, cassette mutagenesis, is based on the technique described by Wells et al., *Gene*, 34:315 (1985). The starting material is the plasmid (or other vector) comprising the electron carrier DNA to be mutated. The codon(s) in the electron carrier DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the electron carrier DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated electron carrier DNA sequence.

Mutant nucleic acid may also be chemically synthesized and assembled by any of a number of techniques, prior to expression in a host cell. [See, e.g., Caruthers, U.S. Pat. No. 4,500,707; Balland et al., *Biochimie*, 67:725–736 (1985); Edge et al., *Nature*, 292:756–762 (1982)].

Certain deletions and insertions, and substitutions in particular, are not expected to produce radical changes in the characteristics of the electron carrier molecule. When it is difficult to predict the exact effect of the substitution, deletion, or insertion in advance of doing so, one skilled in the art appreciates that the effect may be evaluated by routine screening assays.

For example, a DNA variant typically may be made by transposon mutagenesis or random and/or site-specific mutagenesis of the native electron-carrier-encoding nucleic acid and transfection or integration of the electron carrier variant gene into the chromosomes of a bacterial host, or by random mutagenesis of a host containing the native electron carrier gene. The nucleic acid variant may then be screened in a suitable screening assay for the desired characteristic. For example, in one embodiment, the cytochrome d oxidase deletion mutant strains are screened for cytochrome d oxidase complex activity by spectroscopic analysis of isolated cytoplasmic membranes or by the inability to induce $DO_2$ instabilities as described in Example III. Mutant strains with increased $DO_2$ stability are selected.

If the nucleic acid encoding the electron carrier variant is produced outside the bacterial host cell that will ultimately produce the polypeptide of interest, the nucleic acid is introduced into the appropriate bacterial cell using any suitable method, including transfection and transformation by a vector containing the electron carrier variant DNA and, preferably, integration into the chromosome of the bacterial cells by any suitable method known in the art. An example of insertion of the electron carrier gene into the host genome includes that using the *E. coli* species as host. In this case, included in the vector for transformation is a DNA sequence that is complementary to a sequence found in *E. coli* genomic DNA. Transfection of *E. coli* with this vector results in homologous recombination with the genome and insertion of the electron carrier variant gene into the chromosome. The host for this purpose either lacks the corresponding native electron carrier gene or has its native electron carrier gene replaced by the corresponding variant gene upon integration thereof.

Examples of mutant bacteria that can be screened for impaired electron transfer chain activity to determine if they are suitable for use in the invention herein include those described by Oden et al., supra; Oden and Gennis, *J. Bacteriol.*, supra; Kelly et al., supra; Iuchi et al., supra; Soberon et al., (1990), supra; Poole et al., supra; Fang et al., supra; James et al., supra; Green et al., *J. Biol. Chem.*, 263, supra; Soberon et al., (1989), supra; Sharma et al., supra; Yang, supra; Matsushita and Kaback, supra; Tamura-Lis and Webster, *Arch. Biochem. Biophys.*, supra; Au et al., *J. Bacteriol.*, 161, supra; McInerney et al., supra; Lorence et al., supra; Kranz et al., supra; Green and Gennis, *J, Bacteriol.*, supra; Bryan and Kwan, supra; Willison et al., supra; Willison and Haddock, supra; Hoffman et al., (1980), supra; Hoffman et al., (1979), supra; Haddock and Schairer, supra; Haltia et al., supra; Dikshit et al., supra; Lemieux et al., supra; Minagawa et al., supra; Dassa et al., supra; Williams et al., supra; Puustinen et al., *Biochemistry*, supra; Denis et al., supra; Chepuri et al., *Biochim. Biophys. Acta*, supra; Andersson and Roth, supra; Puustinen et al., *FEBS Lett.*, supra; Daldal, supra; Poole and Williams, supra; Georgiou et al., supra; O'Brian and Maier, supra; Green et al., *J. Biol. Chem,*, 259, supra; Au et al., *J. Bacteriol.*, 157, supra; Matsushita et al., supra; Sasarman, supra; Van der Oost et al., supra; Deutch, supra; Mogi et al., supra; Tron and Lemesle-Meunier, supra; Shioi et al., supra; Oden and Gennis, *J. Cell. Biol.*, supra; Webster and Georgiou, supra; Terriere et al., supra; Green and Gennis, *Fed. Proc.*, 41: supra; Tamura-Lis and Webster, *Fed. Proc.*, 41: supra; Green et al., *Fed. Proc.*, 40: supra; Willison and John, supra; and Hashimoto and Hino, supra.

The bacterial cells carrying the mutated electron carrier gene can inherently also harbor the polypeptide of interest. For example, alkaline phosphatase is a protein that is homologous to *E. coli* and can be induced without any further transfection of the cell with vector DNA. For heterologous polypeptides such as, e.g., IGF-I and growth hormone, the heterologous nucleic acid (e.g., cDNA or genomic DNA) is suitably inserted into a replicahie vector for expression in the bacterial culture medium under the control of a suitable promoter for bacteria. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes, and a promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2:95 [1977]). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substitutedby a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemass for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide also contains a promoter that is recognized by the host bacterial organism and is operably linked to the nucleic acid encoding the polypeptide of interest. Promoters suitable for use with bacterial hosts include the β-lactamase and lactose promoter systems (Chang et al., *Nature*, 275:615 [1978]; Goeddel et al., *Nature*, 281:544 [1979]), alkaline phosphatase, a tryptophan (trp) promoter system (Goeddel, *Nucleic Acids Res.*, 8:4057 [1980] and EP 36,776) and hybrid promoters such as the tac promoter (deBoer et aL., *Proc. Natl. Acad. Sci. U.S.A.*, 80:21–25 [1983]). However, other known bacterial promoters are suitable. Their nucleotide sequences have been published, thereby enabling a skilled worker operably to ligate them to DNA encoding the polypspride of interest (Siebenlist et al., *Cell*, 20:269 [1980]) using linkers or adaptors to supply any required restriction sites. Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., *Proc, Natl. Acad. Sci. U.S.A.*, 74: 5463–5467 (1977) or Messing et al., *Nucleic Acids Res.*, 9:309 (1981) or by the method of Maxam et al., *Methods in Enzymology*, 65:499 (1980).

The bacterial host cells used for expressing the vectors encoding the polypeptide of interest are those that contain at least one operable electron carrier component that mediates the electron transport chain, so that the respiration pathway of the cells is not totally impaired. In the method herein, a suitable strain utilized for this purpose is typically one that is mutated such that one, but not all, of its native electron carriers is inactivated. Preferably, this inactivation is achieved by replacement of the native electron carrier gene with a variant electron carrier gene that is homologous to the native electron carrier gene normally present in the host cells.

All bacteria, including both archaebacteria and eubacteria, generally have more than one terminal oxidase (Anraku and Gennis, supra), and thus all except obligate anaerobes are potentially susceptible to $DO_2$ instabilities upon culturing. Suitable bacteria for this purpose include aerobic and facultative anaerobic bacteria, whether archaebacteria and eubacteria, especially eubacteria, and most preferably Enterobacteriaceae. Examples of useful bacteria include Escherichia, Enterobacter, Azotobacter, Erwinia, Bacillus, Pseudomonas, Klebsiella, Proteus, Salmonella, Serratia, Shigella, Rhizobia, Vitreoscilla, and Paracoccus. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicabilityof the replicon in the cells of a bacterium. For example, *E. coli*, Serratia, or Salmonella species can be suitably used as the host when well known plasmids such as pBR322, pBR325, pACYA177, or pKN410 are used to supply the replicon.

*E. coli* strain W3110 is a particularly preferred parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 1A2, which has the complete genotype tonAΔ; *E. coli* W3110 strain 9E4, which has the complete genotype tonAΔ ptr3; *E. coli* W3110 strain 27C7 (ATCC 55,244), which has the complete genotype tonAΔ ptr3 phoAΔE15 Δ(argF-lac)169 ompTΔ degP41kan[4]; *E. coli* W3110 strain 37D6, which has the complete genotype tonAΔ ptr3 phoAΔE15 Δ(argF-iac)169 ompTΔ degP41kan[r] rbs7Δ ilvG; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990.

Host cells are transformed with the above-described expression vectors of this invention and cultured in conventional nutrient media modified as appropriate for the promoter utilized.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for bacterial cells that contain substantial cell-wall barriers. Another method for transformation employs polyethylene glycol/DMSO, as described in Chung and Miller, *Nucleic Acids Res.*, 16:3580 (1988). Yet another method is the use of the technique termed electroporation.

Bacterial cells used to produce the polypeptide of interest of this invention are cultured in suitable media in which the promoter can be constitutively or artificially induced as described generally, e.g., in Sambrook et ai., supra. Examples of suitable media are given below in the example section.

Any necessary supplements besides carbon, nitrogen, and inorganic phosphate sources may also be included at appropriate concentrations introduced alone or as a mixture with another supplement or medium such as a complex nitrogen source.

If the polypeptide is alkaline phosphatase, the composition of the carbon, nitrogen, and phosphate sources of the nutrient medium is preferably such that during the phase of intensive polypeptide accumulation the glucose content of the medium is approximately 0%, the phosphate content is more than about 0.5 mM and less than about 5 mM, and the nitrogen concentration is not more than about 30 µg/ml. Glucose feeding is preferably carried out during the transitional phase. The fermentation medium is preferably subjected to intensive mixing and the fermentation is preferably carried out at about 25°–40° C., more preferably about 37° C.

Gene expression may be measured in a sample directly, for example, by conventional northern blotting to guantitate the transcription of mRNA. Thomas, *Proc. Natl. Acad. Sci. U.S.A.*, 77:5301–5205 (1980). various labels may be employed, most commonly radioisotopes, particularly $^{32}$p. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

The polypeptide of interest preferably is recovered from the periplasm or culture medium as a secreted polypeptide, although it also may be recovered from host cell lysates when directly expressed without a secretory signal. Alternatively, the cells or portions thereof may be used as biocatalysts or for other functions without substantial purification.

It is often preferred to purify the polypeptide of interest from recombinant cell proteins or polypeptides to obtain preparations that are substantially homogeneous as to the polypeptide of interest. As a first step, the culture medium or lysate is centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane bound, is soluble, or is present in an aggregated form. The polypeptide thereafter is solubilized and folded, if necessary, and is purified from contaminant soluble proteins and polypeptides, with the following procedures being exemplary of suitable purification procedures: fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; and gel filtration using, for example, Sephadex G-75.

In another embodiment of this invention, a specially configured fermentation apparatus is used to determine the propensity of a given bacterial cell culture for $DO_2$ instability during the progress of a large-scale bacterial fermentation. This monitoring method utilizes a small-scale fermentor. The fermentor is configured such that the $DOp_2$ concentration throughout the cell culture is not homogeneous during fermentation. This non-homogeneity can be achieved by various means. One preferred means is by equipping the fermentor with an inlet at its top for introducing the carbon/energy source. Another configuration is to equip the fermentor with only two impellers, rather than the three normally used such that there is poor mixing at the top of the fermentor. Preferably, the carbon/energy source inlet and the two impellers are both featured in the fermentor apparatus. Another preferred feature is that the fermentor have not only a probe for $DO_2$ but also a redox probe for measuring redox potential. These probes are preferably mounted on the fermentor nearest the bottom-most impeller.

The most preferred embodiment used for this method is a 10-liter fermentor the diagram of which is shown in FIG. 1. In this figure the vessel 1 is equipped with two impellers, a bottom 3 and top 5 impeller, preferably Rushton-type impellers, mounted on a vertical shaft 7 normally operated at 150–1000 rpm. The two impellers are located significantly below (i.e., at least one/fourth of the total culture volume below) the surface 9 of the fermentation medium. A gas inlet means 11, preferably a ring air sparger or rotating air sparger, is used to introduce air into the bottom of the fermentor, preferably at about 10 standard liters per minute.

A $DO_2$ probe 13 preferably mounted in the wall of the vessel near the bottom impeller 3 measures the concentration of oxygen dissolved in the fermentation medium (and therefore accessible to the organism) at the bottom of the vessel. That signal is preferably sent to a monitoring and control computer, which then regulates the feed rate of the carbon/energy source for the bacteria (such as glucose) into the fermentor. The tank is also equipped with a redox probe 15 preferably mounted in the wall of the tank at the same level as the $DO_2$ probe near the bottom impeller 3. This redox probe measures the redox potential of the medium, through a signal for relaying the output for redox potential. In this configuration, the carbon/energy source is fed through a liquid inlet means 17, such as tubing, into the top of the vessel. Not shown is a feed line into the top of the vessel that is used to add $NH_4OH$ on demand to control the pH of the broth. Also not shown is another feed line into the top of the vessel, which may be used for a slow feed of complex nutrients.

The method for determining the propensity of a bacterial cell culture for $DO_2$ instability in large-scale fermentors involves culturing in the vessel described above the bacteria containing the desired DNA to be expressed in a fermentation medium. During this initial culturing step a carbon/energy source for the bacteria, such as glucose, is fed at a predetermined feed rate into the fermentation medium. In FIG. 1, this feeding would be through the top inlet means 17 of the fermentor. Air is fed into the bottom of the fermentor. In FIG. 1, the air is fed through the bottom inlet means 11 into the fermentation medium. The redox potential and the $DO_2$ concentration of the fermentation medium are monitored during the fermentation by means of the respective probes therefor 13 and 15.

When significant cell mass has been accumulated, i.e., when the culture has sufficient oxygen uptake ability to exceed the oxygen transfer rate of the reactor, that is, about 10–50 grams per liter of cells, dry weight, the feed rate of the carbon/energy source is increased to drive the $DO_2$ from its control set point to a lower value. This increase in feed rate is preferably only a slight increase so that the $DO_2$ is slowly lowered. Significant non-linearity in the $DO_2$ decline (i.e., a change from a gradual slope to a rapid slope in the $DO_2$ vs. time graph) and/or the ability to induce $DO_2$ oscillations at the higher experimentally determined critical glucose feed rate indicate propensity of the culture for producing $DO_2$ instabilities.

The following examples are offered byway of illustration and not by way of limitation. The disclosures of all references cited in the specification are expressly incorporated herein by reference.

EXAMPLES

Introduction

It has been found herein that when the organism has previously been induced for the presence of menaquinone and the cytochrome d oxidass complex, it has the ability to scavenge low concentrations of oxygen but does so inefficiently. When sufficient oxygen is present, it would appear that this inefficient pathway is not allowed to function.

An examination of the stoichiometry of cell growth reveals the consequences of inefficient menaquinone-facilitated utilization of oxygen. The C, H, O, N composition of *E. coli* is approximately $C_{4.18}H_{7.36}N_1O_{2.03}$. The equation describing aerobic growth can then be written as:

$$aC_6H_{16}O_6 + bO_2 + cNH_3 = dC_{4.18}H_{7.36}N_1O_{2.03} + eCO_2 + fH_2O$$

Using this equation, the moles of oxygen used per mole of glucose consumed can be estimated as a function of growth yield as shown in the following table:

| Growth Yield (g cell/g glucose) | Moles $O_2$/Mole Glucose |
| --- | --- |
| 0.4 | 3.1 |
| 0.1 | 5.3 |
| 0.0 | 6.0 |

If an *E. coli* culture that has expressed the cytochrome d oxidase complex and menaguinone encounters a region of low $DO_2$ concentration, the cytochrome o oxidass system with its lower affinity for oxygen is no longer able to support aerobic respiration. Thus, the cytochrome d oxidass-mediated respiration pathway must be used. This switch to the inefficient respiratory pathway reduces the ATP supply and causes a lower growth yield. As a result, the oxygen used per mole of glucose fed increases. Since the vessel is already in a state that allows local regions of low $DO_2$ concentration, the increased oxygen consumption will expand the region of low $DO_2$ concentration as long as the glucose supply remains constant. This causes more cells to shift to the inefficient pathway and further increases local and overall oxygen demand.

Thus, there is a tendency for a rapid, self-propagating shift to higher respiration rates and low $D_2$ concentrations throughout the entire tank. This progression will only cease if there is (by way of increasing the oxygen driving force as the $DO_2$ concentration is lowered) enough residual oxygen transfer capacity to support the higher rate of oxygen utilization accompanying the inefficient respiration. Since it is desirable to fully utilize the maximum capacity of the fermentor to transfer oxygen, any excess capacity available under normal operation probably will not be sufficient and the $DO_2$ concentration in the entire vessel will be driven to zero.

This invention employs the means necessary to overcome the tendency of the operation to lose efficiency as a result of this self-propagating shift.

Revealing data were obtained by modifying the large fermentor to follow the $D_2$ level at both the bottom and the top of the vessel. A modified 10-L fermentor was then used to replicate the $DO_2$ instabilities in the large fermentor. Mutations in the cytochrome oxidase complexes were used to confirm switching between the respiration pathways as the biological origin of the $DO_2$ instabilities. The mutated hosts were also evaluated for their suitability for producing heterologous recombinant proteins. Surprisingly, the cytochrome o oxidase mutant proved to be superior to the cytochrome d oxidase mutant and produced equivalent quantities of the product as compared to the unmutated isogenic comparison host in the unmodified 10-liter fermentor.

EXAMPLE I

Identification of $DO_2$ Instability Problem in 1000-L Fermentor i. Construction of host cell strain 27C7

The host used to produce recombinant human IGF-I in the fermentation described in this example was a derivative of *E. coil* W3110, designated 27C7. The complete genotype of 27C7 is tonAΔ ptr3 phoAΔAE15 Δ(argF-lac)169 ompTΔ degP41kan. The derivation of strain 27C7 is diagrammed in FIG. 2 and is described below. Strain 27C7 was deposited on Oct. 30, 1991 in the American Type Culture Collection as ATCC No. 55,244.

Strain 27C7 was constructed in several steps using techniques involving transductions with phage P1kc, derived from P1 (J. Miller, *Experiments in Molecular Genetics* (Cold Spring Harbor, N.Y.: Cold Spring Harbor Laboratory, 1972) ), and transposon genetics [Kleckner et al., *J. Mol. Biol.*, 116: 125–159 (1977)]. The starting host used was *E. coil* K12 W3110, which is a K12 strain that is F-, λ- [Bachmann, *Bact. Rev.*, 36:525–557 (1972); Bachman, "Derivatives and Genotypes of Some Mutant Derivatives of *Escherichia coli* K-12," p. 1190–1219, In F. C. Niedhardt et al., ed., *Escherichia coli and Salmonella typhimurium: Cellular and Molecular Biology*, vol. 2, American Society for Microbiology, Washington, D.C. (1987)].

Figure 3A:
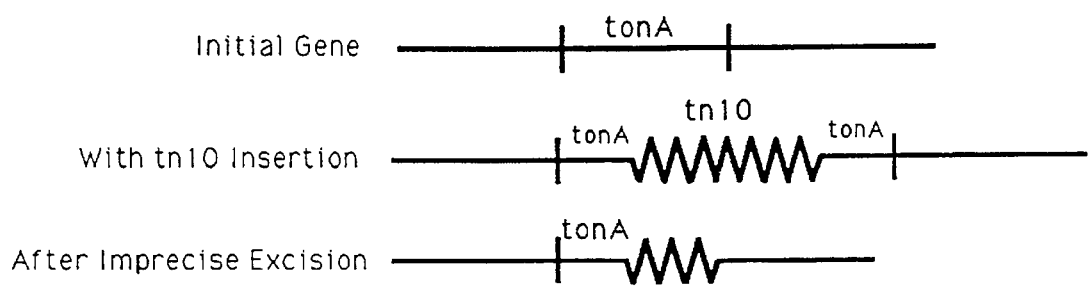
FIGS. 3A and 3B depict the schemes for the mutation of the tonA and phoA genes, respectively, in *E. coli* strain W3110.
Figure 3B:
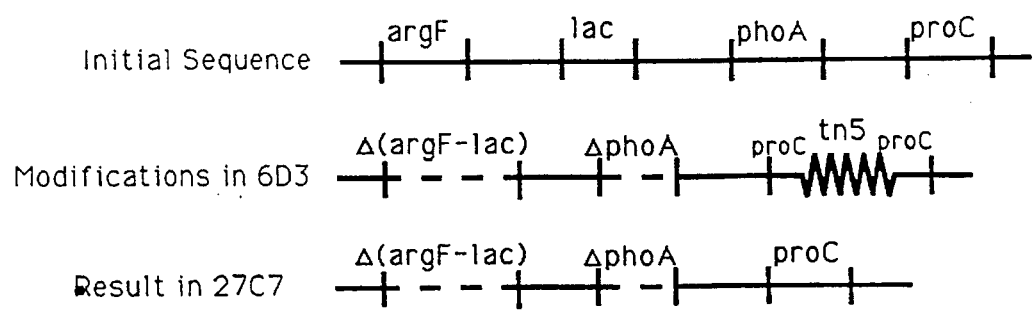
Figure 4:
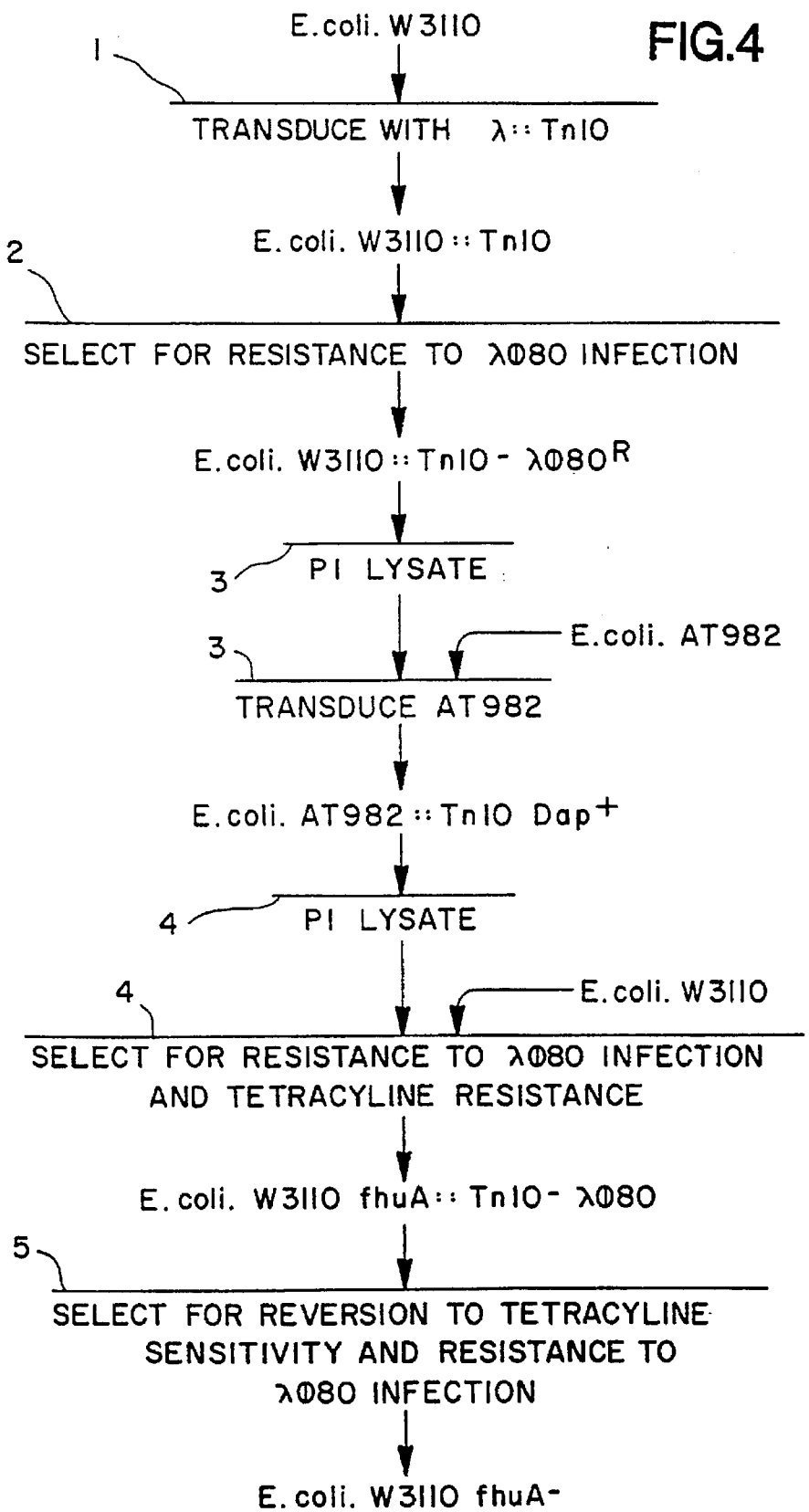
FIG. 4 depicts in detail the construction for the elimination of the tonA gene from W3110.

First, the tonA gene (fhuA) [Kadner et al., *J. Bact.*, 143:256–264 (1980), Bachmann, *Microbiol. Rev.*, 47: 180–230 (1983), Bachman, "Linkage Map of *Escherichia coli* K-12," edition 7, p. 807–876, in F. C. Niedhardt et al., ed., "*Escherichia coli* and *Salmonella tryphimurium: Cellular and Molecular Biology*, Vol. 2, American Society for Microbiology, Washington, D.C., 1987] was deleted from W3110 by the insertion and subsequent imprecise excision of a Tn10 transposon into the tonA gene. This construction is diagrammed in FIGS. 3B and 4.

In the first step of this procedure, *E. coli* W3110 was transduced with λ::Tn10 to generate a population of *E. coli* W3110 cells with Tn10 randomly inserted into the chromosomes thereof [Kleckner et al., *J. Mol. Biol.*, supra].

The *E. coli* W3110::Tn10 population was grown in L broth at 37° C. to a cell density of about $1 \times 10^9$/ml. A total of 0.5 ml of the culture was centrifuged and the pellet was resuspended in 0.2 ml of a λphi80 lysate containing $7.0 \times 10^9$ pfu. The phage was allowed to adsorb for 30 minutes at 37° C. The suspension was then spread on EMB plates supplemented with tetracycline (15 µg/ml). After an overnight incubation at 37° C., the colonies were pooled in 3 ml of L broth, grown overnight at 37° C., washed twice, and resuspended in L broth. A bacteriophage P1kc lysate was made on this culture [Miller, J. H., *Experiments in Molecular Biology*, supra, page 304].

*E. coli* AT982 (no. 4546, *E. coli* Genetic Stock Center, New Haven, Conn.) was transduced to tetracycline resistance by this P1kc lysate. Transductants were selected on L broth plates supplemented with tetracycline (15 µg/ml) and 40 µg/ml diaminopimelic acid (dap). The resulting transductants were screened for tetracycline resistance and the regeneration of the dap gene ($dap^+$, $tet^R$). Transductants with the $dap^+$, $tet^R$ genotype were then tested for λAphi80 resistance.

P1kc lysates were then made on several $dap^+$, $tet^R$, λphi80-resistant strains. The lysates were used to transduce *E. coli* W3110 to tetracycline resistance. The transductants were screened and selected for λphi80 resistance.

Tetracycline-sensitive isolates were selected from the W3110 tonA::Tn10-λphi80R transductants. [Maloy and Nunn, *J, Bacteriol.*, 145:1110 (1981)]. These isolates were checked for λphi80 resistance and tetracycline sensitivity after single colony purification.

DNA was isolated from several tetracycline-sensitive λphi80-resistant mutants and digested with SstII. The SstII-digested DNA was characterized by the Southern blot procedure using radioactively labeled and SstII-digested λ::Tn10 DNA as a probe to determine if the Tn10 had been excised [Davis et al., *Advanced Bacterial Genetics* (Cold Spring Harbor Laboratory, N.Y., 1980)]. One of the tetracycline-sensitive isolates was shown to have lost two of the Tn10 hybridization bands as compared to the hybridization between DNA from the λ::Tn10 and the parental W3110 tonA::Tn10λphi80R. A third hybridization band had an altered mobility, indicating that a deletion caused by the imprecise excision of Tn10 had occurred.

SDS-gel electrophoresis of outer membrane preparations from the strain with an imprecise Tn10 excision revealed that the band assumed to be the protein encoded by tonA had an altered electrophoretic mobility as compared to the wild-type protein encoded by the tonAgene. The resulting protein was non-functional as a λphi80 phage receptor protein. A second independent strain that also had undergone imprecise excision of Tn10 showed no protein encoded by tonA on the SDS gel.

Neither of these strains demonstrated reversion to tetracycline resistance or to λphi80 susceptibility, indicating that there was an imprecise excision of all or part of the Tn10 transposon together with either a partial or complete deletion of the tonA gene. Thus, the protein encoded by the tonA gene (MW 78,000) was eliminated from the outer membrane, rendering the W3110 tonA strain resistant to several bacteriophages. The resulting strain, designated 1A2, is resistant to bacteriophages T1 and φ80.

The ptr3 gene [Cheng et al., *J. Bacteriol.*, 140: 125–130 (1979)] was introduced into strain 1A2 as follows. First, the thyA8 mutation was isolated in 1A2 by selecting for trimethoprim resistance to form strain 9E1. Then the argA81::tn10 locus was transported from 9D9 (obtained from B. Bachman, *E. coli* Genetic Stock Center, New Maven, Conn.) into 9E1 by transduction with phage P1kc to form 9E3. The ptr3 locus is between thyA8 and argA81. Transduction with P1 phage grown on a ptr3 mutant [9D7, *J. Bact.*, 140:125 (1979)] resulted in the introduction of the ptr3 mutation simultaneously with the conversion of thyA8 and argA81::Tn10 to wild-type loci. This strain, designated 9E4, lacks the periplasmic protease III. The conclusion that the ptr3 mutation is included in 9E4 is supported by strongly improved IGF-I accumulation in the resultant strain.

Then, two more deletion mutations, phoAΔE15[Sarthyet al., *J. Bacteriol.*, 145:288–292 (1981)] and Δ(argF-lac)169 [Schweizer and Boos, *Mol. Gen. Genet.*, 192:293–294 (1983)], were simultaneously transferred into 9E4 by genetic linkage to a kanamycin-resistance transposon inserted into a proline biosynthetic gens (proC::Tn5), contained in 6D3, obtained from Professor Barry Wanner, Purdue University. This constructkon is diagrammed in FIG. 3B.

The transposon was eliminated by selecting for a protothrophic ($pro^+$) isolate on glucose minimal agar plates after P1 transduction with 1A2. The introduction of the phoA mutation eliminates alkaline phosphatase expression and was recognized as transductants that form white colonies on glucose-minimal agar plates with 0.2 mM phosphate and 20 mg/l 5-bromo-4-chloro-3-indolyl phosphate. Likewise, the Δ(argF-lac)169 mutation causes the loss of the enzyme beta-galactosidase (a lac-phenotype) and results in cells that form white colonies on MacConkey-1% lactose agar plates. The resultant strain was designated 27A7.

The ompT deletion [Earhart et al., *FEBS Microbiol. Lett.*, 6:277–280 (1979)] was introduced into 27A7 by P1 cotransduction. It should be noted that this ompT deletion extends into the neighboring ent gene cluster which codes for the attachment proteins for colicins B and D. First, a linked Tn10 insertion in the pure gene was inserted next to the ompT deletion using conventional transduction techniques [intermediates 3E9 (similar strain obtainable from Dr. Carol Mross, University of Wisconsin), 16B2, 25C9 (*J. Bacter.*, 153:1104–1106 (1983)), and 25D3]. Then, the purE::Tn10 construct was transduced into 27A7. Finally, this strain was transduced to purine prototrophy to remove the transposon. Maintenance of the ompTΔ genotype was confirmed by colicin B resistance in the resultant strain, which is designated 27C6. This strain lacks the outer membrane protease VII.

Finally, an additional periplasmic protease mutation, degP41kan[4][Strauch et al., *J, Bacteriol.*, 171:2689–2696 (1989); Harvard Medical School] was transduced into strain 27C6 by standard techniques. This mutation was constructed in vitro by replacing a section of the degP gene with the kanamycin gene. This is not a transposon but allows for selection of the deletion using kanamycin resistance.

This final strain, 27C7, has the following characteristics: it is phage resistant, lacks three proteases, fails to grow on lactose, and fails to produce alkaline phosphatase on the depletion of phosphate in the media, the same conditions that induce production of rhIGF-I.

ii. Description/Construction of IGF-I Expression Plasmid pLS33Tsc

The secretion plasmid pLS32Tsc used to transform strain 27C7 contains the IGF-I gene. The transcriptional and translational sequences required for expression of the IGF-I gene in *E. coli* are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamb signal sequence or alternatively the STII signal sequence. The majority of rhIGF-I is found in the cell periplasmic space. Plasmid pLS32Tsc confers tetracycline resistance upon the transformed host.

Plasmid pLS32Tsc was constructed in several steps using as intermediate plasmids pLS32, pAP1amB, pLS321amB, pLS331amB, and pLS33Tsc.

Step 1: pLS32

Figure 5:
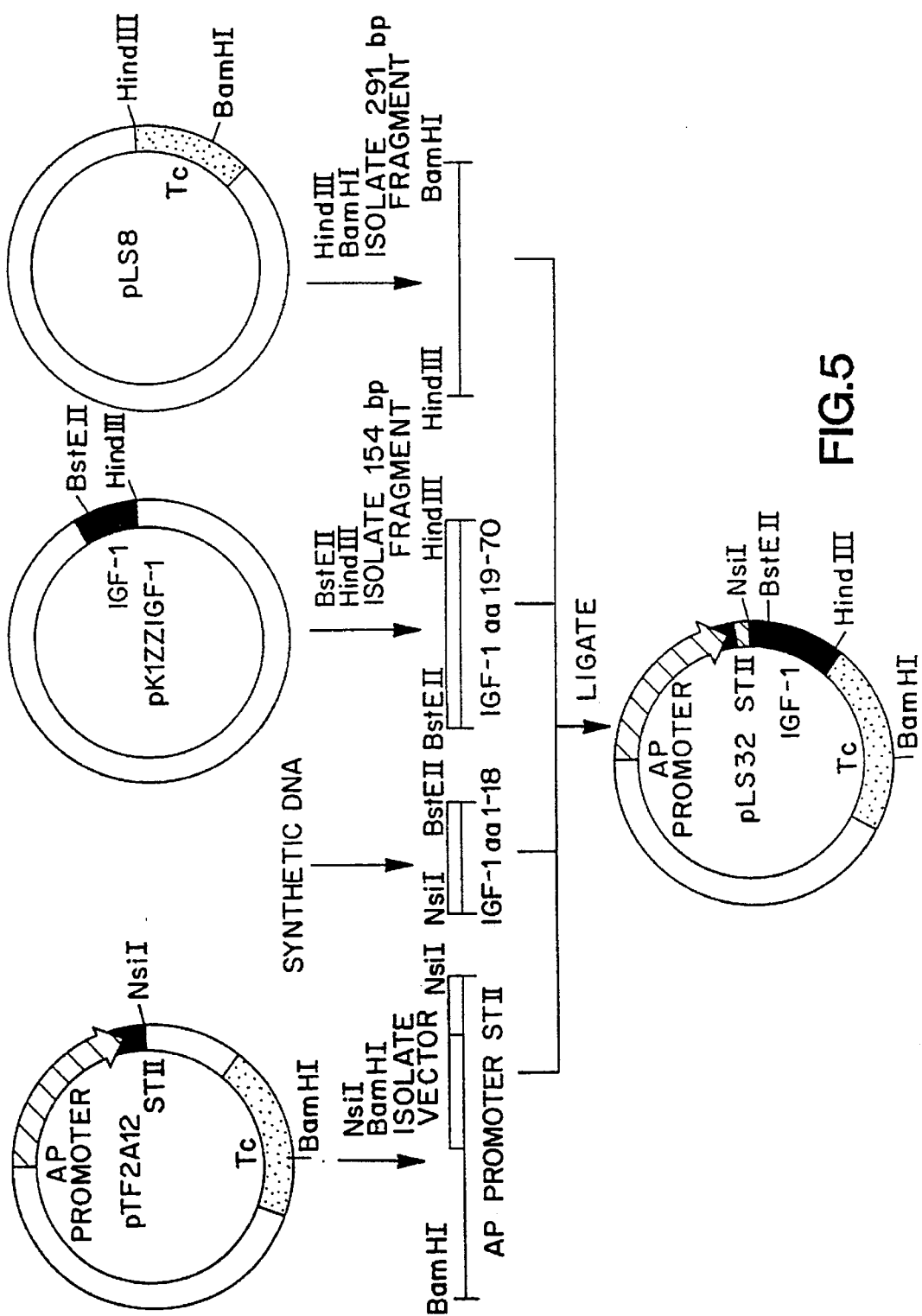
FIG. 5 depicts the construction of plasmid pLS32, an intermediate plasmid in preparing pLS32Tsc, which contains a gene encoding IGF-I.

The plasmid pLS32 results in the fusion of the IGF-I coding sequence to that of the heat-stable enterotoxin II (STII) signal sequence and was prepared by ligating together four DNA fragments as shown in FIG. 5. The first of these was the vector pTF2A12 [Paborsky et al., *Biochemistry*, 28:8072–8077 (1989)] from which the small NsiI-BamHI fragment containing the tissue factor gene had been removed. The STII signal sequence is described by Picken et al., *Infect. Immun.*, 43:269–275 (1983).

The second fragment was a 55-bp synthetic duplex encoding the first 18 amino acids of mature IGF-I. This duplex has the following sequence:

coding sequence for the start of the tetracycline gene of pBR322[Sutcliffe, *Cold Spring Harbor Symposia on Quantitative Biology*, 43:77–90 (1978)] in which a HindIII restriction site was engineered immediately upstream of the methionine start codon.

The resulting plasmid, pLS32, efficiently expresses and secretes rhIGF-I to the media. The following two construction steps were made to replace the STII signal sequence with the lamb signal sequence, improving product yield.

Step 2: pAP1amB

Figure 6:
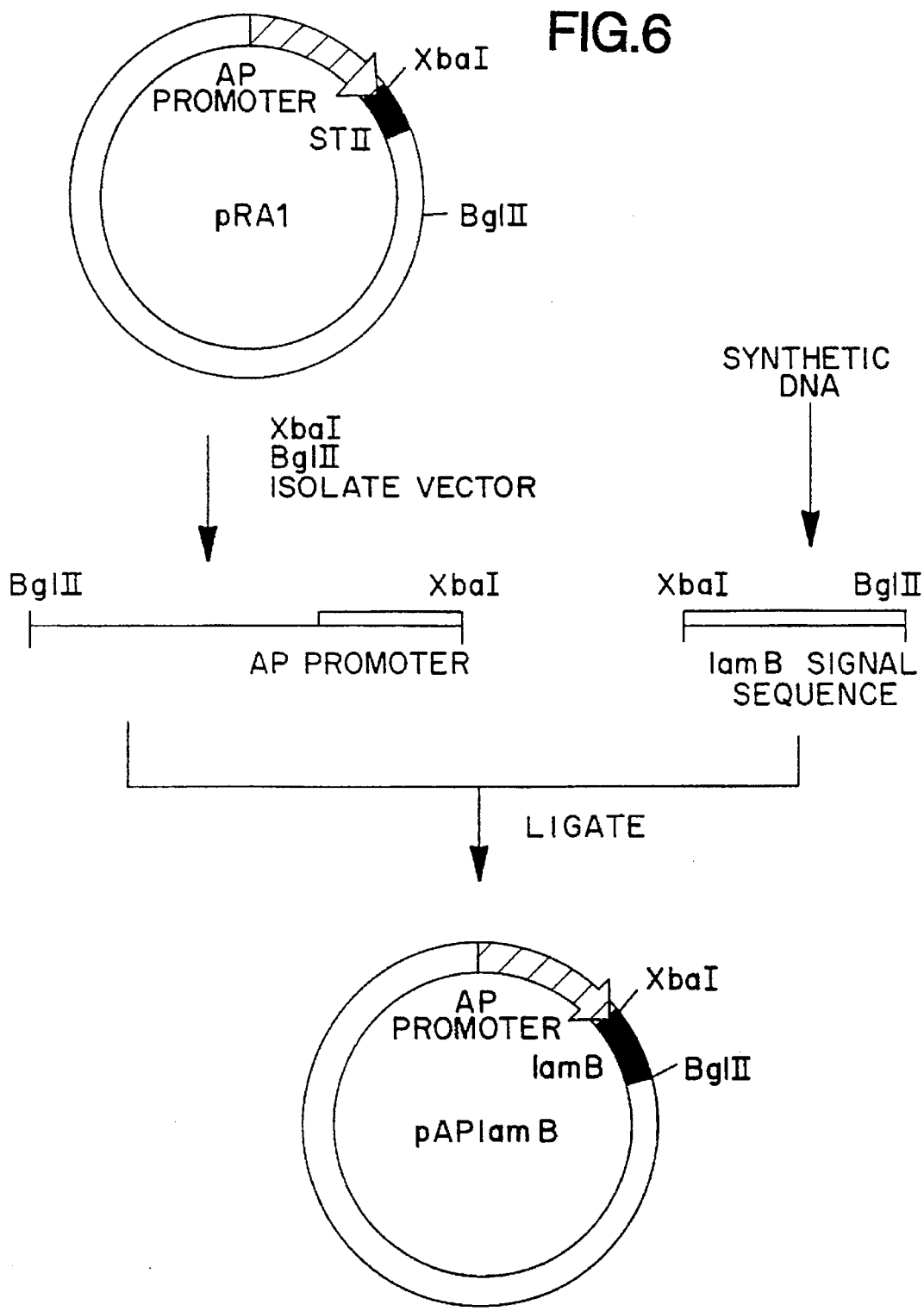
FIG. 6 depicts the construction of pAP1amB, another intermediate plasmid in preparing pLS32Tsc and in preparing an additional intermediate plasmid, pLamBIGF.

The plasmid pAP1amB was constructed as shown in FIG. 6 by ligating together two DNA fragments, and results in the placement of the lamb signal coding sequence downstream of the AP promoter and the trp Shine-Dalgarno sequence. Included in the ligation was the vector pRA1 in which the small XbaI-BglII fragment had been removed. This plasmid is a derivative of phGH1 [Chang et al., *Gene*, 55:189–196 (1987)], which latter plasmid contains the AP promoter, the STII signal, and DNA encoding hGH. pRA1 differs from phGH1 in that it contains DNA encoding relaxin A chain (the sequence of which is described in U.S. Pat. No. 4,758,516) rather than hGH and it contains a convenient BglII restriction site downstream of the promoter and ribosome binding site. The second piece in the ligation was a 80-bp synthetic DNA duplex with the following sequence, which encodes the lamb signal sequence, which has been described by Clement and Hofnung, *Cell*, 27: 507–514 (1981):

```
5'-    GGTCCCGAAACTCTGTGCGGTGCTGAACTGGTTGACGCTCTGCAGTTTGTTTGCG-3'
3'-ACGTCCAGGGCTTTGAGACACGCCACGACTTGACCAACTGCGAGACGTCAAACAAACGCCACTG-5'
(SEQ. ID NOS. 1 and 2, respectively)
```

The third piece in the ligation was a 154-bp BstEII-HindIII fragment from pK1ZZIGF-I encoding the remaining

```
5'-CTAGAATTATGATGATTACTCTGCGCAAACTTCCTCTGGCGGTTGCCGTCGCAGCGGGCGT
                                                 AATGTCTGCTCAGGCCATGGCCA-3'
3'-TTAATACTACTAATGAGACGCGTTTGAAGGAGACCGCCAACGGCAGCGTCGCCCGCA
                                                 TTACAGACGAGTCCGGTACCGGTCTAG-5'
(SEQ. ID NOS. 3 and 4, respectively)
``` amino acids 19–70 of IGF-I. pK1ZZIGF-I is a kanamycin-resistant plasmid containing a lac promoter attached to a Protein A promoter attached to a Protein A signal, attached to two consensus Z regions from Protein A that bind IgGs and secrete proteins, fused using two codons encoding an Asn-Gly interface to a synthetic IGF-I gene and also containing an F region to give high copy number. This plasmid is similar to pZZ-IGF-I shown in FIG. 6 of and described in EP Pub. No. 230,869 published 5 Aug. 1987, where the ampicillin gene is replaced by a kanamycin gene.

The last fragment was a 291-bp HindIII-BamHI fragment from the plasmid pLS8. This last fragment is simply the

Step 3: pLS321amB

Figure 7:
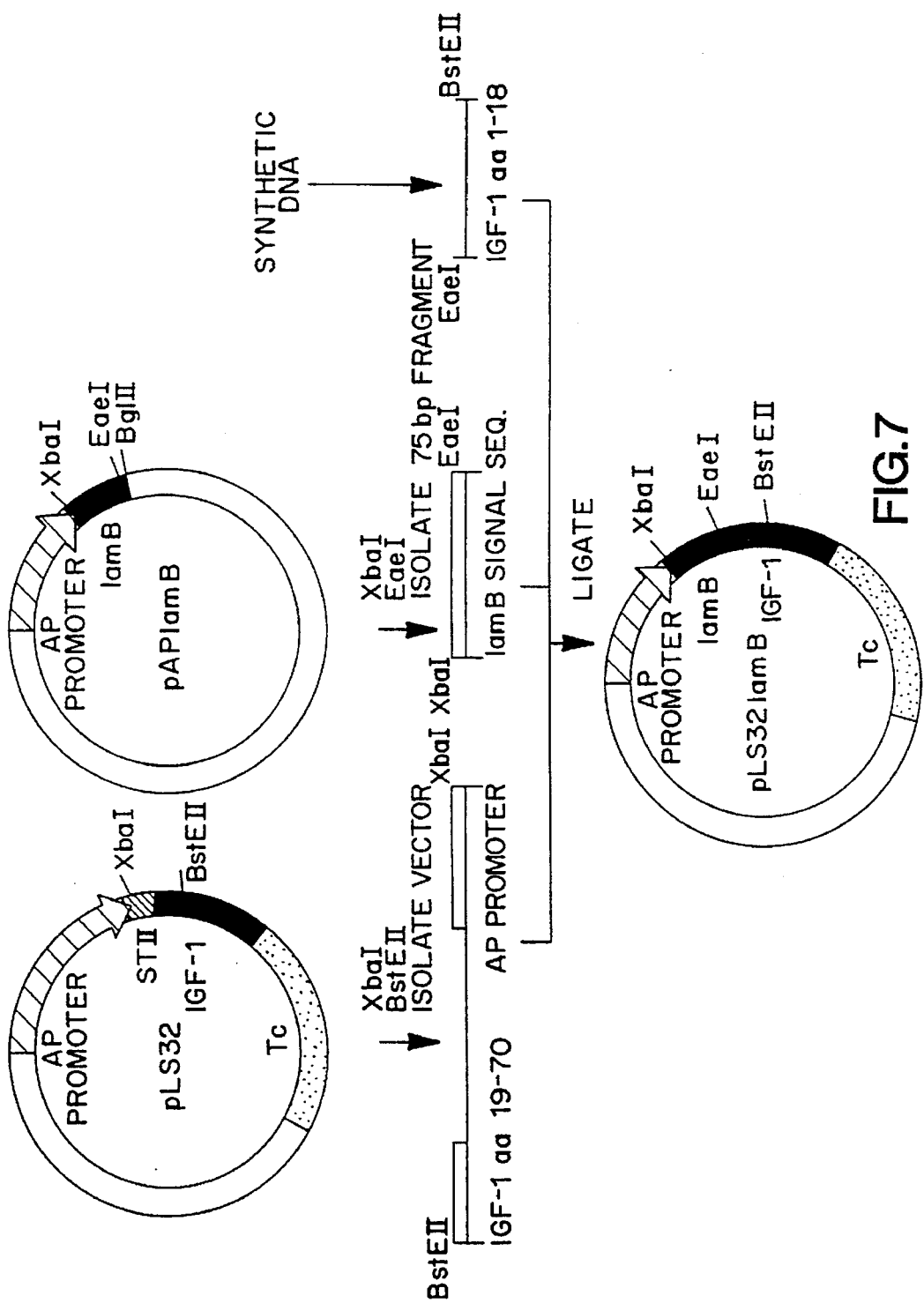
FIG. 7 depicts the construction of pLS321amB, still another intermediate plasmid in the construction of pLS32Tsc.

The plasmid pLS321amB results in the fusion of the lamB signal sequence to the IGF-I coding region and was constructed as shown in FIG. 7 by the ligation of three DNA fragments. The first of these was the vector pLS32 in which the small XbaI-BstEII fragment had been removed. The second was a 75-bp XbaI-EaeI fragment from pAP1amB encoding the lamb signal sequence. The third was a 55-bp synthetic DNA duplex encoding the first 18 amino acids of mature IGF-I, and having the following sequence:

```
5'-GGCCGGTCCCGAAACTCTGTGCGGTGCTGAACTGGTTGACGCTCTGCAGTTTGTTTGCG-3'
    3'-CCAGGGCTTTGAGACACGCCACGACTTGACCAACTGCGAGACGTCAAACAAACGCCACTG-5'
```
(SEQ. ID NOS. 5 and 6, respectively)

The following steps introduce into the plasmid the transcriptional terminator. These plasmid changes resulted in an improved product yield.

Step 4: pLS331amB

Figure 8:
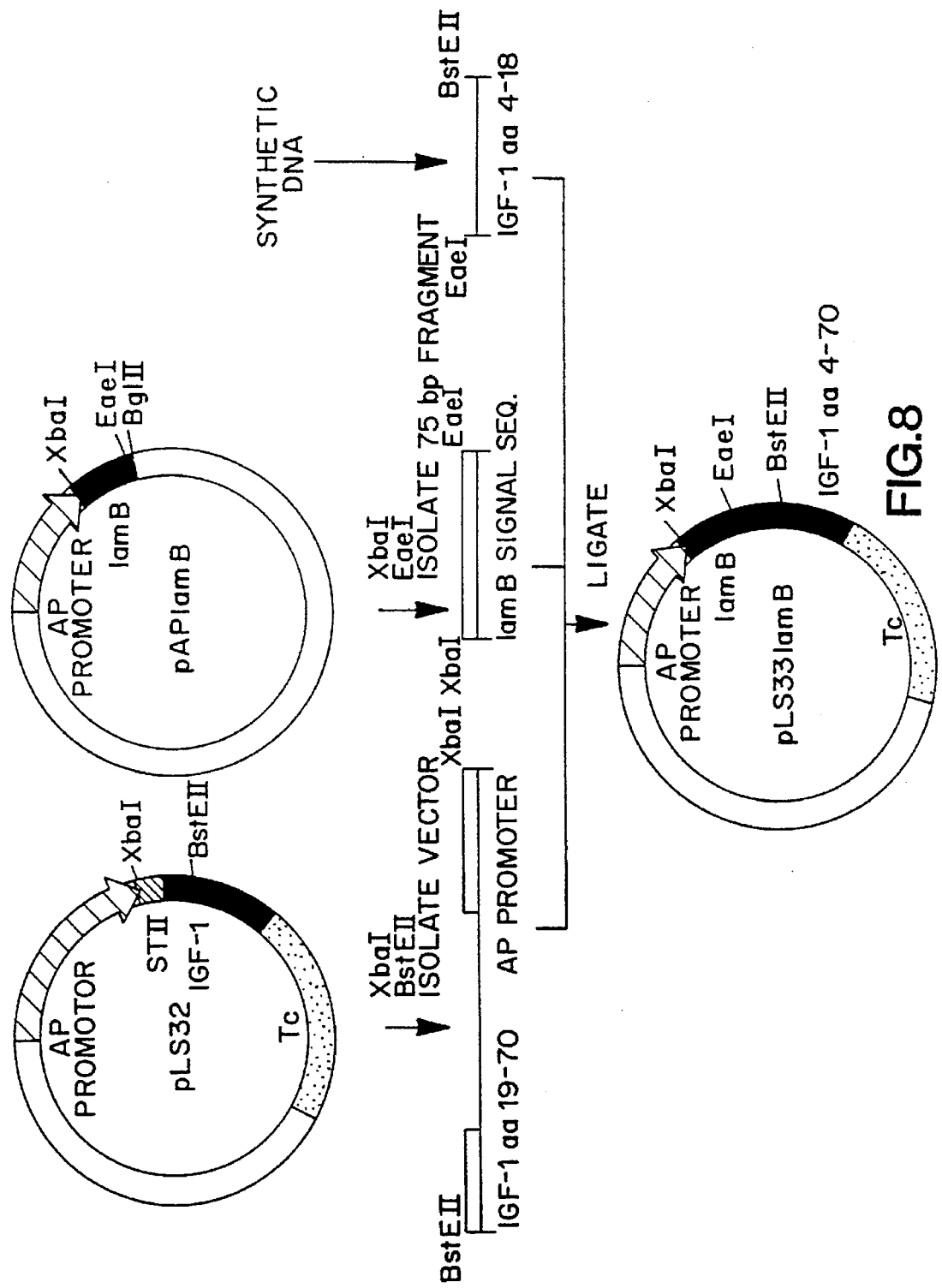
FIG. 8 depicts the construction of pLS331amB, another intermediate plasmid in the preparation of pLS32Tsc.

The plasmid pLS331amB is an intermediate in the preparation of pLS32Tsc and was constructed as shown in FIG. 8 by ligating together three DNA fragments. The first of these was the vector pLS32 in which the small XbaI-BstEII fragment had been removed. The second was a 75-bp XbaI-EaeI fragment from pAP1amB encoding the lamb signal sequence. The third was a 46-bp synthetic DNA duplex with the following sequence:

```
5'-GGCCACTCTGTGCGGTGCTGAACTGGTTGACGCTCTGCAGTTTGTTTGCG-3'
    3'-TGAGACACGCCACGACTTGACCAACTGCGAGACGTCAAACAAACGCCACTG-5'
```
(SEQ. ID NOS. 7 and 8, respectively)

The above sequence encodes amino acids 4–18 of mature IGF-I.

Step 5: pLS33Tsc

Figure 9:
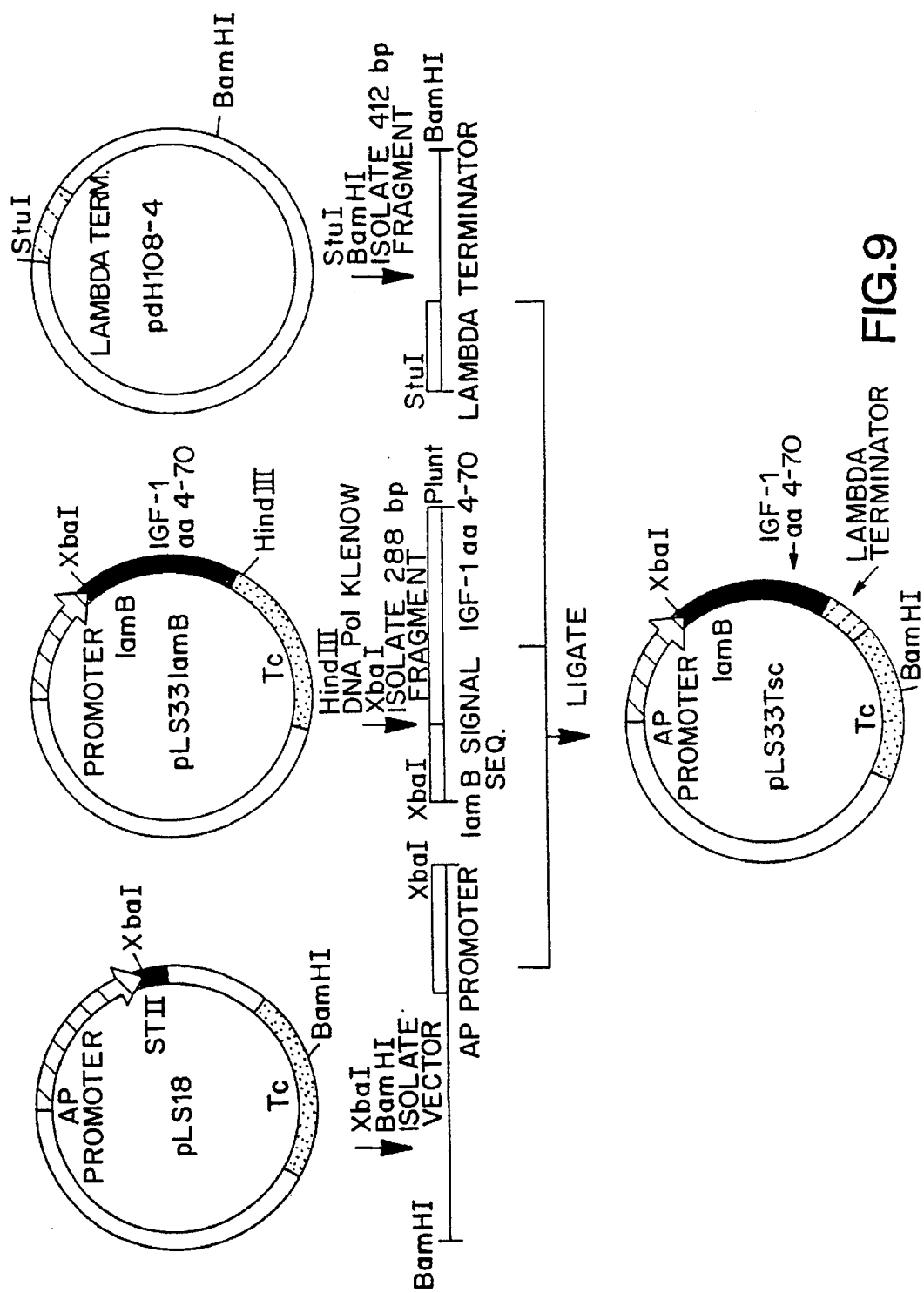
FIG. 9 depicts the construction of pLS33Tsc, another intermediate in the preparation of pLS32Tsc and of pBKIGF-2, the latter being an intermediate plasmid in preparing another expression vector used in the examples below, namely, pBKIGF-2B.

The plasmid pLS33Tsc results in the placement of the lambda to transcriptional terminator immediately downstream of the IGF-I coding sequence. Three DNA fragments were ligated together as shown in FIG. 9 to construct this plasmid. The first piece was the vector pLS18 in which the small XbaI-BamHI fragment had been removed. pLS18 is a derivative of phGH1 [Chang et al., supra]that contains DNA encoding human DNase (as disclosed in WO 90/07572 published Jul. 12, 1990) rather than hGH. phGH1 could be used to generate the same fragment. The second part of the ligation was a 288-bp XbaI-HindIII fragment from pLS331amB in which the HindIII restriction site had been blunted by treatment with DNA polymerass I (Klenow). The third part of the ligation was a 412-bp StuI-BamHI fragment from the plasmid pdH108-4. This fragment contains the lambda to transcriptional terminator [Scholtissek and Grosse, Nuc. Acids Res., 15:3185 (1987)] and base pairs 2–375 of pBR322 [Sutcliffe, supra], wherein the base pairs 2–375 are downstream or 3' of the transcriptional terminator. The sequence of the terminator region of this fragment is as follows:

```
5'-CCTAACGCTCGGTTGCCGCCGGGCGTTTTTTATTGTTAA-3'
3'-GGATTGCGAGCCAACGGCGGCCCGCAAAAAATAACAATT-5'
```
(SEQ. ID NOS. 9 and 10, respectively)

Step 6: pLS32Tsc

The final plasmid pLS32Tsc was constructed as shown in FIG. 10 by ligating together two DNA fragments. The first of these was the vector pLS33Tsc from which the small EcoRI-BstEII fragment had been removed. The second was a 550-bp EcoRI-BstEII fragment from pLS321amB containing the AP promoter, trp Shine-Dalgarno, and the coding sequence for the lamb signal sequence fused to the first 18 amino acids of IGF-I. The resulting plasmid was analyzed by restriction endonuclease digestion. The entire promoter and coding sequence was verified by DNA sequencing, with the nucleotide sequence (SEQ. ID NO. 11) and the amino acid sequence of the lamb and IGF-I protein fusion (SEQ. ID NO. 12) being given in FIG. 11.

iii. Fermentation and Recovery Procedure

A. Transformation

Competent E. coil 27C7 cells were transformed with pLS32Tsc by standard transformation techniques. Transformants were selected and purified on LB plates containing 20 mg/L tetracycline. This medium had the following composition: 10 g/L Bacto-Tryptone, 5 g/L yeast extract, 10 g/L sodium chloride, and 20 mg/L tetracycline-HCl.

One transformed colony was used to inoculate sterile LB broth containing 20 mg/L tetracycline. The flask culture was incubated at 35°–39° C. until the optical density at 550 nm reached approximately 1.0. Sterile DMSO was added to the culture to give a final concentration of DMSO of 10% (v/v). Aliguots of 1–2 mL were dispensed into sterile vials and stored at –60° C. or below.

B. Fermentation Inoculum

A 10-L fermentor inoculum was prepared by first inoculating a two-liter shake flask containing approximately 500 ml of sterile LB medium containing tetracycline with the freshly thawed 1–2 ml culture vial described above. This flask was incubated at 35°–39° C. for 8 hours and transferred into a 10-liter fermentor containing the production medium described in Section D of this Example. The 10-liter fermentor inoculum was incubated at 35°–39° C. at 50–200 rpm for about 5–8 hours, i.e., growth to 25 OD. The inoculum was then aseptically transferred to the 1000-L fermentation vessel of FIG. 12.

C. Fermentation Apparatus

Figure 12:
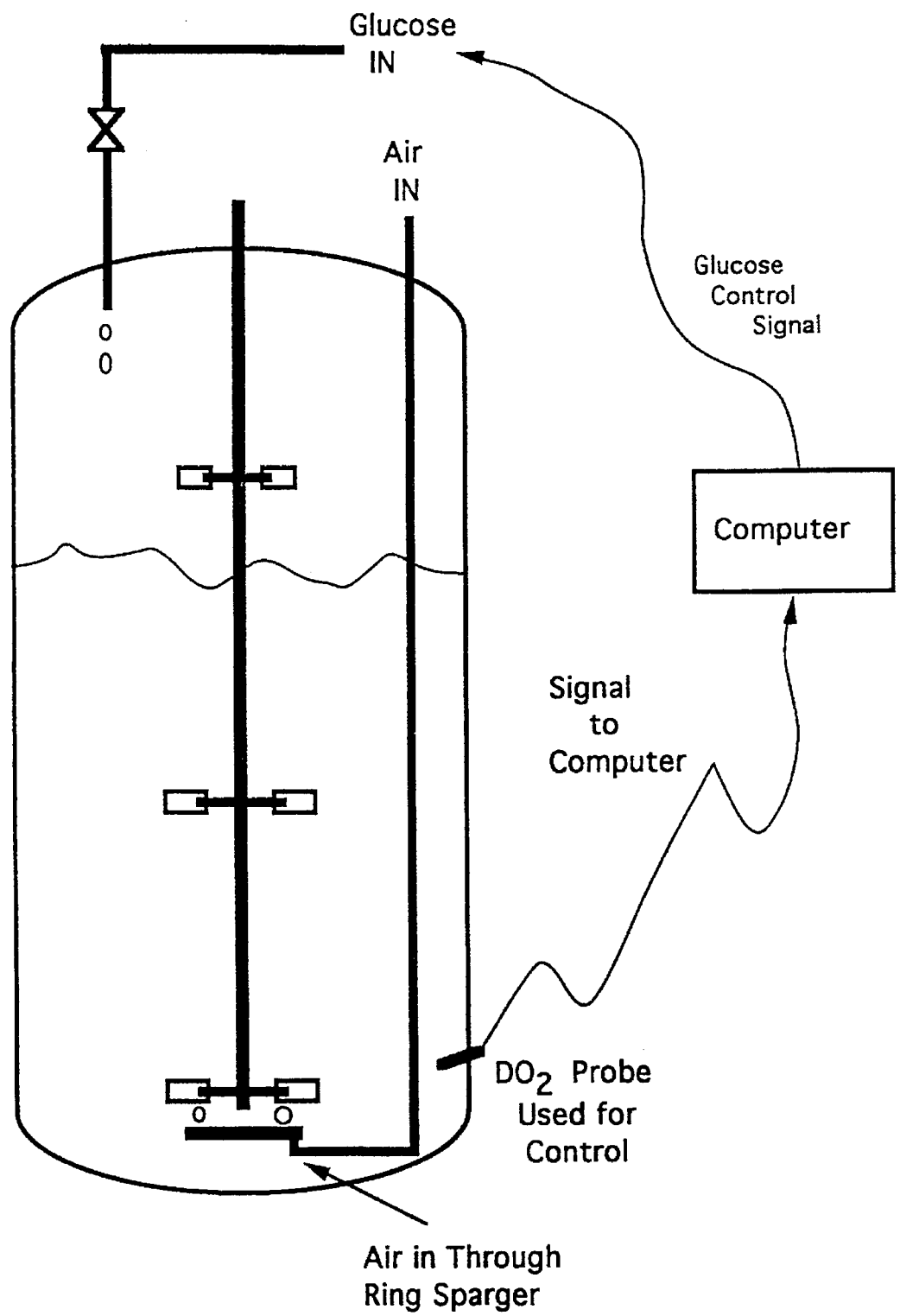
FIG. 12 is a basic diagram of the 1000-L fermentor wherein $DO_2$ instability problems occur.

FIG. 12 presents a diagram of the fermentation system used for the production of bacterially derived recombinant products at the 1000-L scale. The vessel is approximately 1500 L in total volume, with a nominal working volume (with head space) of 1000 L. The vessel is equipped with three Rushton-type impellers mounted on a vertical shaft with a top drive normally operated at 150–300 rpm. A ring air sparget is used to introduce air into the bottom of the fermentor at approximately 1000 standard liters per minute. A $DO_2$ probe mounted in the wall of the vessel near the bottom impeller measures the concentration of oxygen dissolved in the liquid (and therefore accessible to the organism). That signal is sent to a monitoring and control computer, which then regulates the glucose feed rate into the fermentor.

In this configuration, the glucose is fed into the top of the vessel to simplify sterilization of the glucose feed line. Not shown is a feed line into the top of the vessel that is used to add $NH_4OH$ on demand to control the pH of the broth. Also not shown is another feed line into the top of the vessel, which may be used for a slow feed of complex nutrients.

D. Fermentation Procedure

The 1000-L vessel initially contained 600–800 liters of fermentation medium composed as follows:

| Ingredient | Quantity/Liter |
| --- | --- |
| glucose* | 250–350 g |
| ammonium sulfate | 2–6 g |
| ammonium hydroxide | as required to control pH 7.1 to 7.5 |
| sodium phosphate, monobasic dihydrate | 1–2 g |
| potassium phosphate, dibasic | 2–3 g |
| sodium citrate, dihydrate | 0.5–1.5 g |
| potassium chloride | 1–2 g |
| 25% Pluronic Polyol L61 | 0.2 ml initially and as needed to control foaming |
| magnesium sulfate, heptahydrate | 1–3 g |
| tetracycline HCl | 5–20 mg |
| yeast extract** | 5–15 g |
| NZ amine AS** | 5–20 g |
| isoleucine | 0–10 g |
| ferric chloride, heptahydrate | 10–30 mg |
| zinc sulfate, heptahydrate | 2–5 mg |
| cobalt chloride, hexahydrate | 2–5 mg |
| sodium molybdate, dihydrate | 2–5 mg |
| cupric sulfate, pentahydrate | 2–5 mg |
| boric acid | 0.5–2 mg |
| manganese sulfate, monohydrate | 1–3 mg |

*1–5 g/L of glucose was added to the culture initially. The remainder was fed to the culture over the course of the fermentation.
**Yeast extract and NZ amine AS can be added initially and/or fed throughout the fermentation.

The fermentation process was performed at 35°–39° C. at pH 7.1–7.5. The agitation rate was set at 150–300 rpm and the aeration rate at 0.7–1.5 volumes of air per volume of culture per minute. Production of IGF-I occurred after the phosphate in the medium was depleted.

A computer algorithm used an increase in the $DO_2$ probe reading to sense when the initial charge of glucose was depleted and then fed a 50%-glucose solution to maintain the organism at a growth rate near its maximal growth rate until the $DO_2$ reading had dropped to 30% of air saturation. Then the computer regulated the glucose feed to maintain the $DO_2$ reading at 30% using a standard proportional, integral (PI) control algorithm.

After approximately 12 hours of incubation, the initial charge of phosphate was depleted. The glucose feed rate was decreased by the computer since less glucose was being used for cell synthesis and therefore a lower glucose feed rate produced the oxygen consumption rate that matched the oxygen transfer rate and kept the $DO_2$ at 30%.

iv. Results

FIG. 13 presents the glucose pump rate (FIG. 13A) and the $DO_2$ reading (FIG. 13B) as a function of time for the 1000-L fermentation of this example producing IGF-I. At 12 hours, the computer was controlling at 30% $DO_2$, but shortly thereafter, the phosphate was depleted and the glucose feed rate began to be decreased by the action of the control algorithm. As can be seen, however, this transition triggered violent fluctuations in the $DO_2$ concentration that the computer was not able to control. Even after the glucose feed rate was decreased, the instabilities continued. At approximately 16 hours, the glucose feed rate was placed under manual control to maintain a constant feed rate. The $DO_2$ concentration remained approximately constant, decreasing very slowly until it reached approximately 28%. At this point, there was a precipitous decline in the $DO_2$ concentration.

Figure 14:
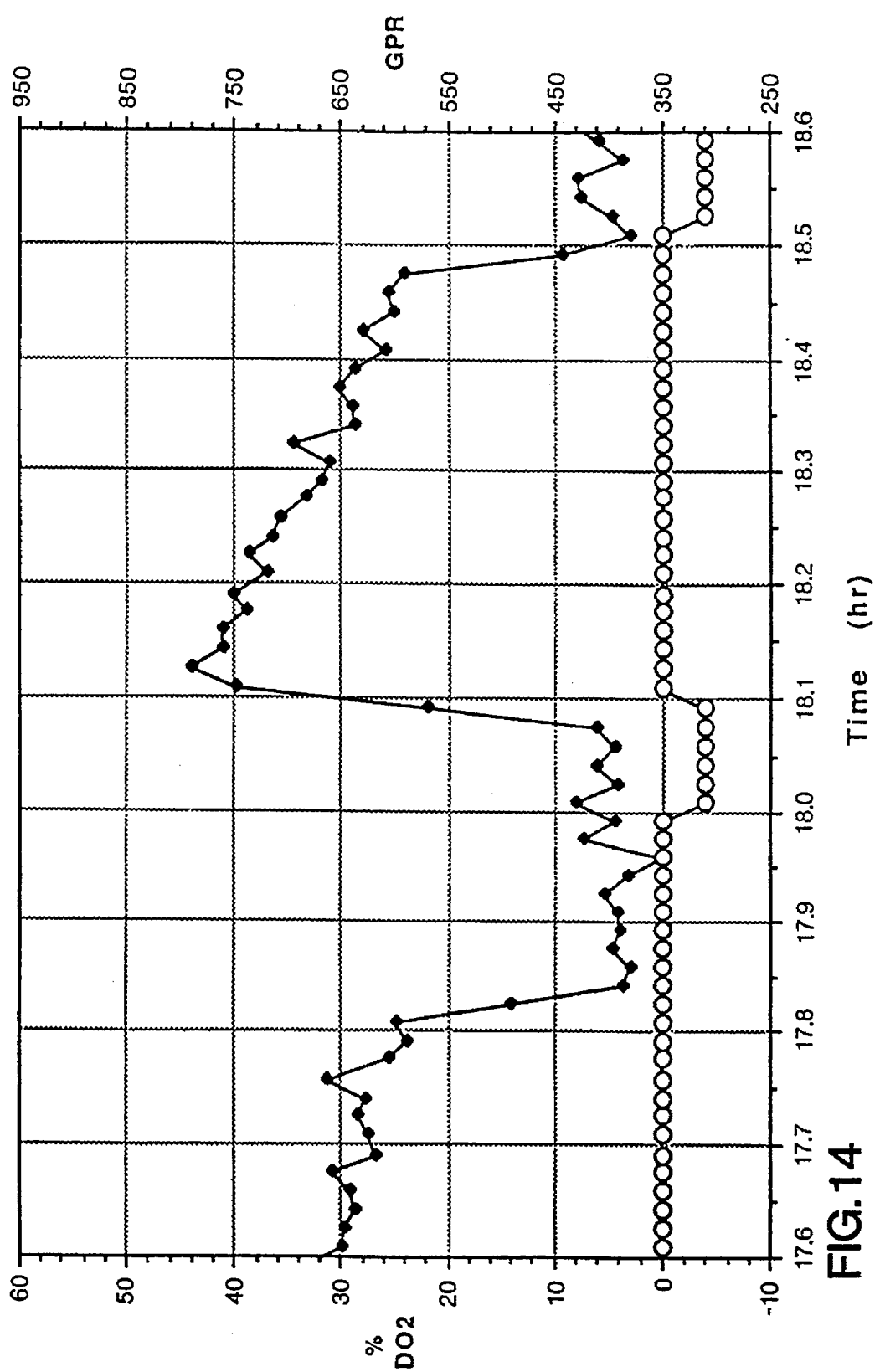
FIG. 14 illustrates the percent $DO_2$ (solid diamonds) and glucose pump rate (open circles) versus time during a 1000-L fermentation of strain 27C7 transformed with pLS32Tsc, wherein the glucose feed rate is under manual control.

Upon examination of the overall time period, there appeared to be a common pattern in the $DO_2$ record. This is displayed in more detail in FIG. 14, which presents $DO_2$ readings and glucose feed rates recorded at one-minute intervals. Even with a constant glucose feed rate, the $DO_2$ concentration fell dramatically after declining slowly to approximately 25%. In two minutes or less, the $DO_2$ concentration fell from 25% to zero.

The fermentor and its supporting equipment were examined for malfunctions that could cause such observations. None could be found.

EXAMPLE II

Figure 15:
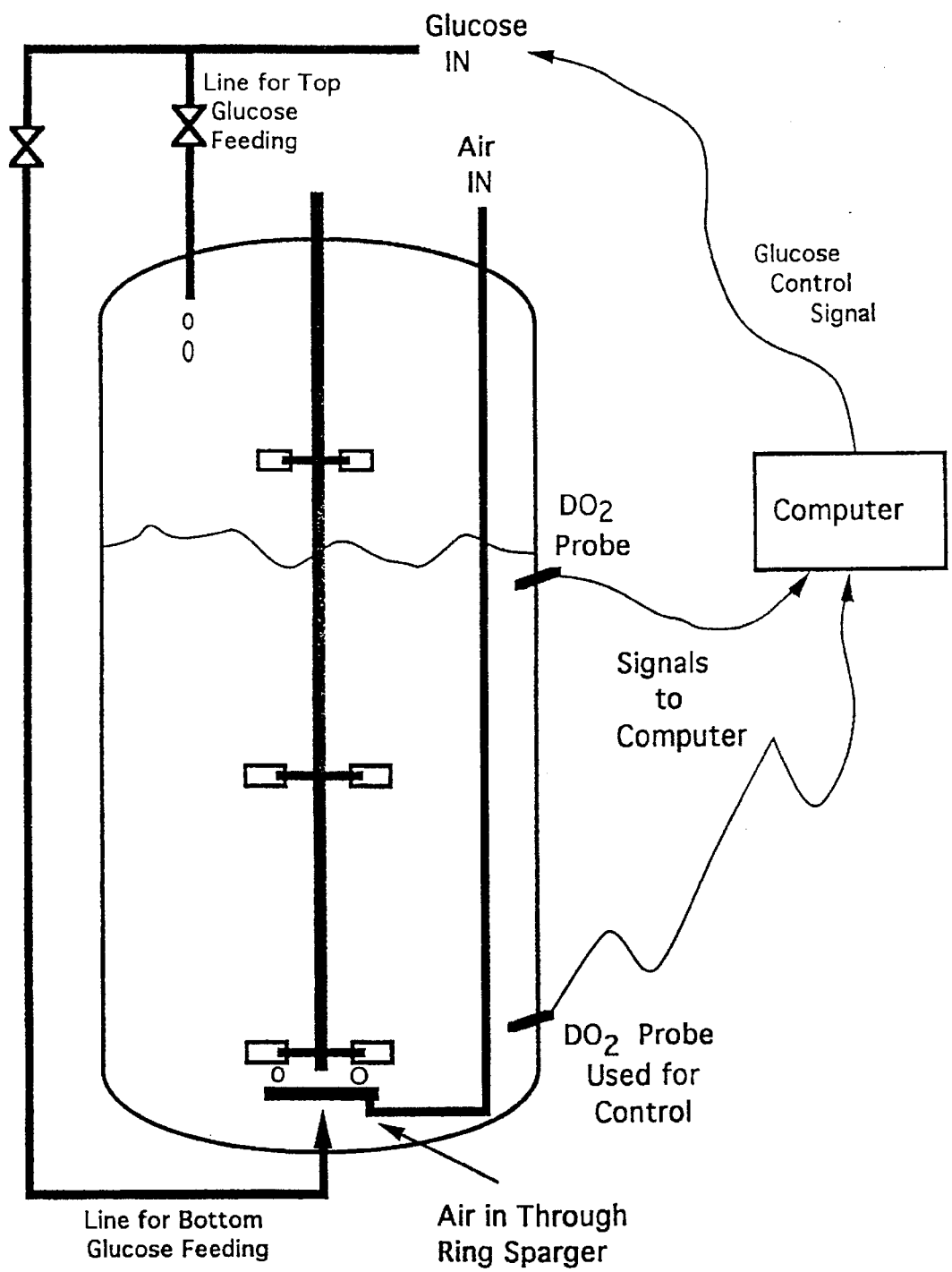
FIG. 15 is a basic diagram of the 1000-L fermentor modified to investigate $DO_2$ instability.

Use of Two $DO_2$ Probes and An Alternative Feeding Location to Study $DO_2$ Instabilities FIG. 15 presents a diagram of the 1000-L fermentor as modified to further study the $DO_2$ instabilities. A $DO_2$ probe was mounted near the top of the vessel so that it would be just immersed in the fermentation medium at the time of phosphate depletion. The glucose feed line was modified so that the glucose entry point could be changed during the fermentation from the top to the bottom of the fermentor.

The fermentation was conducted as described in Example I except that the $DO_2$ was controlled at 40% to prevent the precipitous drops in $DO_2$. Glucose was fed into the top of the vessel. After phosphate depletion, the glucose feed rate was allowed to come to its new pseudo-steady-state value, and the glucose feed rate was again placed under manual control. To test for the reproducible inducibility of the $DO_2$ instability, the glucose feed rate was then slowly increased in small increments until the $DO_2$ probe reading declined to zero. The glucose feed rate was then decreased to recover a positive, controllable $DO_2$ level.

To determine if the point of glucose addition influenced the $DO_2$ response to glucose feed increases, a second phase of the experiment was conducted. The glucose feed point was switched to the bottom of the tank and the $DO_2$ control was re-established at 40%. The glucose feed rate was again slowly increased in increments until the $DO_2$ reached zero. The glucose feed rate was again decreased so that the $DO_2$ level recovered. This entire sequence was then repeated.

Figure 16:
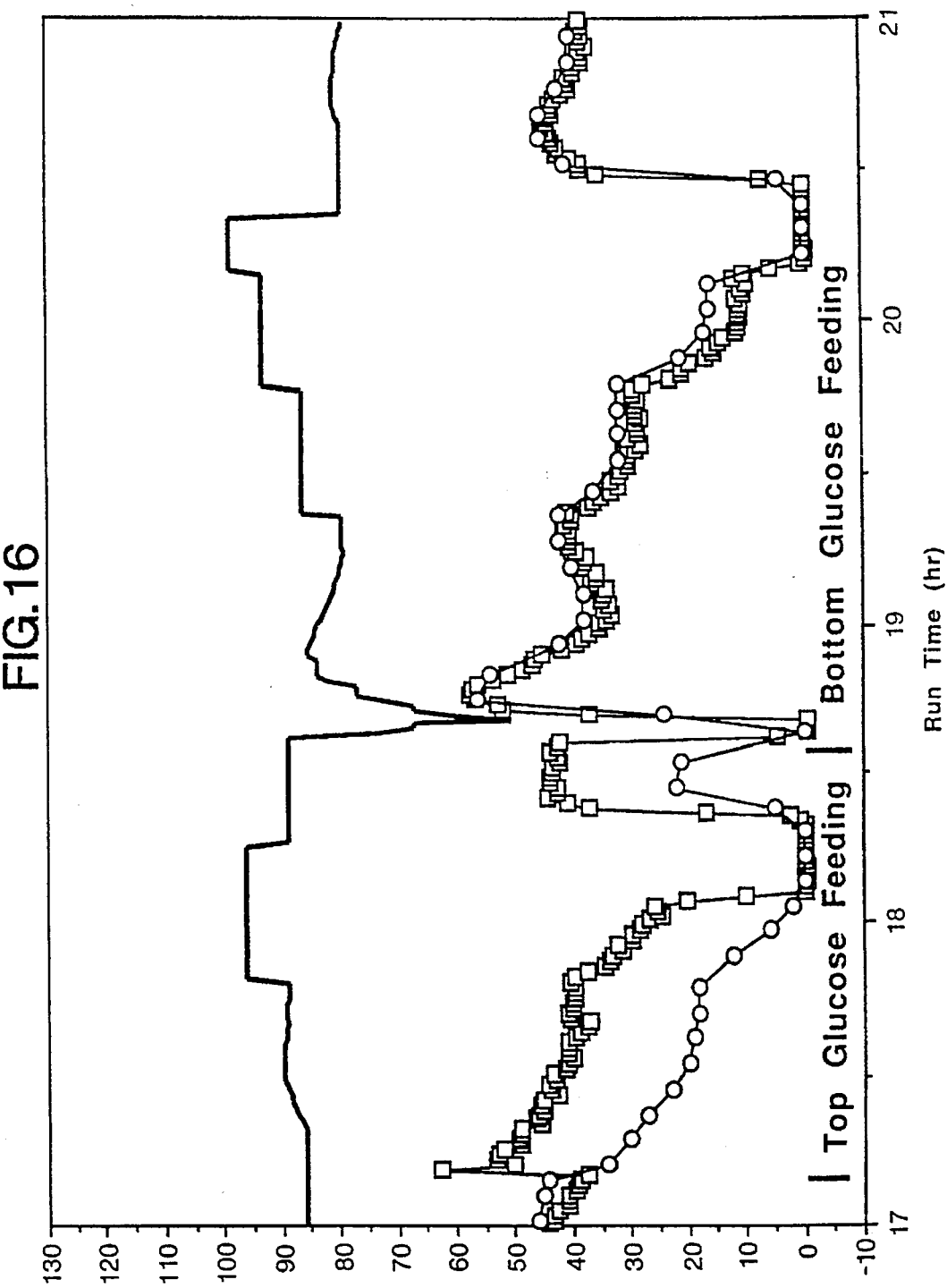
FIG. 16 illustrates an analysis of $DO_2$ instability vs. time in the 1000-L fermentor of strain 27C7 transformed with pLS32Tsc, wherein top and bottom glucose feeding are utilized. % $DO_2$ in the bottom of the vessel is represented by squares, % $DO_2$ in the top of the vessel is represented by circles, and glucose pump rate/3 (g/min) is represented by a solid line.

FIG. 16 shows the results obtained from the repeated set of cycles. The results from the first set of cycles were similar, suggesting reproducible inducibility of the $DO_2$ instability. First, the $DO_2$ was brought under control at a 40% set point (according to the bottom $D_2$ probe) with the glucose fed into the top of the fermentor. The glucose feed rate was then placed under manual control and the feed rate was increased by 8%.

In a homogeneous reactor, this sequence of events would elicit an 8% increase in oxygen uptake rate, which in turn would require an 8% increase in oxygen driving to transfer the required oxygen from the gas phase to the liquid phase. Since a 1-bar overpressure was being applied to the fermentor and since the hydrostatic liquid head exerts an estimated additional 0.2 bar pressure, a simple calculation suggests that an 8% increase in oxygen concentration driving force would be obtained by a decrease in the $DO_2$ concentration from 40% to approximately 26%.

The bottom $DO_2$ reading does indeed decrease from 40% to approximately 25% where a new equilibrium would be expected. However, at this point, the bottom $DO_2$ reading plummeted to zero. This reproduced the observation made on the run described in Example I. Importantly, throughout most of the sequence, the top $DO_2$ probe reading was more than 20% lower than the bottom probe reading. This indicates significant heterogeneity in $DO_2$ concentrations throughout the fermentation broth volume. For approximately 15 minutes after the glucose feed rate increase, the top probe reading decreased at approximately the same rate as the bottom probe reading. It was when the top probe reading reached zero that the precipitous decline in the bottom probe reading was triggered.

When glucose was fed into the bottom of the vessel, the agreement between the top and bottom probe readings suggested much less $DO_2$ heterogeneity. Again, control was established at 40% $DO_2$ according to the bottom $DO_2$ probe and the glucose feed rate was increased by 8%. This time a new steady state was achieved at approximately the predicted $DO_2$ reading. When the glucose feed rate was increased another 8%, the $DO_2$ readings again decreased and stabilized at approximately the predicted value. Apparently stable operation was established at approximately 10% $DO_2$. Finally, a further 5% increase in glucose feed rate drove the $DO_2$ readings to zero as would be predicted from the oxygen utilization and oxygen driving force calculations.

These results suggest that the $DO_2$ instabilities depicted in FIG. 13 can be prevented by providing homogeneous dissolved oxygen concentrations throughout the vessel. In this particular fermentor, feeding glucose into the bottom of the fermentor significantly improved the $DO_2$ homogeneity. In larger and/or more complex fermentors (for example, fermentors with cooling coils), $DO_2$ homogeneity will be much more difficult to achieve.

The results also suggest that the $DO_2$ instability events (observed while monitoring the $DO_2$ at the bottom of the fermentor) are coincident with the depletion of the measurable $DO_2$ concentration at the top of the fermentation broth. These results suggest either a complicated and very rapid hydrodynamic phenomenon or a sudden biological event triggered by very low $DO_2$ concentrations that increased the overall oxygen utilization rate.

EXAMPLE III

Reproducing $DO_2$ Instabilities in a Modified 10-L Fermentor

Although the results of Example II were quite informative, experiments at the 1000-L scale are difficult and expensive. Therefore, it was desired to develop methods that produce the $DO_2$ instability phenomena in a bench-scale, 10-L working-volume fermentor.

i. Fermentor

FIG. 1 shows a diagram of the modified 10-L fermentor used herein. Normally, the fermentor would utilize three Rushton-type impellers. In this modified configuration, the top impeller is removed and the fermentor is operated with a relatively high liquid volume. This produces a large poorly mixed region at the top of the fermentation broth. Glucose is fed into the top of the fermentor 17 to mimic the large-scale configuration and to further contribute to $DO_2$ heterogeneity. Finally, a redox probe 15 is installed in addition to the normal polarographic $DO_2$ probe 13. As will be seen, this provides information about the culture when the $DO_2$ probe reading is at or near zero.

ii. Host Organism

The host organism used was the same as that used in Example I (27C7) except for having a rbs7 deletion (ribose utilization minus) and having a restored ilvG locus. Both markers were introduced by P1 transduction. The organism is designated 37D6.

iii. Description/Construction of IGF-I Expression Plasmid PBKIGF-2B

In the IGF-I-expressing plasmid pBKIGF-2B, the transcriptional and translational sequences required for expression of the IGF-I gene in E. coli are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamb signal sequence or alternatively by the STII signal sequence. The majority of rhIGF-I is found in the cell periplasmic space. Plasmid pBKIGF-2B confers tetracycline resistance upon the transformed host.

Plasmid pBKIGF-2B was constructed in several steps using as intermediate plasmids pLS32Tsc, pLBIGFTsc, pLS33Tsc, and pRanTsc.

Step 1: DLS32Tsc

This plasmid was constructed as described in Example I.

Step 2: pLBIGFTsc

Step a: pLamBIGF

Figure 17:
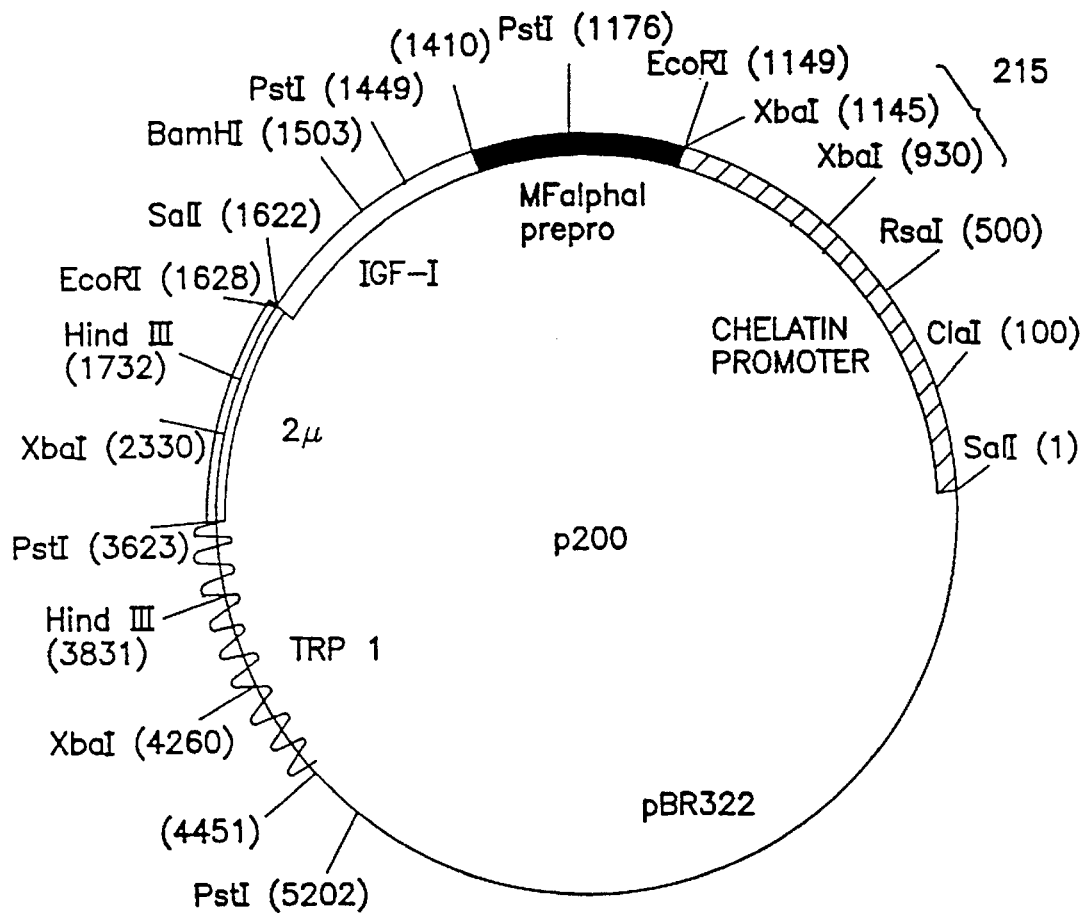
FIG. 17 shows a restriction map for plasmid p200, used to produce pLamBIGF, an intermediate plasmid in the production of pLBIGFTsc, used to prepare pBKIGF-2.

For the first part of the ligation, the EcoRI-PstI vector fragment from pBR322 was isolated. For the second part of the ligation, a PstI-NcoI 1244-bp fragment was isolated from pAPLamB. For the third part of the ligation, the HaeII-EcoRI 196-bp fragment containing the IGF-I gene except the initial 5' end was isolated from plasmid p200. p200 is a pBR322-derived plasmid having, in the 5' to 3' order, the chelatin promoter, the MF alpha I prepro signal sequence, DNA encoding mature IGF-I, and the 2-micron terminator. It contains the ColE1 origin of replication for bacteria and the 2-micron origin for yeast. A restriction enzyme plasmid diagram of p200 is provided in FIG. 17. The nucleotide sequence (SEQ. ID NO. 13) of the EcoRI (starting at position 1149) to EcoRI (starting at position 1628) fragment of p200 containing the MF alpha I prepro and IGF-I gene is provided in FIG. 18. The HaeII, PstI, BamHI, and SalI restriction sites that are also in the diagram in FIG. 17 are indicated in the sequence by underlining. A piece of synthetic DNA linking the signal sequence to the IGF-I gene (NcoI to HaeII) was prepared having the following sequence:

```
5'-CATG GCC GGT CCG GAA ACT CTG TGC GGC GC   (SEQ. ID NO. 14)
3'-     CGG CCA GGC CTT TGA GAC ACG C        (SEQ. ID NO. 15).
```

Figure 19:
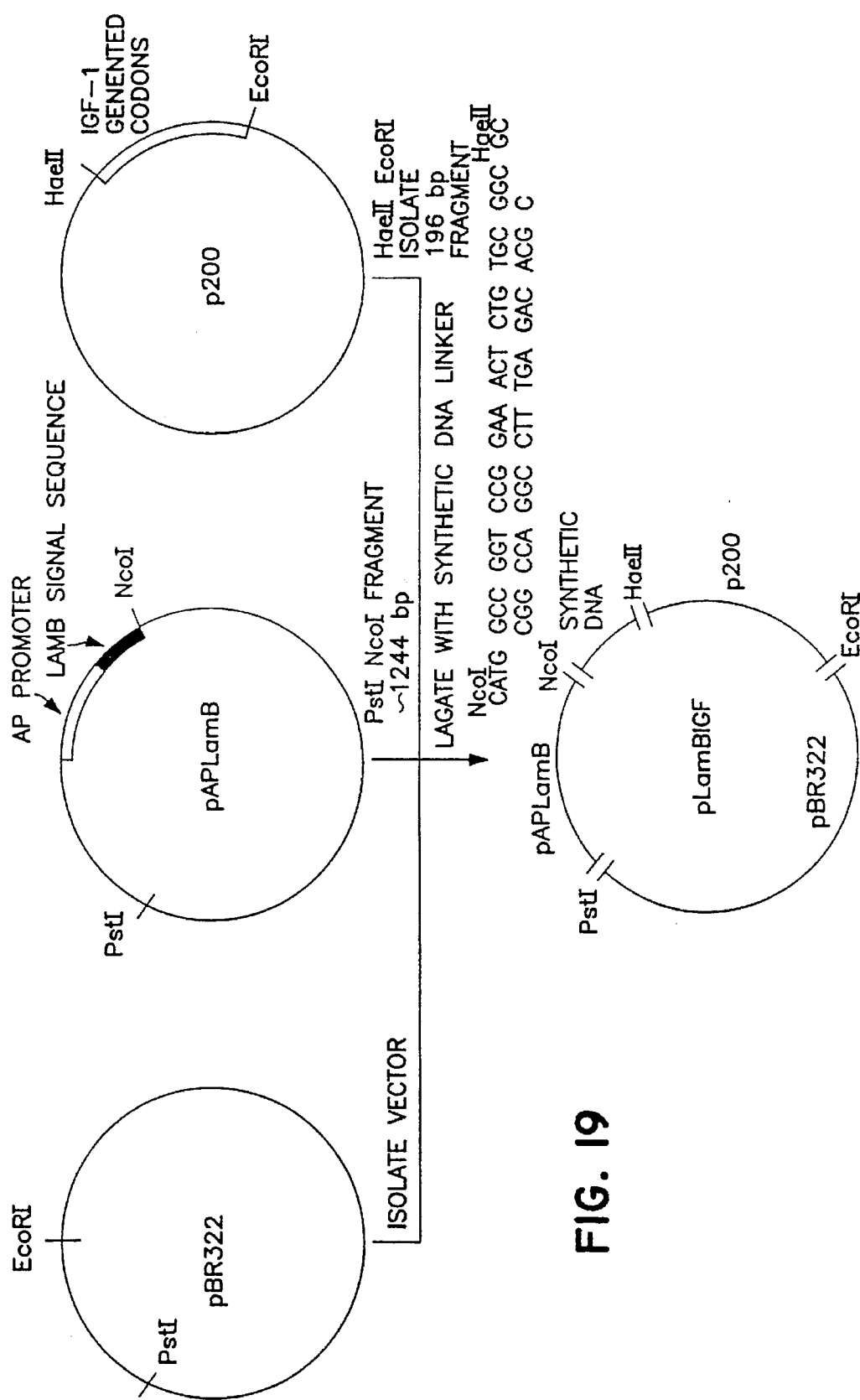
FIG. 19 depicts the construction of pLamBIGF from three plasmid fragments and a piece of synthetic DNA (SEQ. ID NOS. 14 and 15). pLamBIGF is an intermediate plasmid in the production of pLBIGFTsc, used to prepare pBKIGF-2.

The three plasmid fragments and the synthetic DNA were ligated together to form pLamBIGF, as shown in FIG. 19.

Step b: pLBIGFTsc

Figure 20:
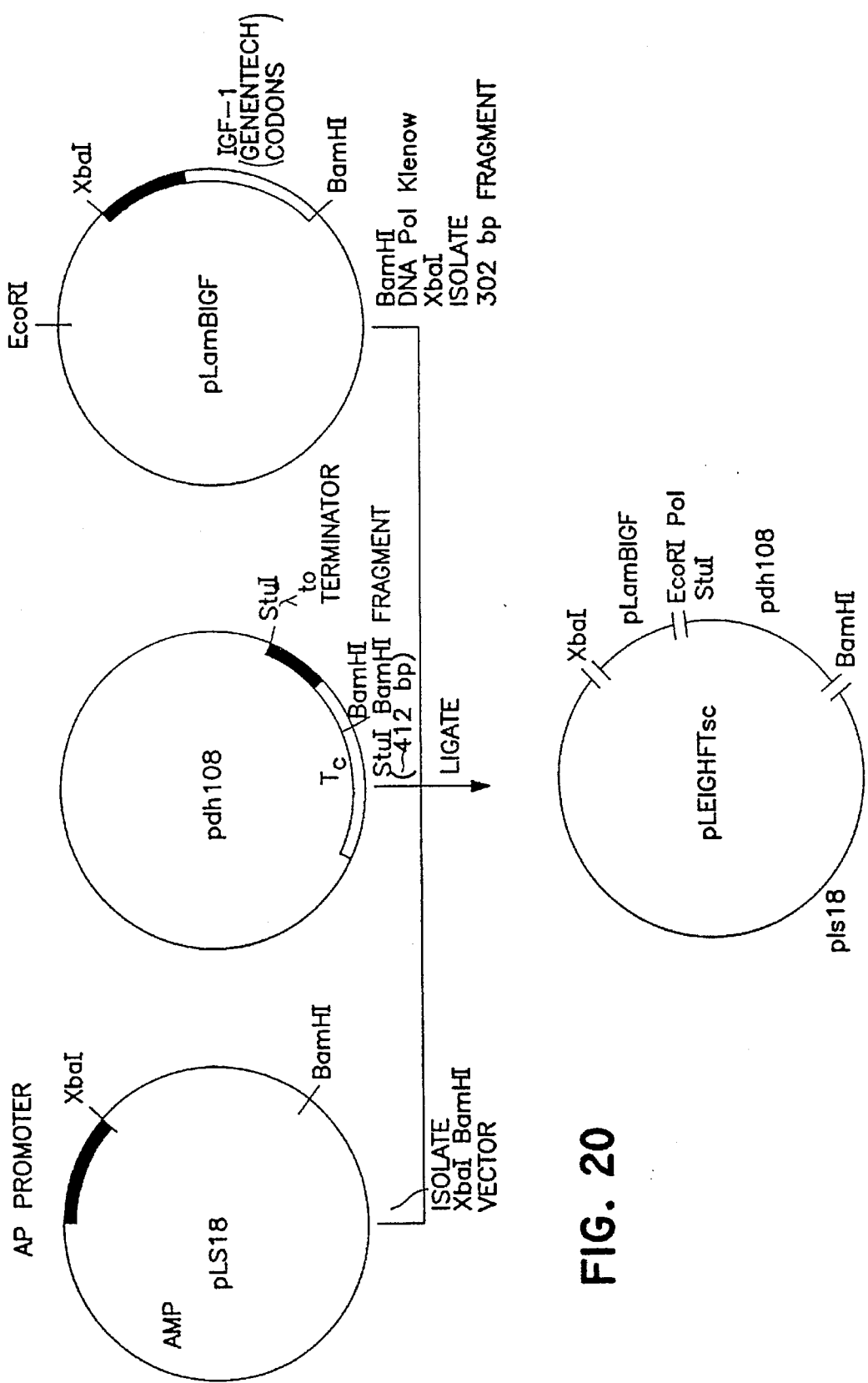
FIG. 20 depicts the construction of the intermediate plasmid pLBIGFTsc from pLamBIGF.

The XbaI-BamHI vector fragment was isolated from pLS18 as the first ligation fragment. The second part of the ligation was a 412-bp StuI-BamHI fragment from the plasmid pdH108-4 described above. The third part of the ligation was prepared by an EcoRI digest of pLamBIGF, followed by treatment with DNA polymerase Klenow fragment, followed by a XbaI digest. The resultant 302-bp fragment was isolated. These three fragments were ligated to yield pLBIGFTsc, as shown in FIG. 20.

Step 3: pRanTsc

Figure 21:
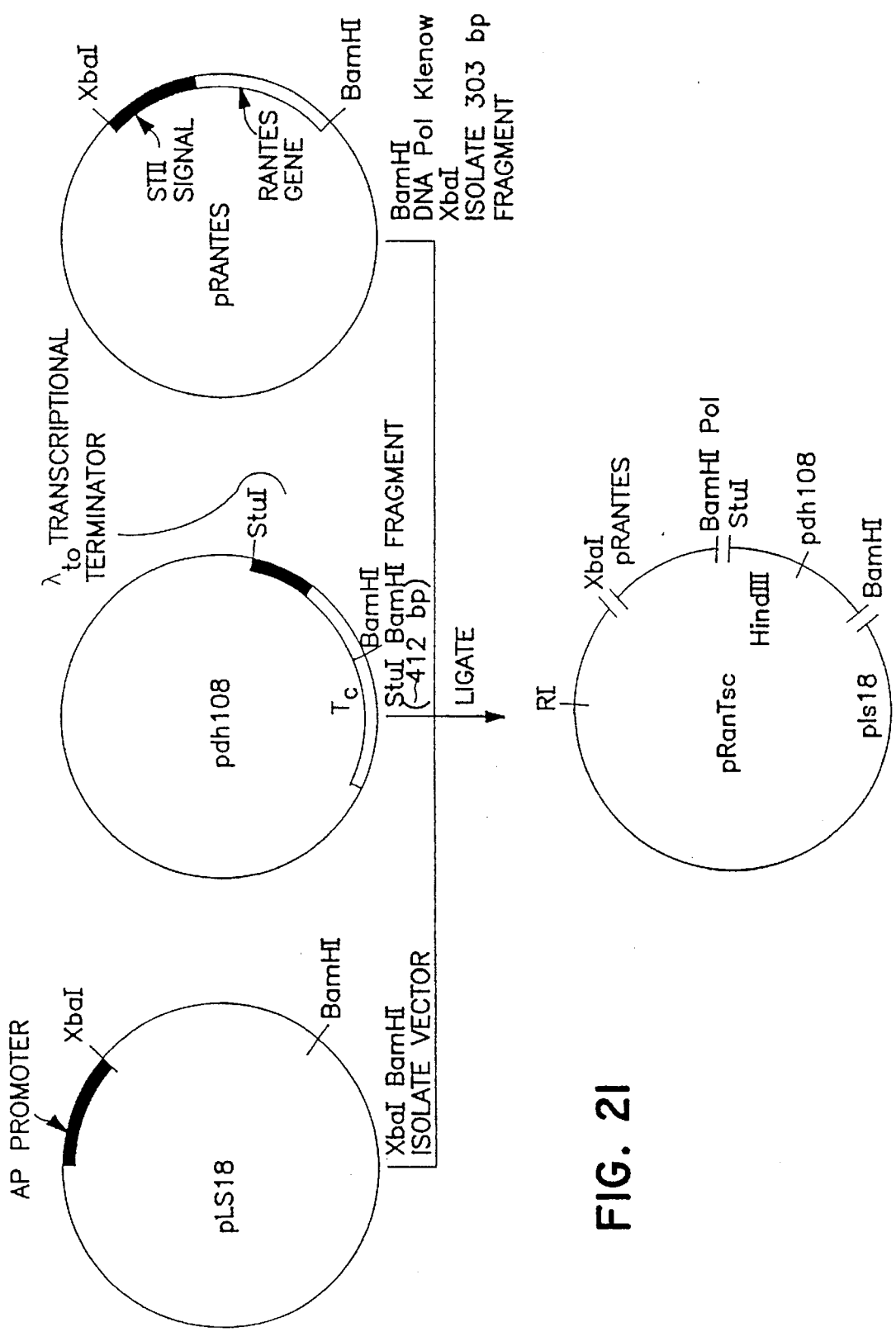
FIG. 21 depicts the construction of the intermediate plasmid pRanTsc used in the production of pBKIGF-2.

The XbaI-BamHI vector fragment from pLS18 was isolated as the first ligation fragment. The second part of the ligation was a 412-bp StuI-BamHI fragment from the plasmid pdH108-4 described above. The third part of the ligation was prepared from pRANTES. pRANTES is a pBR322-based plasmid containing a fragment of a XbaI linker followed by the STII signal, followed by the cDNA encoding RANTES [as published by Schall et al., *J. Immunol.*, 141: 1018 (1988)], followed by the BamHI linker. The third fragment was prepared by digestion of pRANTES with BamHI, followed by treatment with DNA polymerass Klenow fragment, followed by a XbaI digest. The resultant 303-bp fragment was isolated. These three fragments were ligated to yield pRanTsc, as shown in FIG. 21.

Step 4: pBKIGF-2

Figure 22:
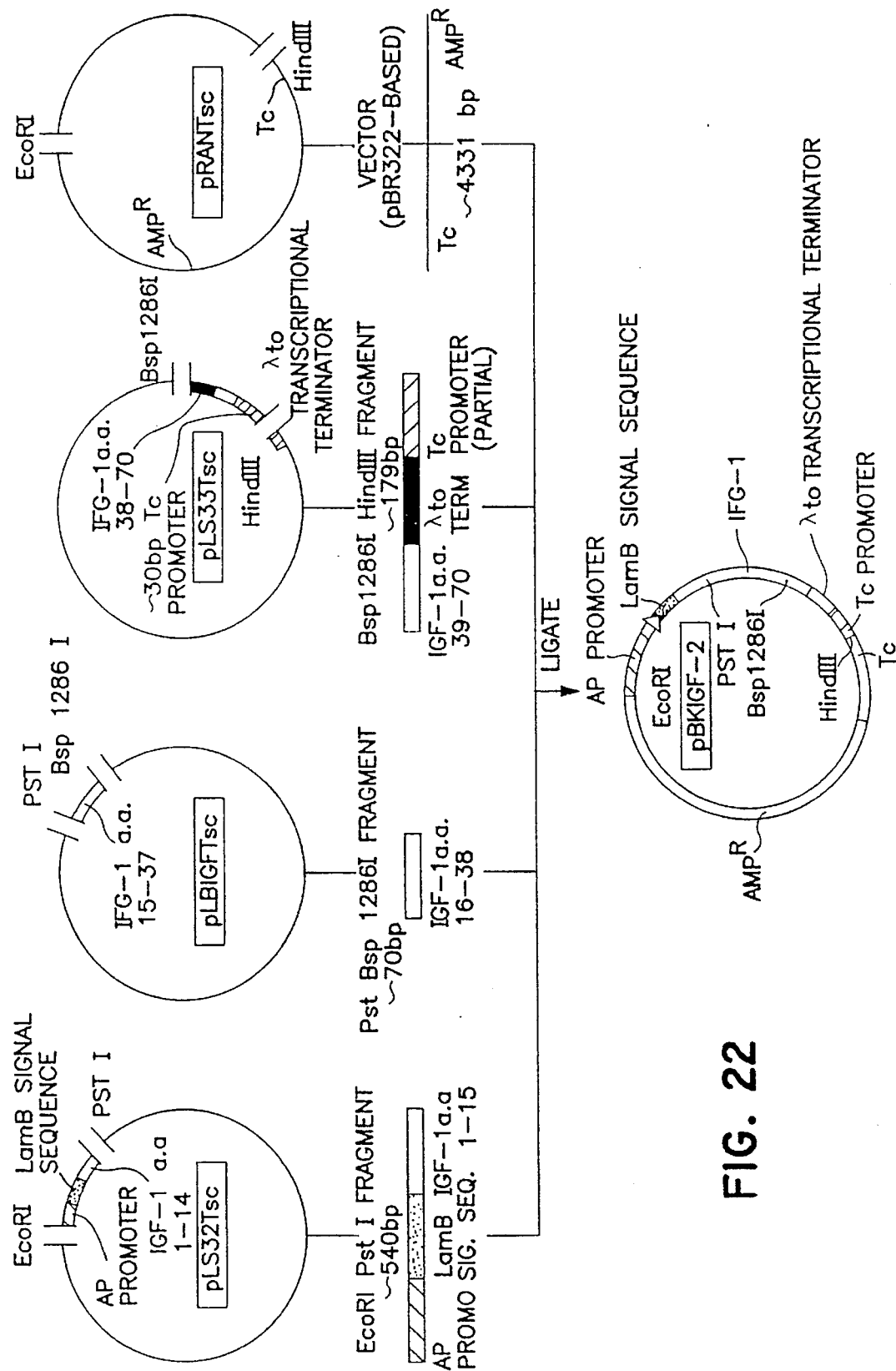
FIG. 22 depicts the construction of pBKIGF-2 from pLS32Tsc, pLBIGFTsc, pLS33Tsc, and pRanTsc.

As shown in FIG. 22, the EcoRI-PstI 540-bp fragment containing the alkaline phosphatase promoter, the lamb signal sequence, and DNA encoding the first 15 amino acids of IGF-I was excised from pLS32Tsc. The Pst-Bsp1286I fragment (~70 bp) containing DNA encoding amino acids 16-38 of IGF-I was excised from pLBIGFTsc. The Bsp1286I-HindIII (~179-bp) fragment containing DNA encoding amino acids 39-70 of IGF-I, the lambda terminator, and the Tc promoter was excised from pLS33Tsc. Finally, the EcoRI-HindIII ~4331-bp vector fragment (pBR322-based) was excised from pRanTsc. These third fragment was a piece of synthetic DNA to link RANTES gens with the signal sequence from NcoI to BsaJI. This synthetic DNA has the sequence:

```
NcoI                    BsaJI
5'-CATGGCCTCCCCATATTC-3'
   3'-CGGAGGGGTATAAGGAGC-5'
(SEQ. ID NOS. 18 and 19, respectively).
```

Figure 24:
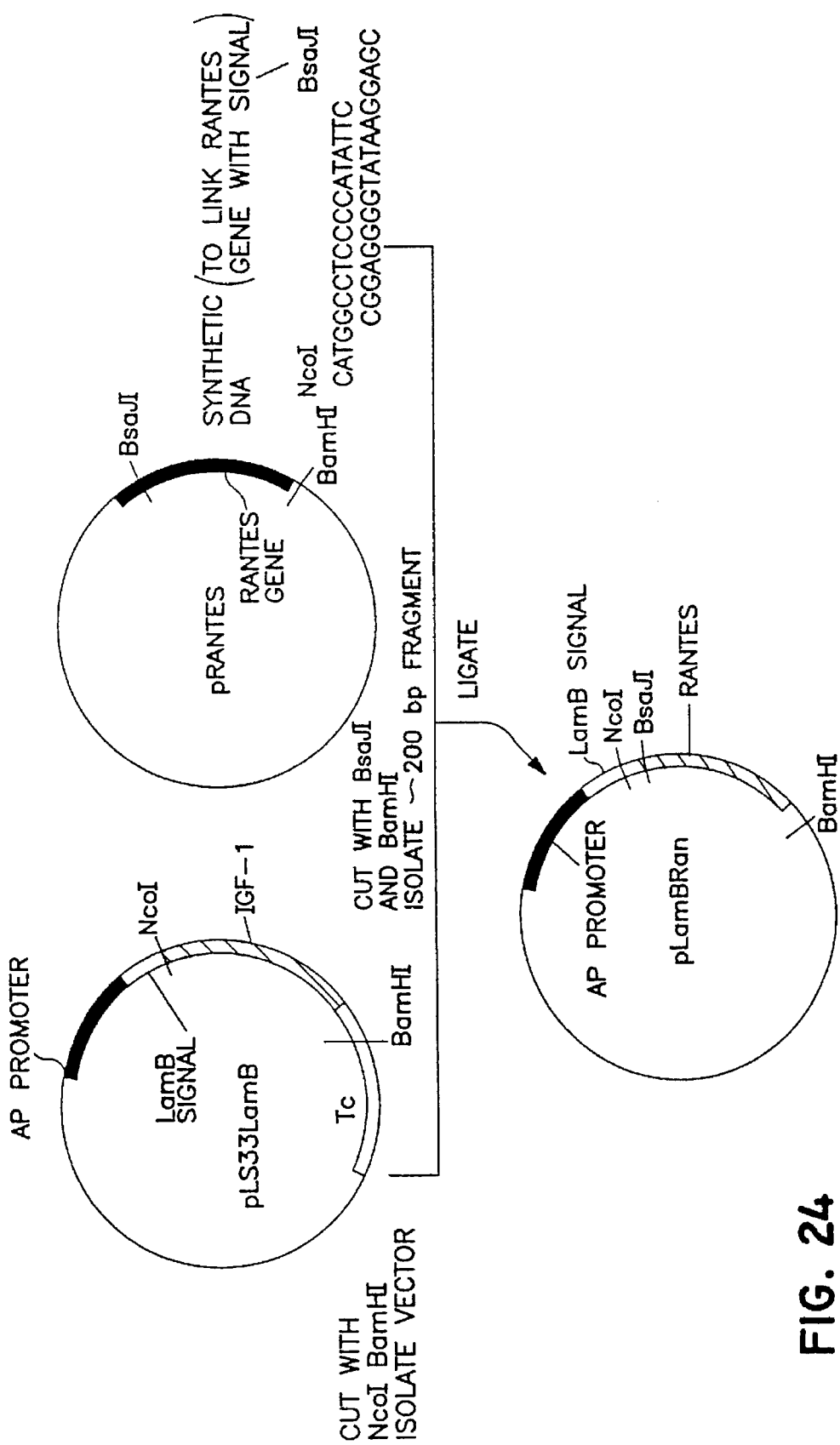
FIG. 24 depicts the construction of pLamBRan, used to prepare pBKIGF-2B, from pLS33LamB, pRANTES and a piece of synthetic DNA (SEQ. ID NOS. 18 and 19).

The resulting vector was named pLamBRan, and its construction is shown in FIG. 24.

Step 7: pBKIGF-2B

Figure 25:
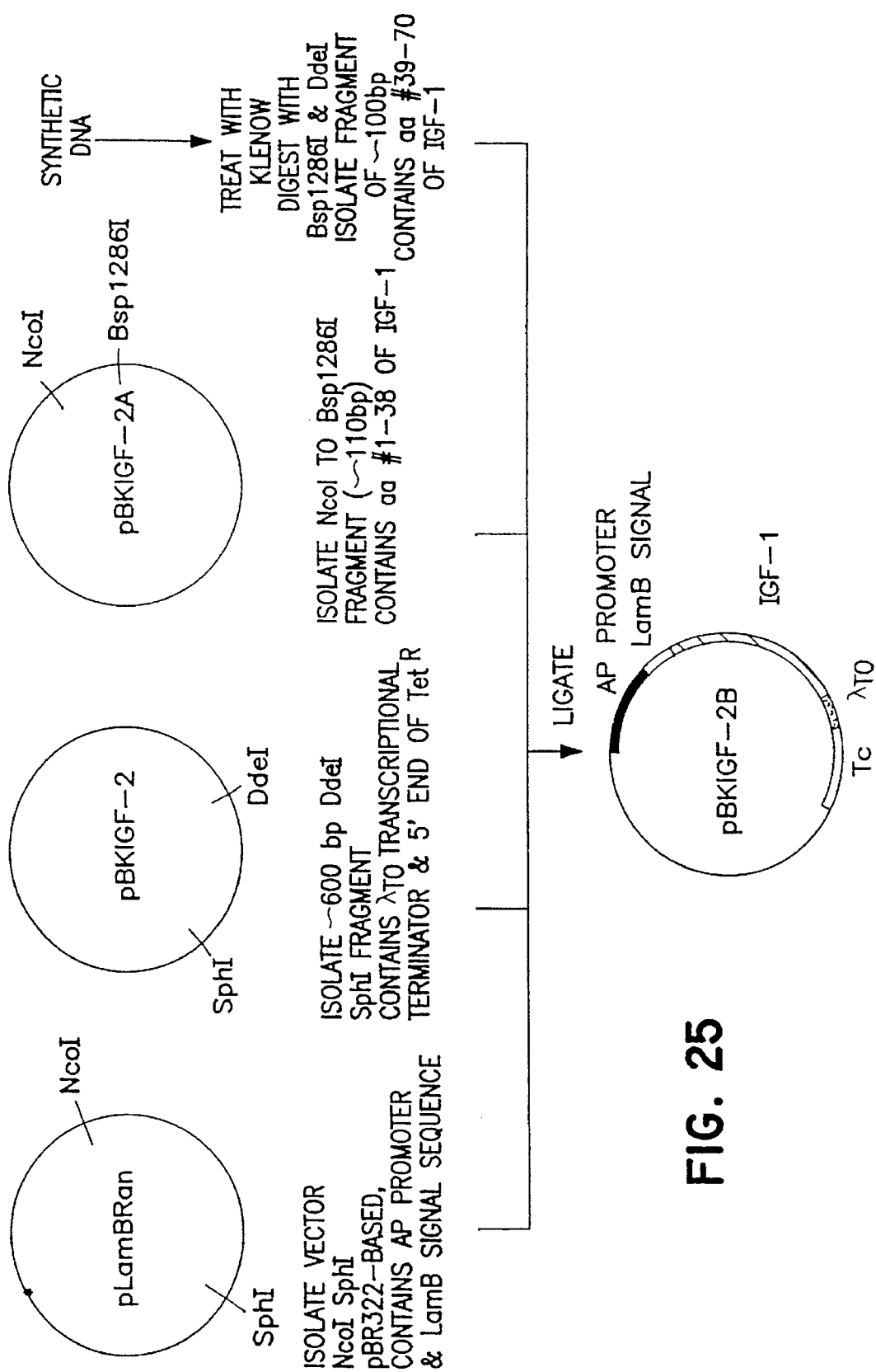
FIG. 25 depicts the construction of expression vector pBKIGF-2B from pBKIGF-2, pBKIGF-2A, pLamBRan, and a piece of synthetic DNA (SEQ. ID NOS. 20 and 21).

The construction of this plasmid is shown in FIG. 25. pLamBRan was digested with NcoI and SphI and the vector fragment was isolated containing the promoter and signal sequence. pBKIGF-2 was digested with DdeI and SphI and the ~600-bp fragment was isolated containing the lambda transcriptional terminator and the 5' end of the Tet$^R$ gene. pBKIGF-2A was digested with NcoI and Bsp1286I and the ~110-bp fragment was isolated containing the DNA encoding amino acids 1-38 of IGF-I. These three fragments were ligated together with synthetic DNA encoding amino acids 39-70 of IGF-I to yield pBKIGF-2B. This synthetic linker has the sequence:

```
5'-TCGTCGTGCTCCCCAG ACT GGT ATT GTT GAC GAA TGC TGC TTT CGT TCT TGC GAC CTG CGT CGT CTG-3'
(SEQ. ID NO. 20)

3-'AGA ACG CTG GAC GCA GCA GAC CTT TAC ATA ACG CGA

GGG GAC TTT GGG CGATTTAGACGAATCTTCGAGG-5'
(SEQ. ID NO. 21)
``` four fragments were ligated to give pBKIGF-2, which contains the AP promoter, the lamb signal sequence, the DNA encoding the entire IGF-I protein, the transcriptional terminator, the Tc promoter, and the tetracycline and ampicillin resistance markers.

Step 5: pBKIGF-2A pBKIGF-2 was digested with PstI and ClaI and the ~245-bp fragment was isolated. This contains amino acids 16-70 of IGF-I and the lambda $T_o$ terminator. pLBIGFTsc was digested with NcoI and ClaI and the vector fragment was isolated. This vector fragment contains the AP promoter, the lamb signal, and the Tet$^r$ gene. These two fragments were liSated to a piece of synthetic DNA that replaces the 5' end of IGF-I DNA from NcoI to PstI with synthetically derived codohs as follows:

iv. Transformation and Fermentation

The strain 37D6 described above was transformed with pBKIGF-2B using standard transformation techniques. Then it was grown in the same manner as described in Example I except that after the 500-ml LB medium culture was used to inoculate the 10-L fermentor, the fermentation was conducted as described for the 1000-L fermentor. In addition, the mineral salts were reduced to 60% of the concentration used in the 1000-L fermentation. This resulted in the phosphate being depleted approximately two hours sooner in the modified 10-L fermentor as compared to the 1000-L fermentor.

Finally, a complex nitrogen feed was initiated at 40 OD (A550) to provide a slowly fed source of amino acids and phosphate after the depletion of the amino acids and phosphate initially charged into the fermentor. This feed consisted of 290 ml of 20% NZ Amine AS mixed with 140 ml of 20% yeast extract and was fed at a rate of 0.4 ml/min. The initial starting volume after inoculum addition was approximately 8 L.

```
5'-CATGGCC GGT CCC GAA ACT CTG TGC GGT GCT GAA CTG GTT GAC GCT CTG CA-3'
3'-        CGG CCA GGG CTT TGA GAC ACG CCA CGA CTT GAC CAA CTG CGA G-5'
(SEQ. ID NOS. 16 and 17, respectively).
```

Figure 23:
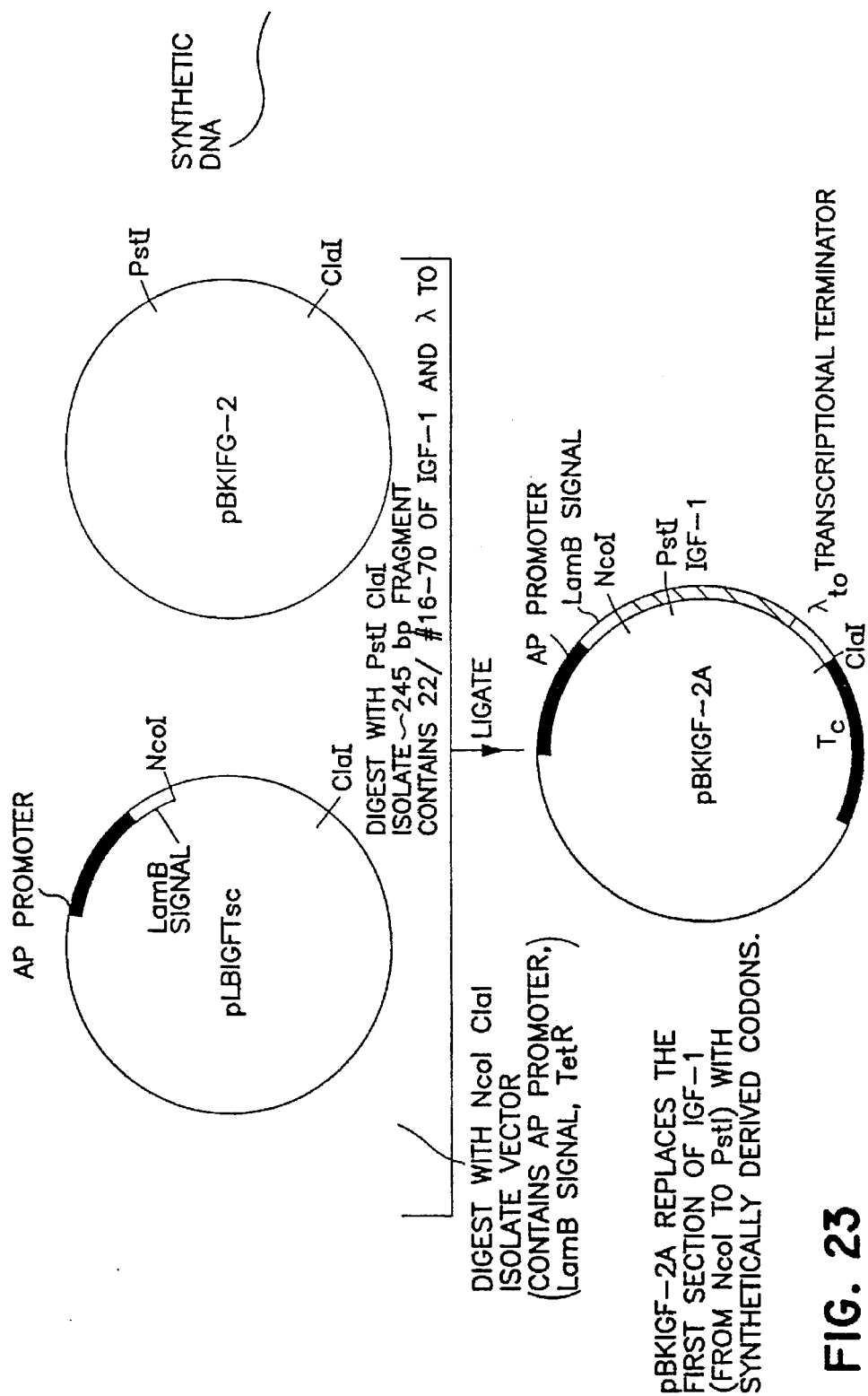
FIG. 23 depicts the construction of pBKIGF-2A, used to prepare pBKIGF-2B, from pLBIGFTsc, pBKIGF-2, and a piece of synthetic DNA (SEQ. ID NOS. 16 and 17).

The resulting plasmid was designated pBKIGF-2A. The construction is shown in FIG. 23.

Step 6: pLamBRan

This plasmid was prepared by digesting pLS33LamB with NcoI and BamHI and the vector fragment was isolated. pLS33LamB is a plasmid made from pBR322 into which was inserted the APpromoter, the lamb signal, and the IGF-I gene. BamHI cuts in the Tc portion of the plasmid and NcoI cuts at the 5' end of the IGF-I gene. The second fragment was generated by digesting pRANTES with BsaJI and BamHI and isolating the resultant ~200-bp fragment. The v. Results FIG. 26 presents the results of an experiment conducted in the modified 10-L fermentor. As can be seen from this figure, between 10 and 11 hours, the glucose feed rate (FIG. 26B) was being decreased under computer control to maintain the 30% $DO_2$ setpoint. This suggests that phosphate was being depleted and less glucose was being used for cell mass production. At approximately 11.5 hours, the glucose feed rate was placed under manual control. The glucose feed rate was then increased in increments until the $DO_2$ was driven to zero.

In this particular experiment, the DO$_2$ probe produced a reading of approximately 5% when the actual DO$_2$ concentration was zero. Although the shape of the initial DO$_2$ decline curve (FIG. 26A) suggested DO$_2$ instability, the result was not conclusive. Therefore, the glucose pump rate (GPR) was reduced to allow DO$_2$ recovery and was then increased in smaller increments. When another crash in DO$_2$ occurred at approximately 13 hours, the GPR was again decreased to allow recovery. At this point, an increase in GPR of less than 4% caused the characteristic profile of a slow DO$_2$ decline followed by a precipitous and much larger than predicted decline in the DO$_2$ concentration.

When the GPR was again lowered to allow recovery, a surprising series of events ensued. The DO$_2$ concentration in the fermentor began to cycle reproducibly with no outside stimulus. The irregularity observed in the pattern of the DO$_2$ cycles at 14.2 hr. was caused by a brief interruption in the glucose supply. Other than that single event, nothing was done to change the operational parameters of the fermentation. As can be seen, the cycles were quite consistent in amplitude and only varied in frequency, becoming farther apart until they stopped at 17.3 hours. Two additional series of nearly identical cycles were stimulated by decreasing the glucose feed rate at 20.25 and 22.2 hours.

These results demonstrate a dramatic instability in the DO$_2$ concentration in this modified 10-L fermentor. The general shape of the DO$_2$ decline part of the cycle is similar to that observed in the 1000-L fermentor. This suggests that the 10-L reactor is adequately duplicating the phenomena first observed in the larger fermentor. The speed and regularity of the cycles observed in the small reactor suggest a biological origin.

EXAMPLE IV

Generation of DO$_2$ Instabilities with Untransformed, Wild-type *E. Coli*

In the previous examples, the organism was being induced for product formation at the time of the DO$_2$ instabilities. The host organism was also relatively heavily mutated. To investigate the generality of the DO$_2$ instability phenomena, an untransformed and relatively unmutated organism was tested in the modified 10-L fermentor shown in FIG. 1. The organism was *E. coli* W3110tonA, the derivation of which is described above, designated 1A2. This organism is essentially a wild-type *E. coli* except for the defect in the tonA locus that avoids the formation of a cell-surface protein used for iron uptake and used as an attachment site by several bacteriophage. The organism was grown under the same conditions as described in Example III.

Figure 27A:
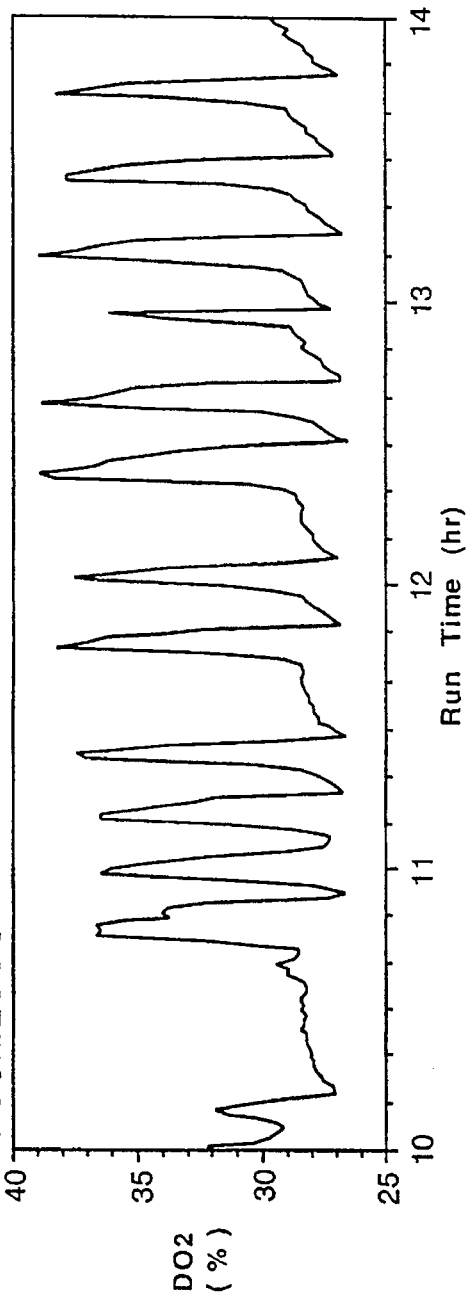
FIG. 27A, FIG. 27B and FIG. 27C illustrate % $DO_2$ (FIG. 27A), redox probe output (mV) (FIG. 27B), and glucose pump rate (ml/min) (FIG. 27C) versus time in the modified 10-L fermentor with an untransformed host W3110tonA, designated 1A2.
Figure 27B:
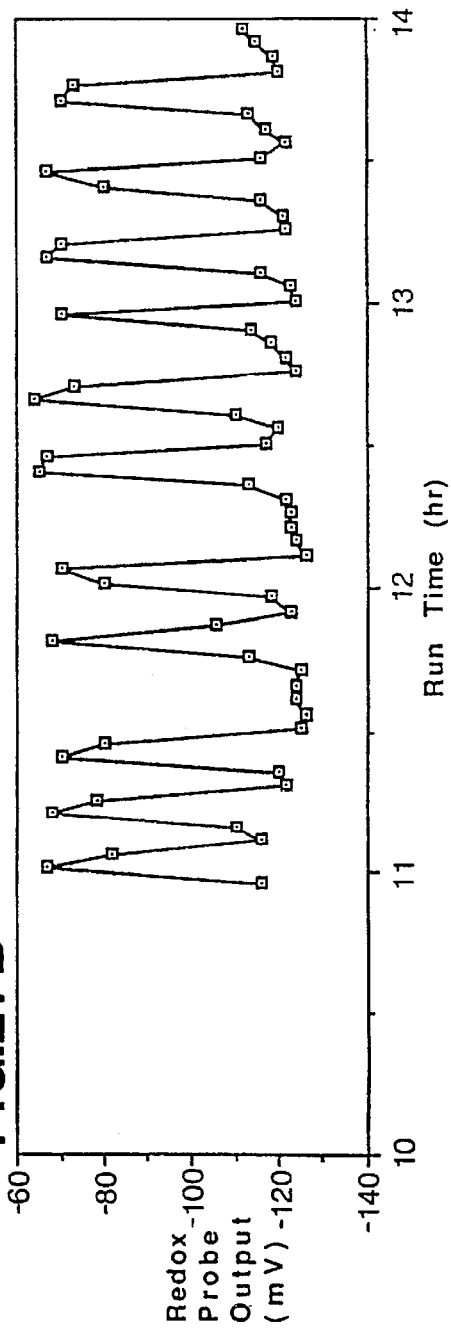
Figure 27C:
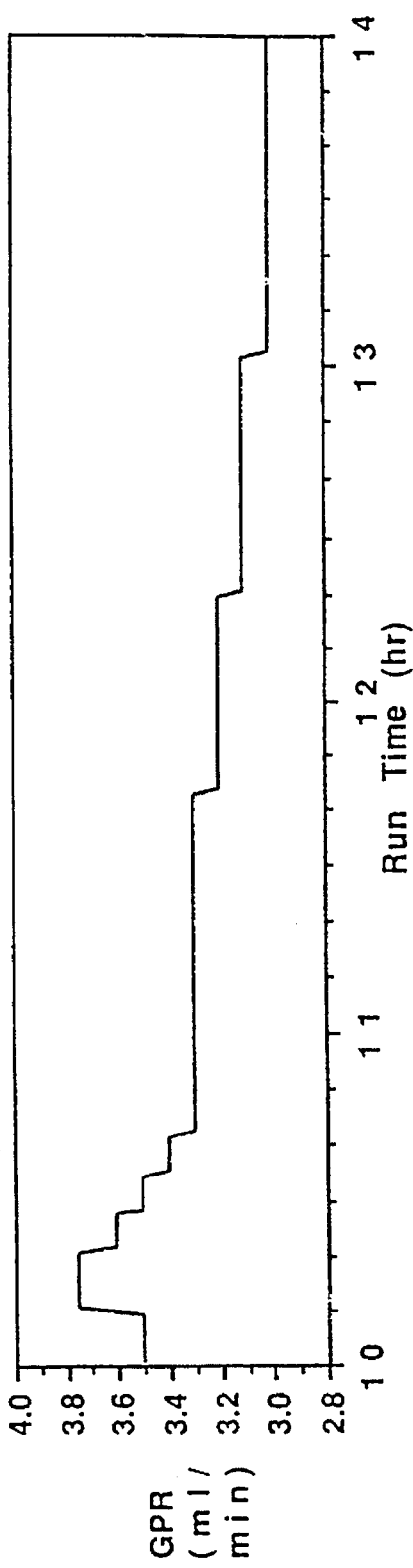

FIG. 27 illustrates the results of applying the same protocol to trigger DO$_2$ instabilities as described in Example III. In this fermentation, the DO$_2$ probe again produced a signal that overestimated the DO$_2$ concentration. A 27–29% signal represented a zero DO$_2$ concentration. Fortunately, after 11 hours, this experiment was also monitored by a redox probe and its output is plotted in FIG. 27B. Both signals indicate the generation of repetitive, regular oscillations in DO$_2$ concentration. Thus, the phenomena leading to DO$_2$ instability is not dependent on the presence of a plasmid, the formation of a heterologous product, or the several mutations used in the production host.

EXAMPLE V

Lack Of DO$_2$ Instability with Organisms Deficient in One Cytochrome Oxidase The previous examples suggest a biological origin for the DO$_2$ instabilities. The hypothesis being tested by this example is whether this phenomenon is related to switching between the two possible aerobic respiration chains, one mediated by cytochrome o oxidase and the other by cytochrome d oxidase. Thus, a deletion was made in each of the cytochrome oxidase genes by conventional P1 transduction into the W3110tonA host 1A2 to produce two new organisms, *E. coli* W3110tonAΔcyokan$^r$ and *E. coli* W3110tonAΔcydkan$^r$. The sources of the mutations were the organisms GV102 and GO103, respectively (Oden et al., *Gene*, 96:29–36 [1990]).

Figure 28A:
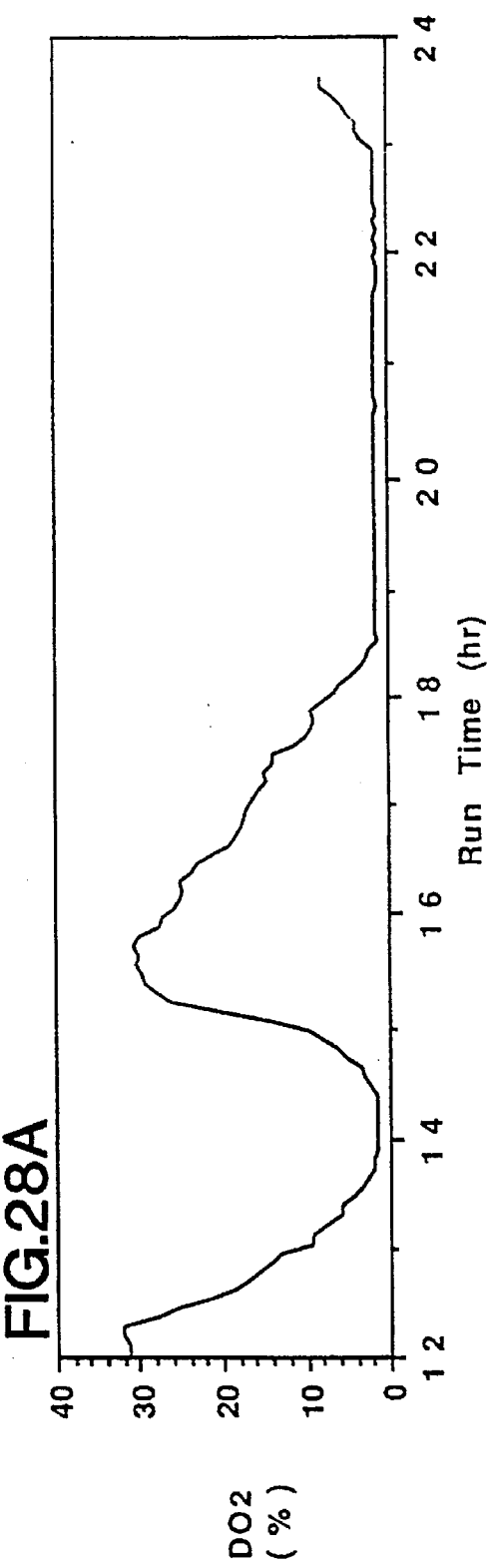
FIG. 28A, FIG. 28B and FIG. 28C illustrate % $DO_2$ (FIG. 28A), redox probe output (mV) (FIG. 28B), and glucose pump rate (ml/min) (FIG. 28C) versus time in the modified 10-L fermentor with an untransformed cytochrome o oxidase deletion mutant of the host W3110tonA.
Figure 28B:
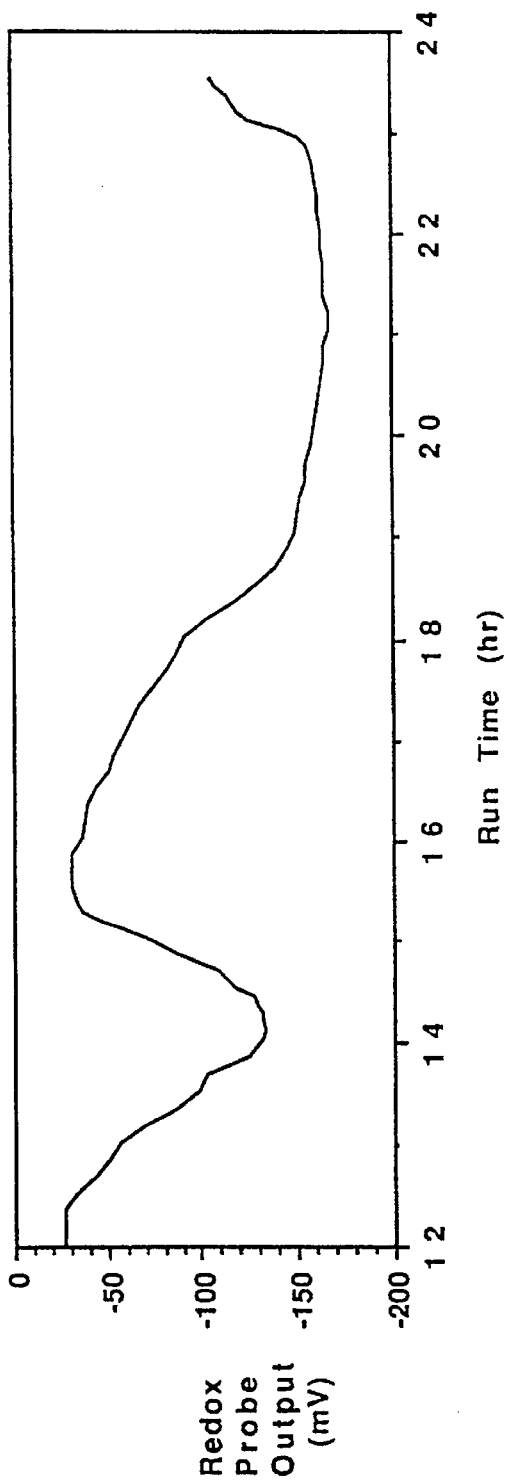
Figure 28C:
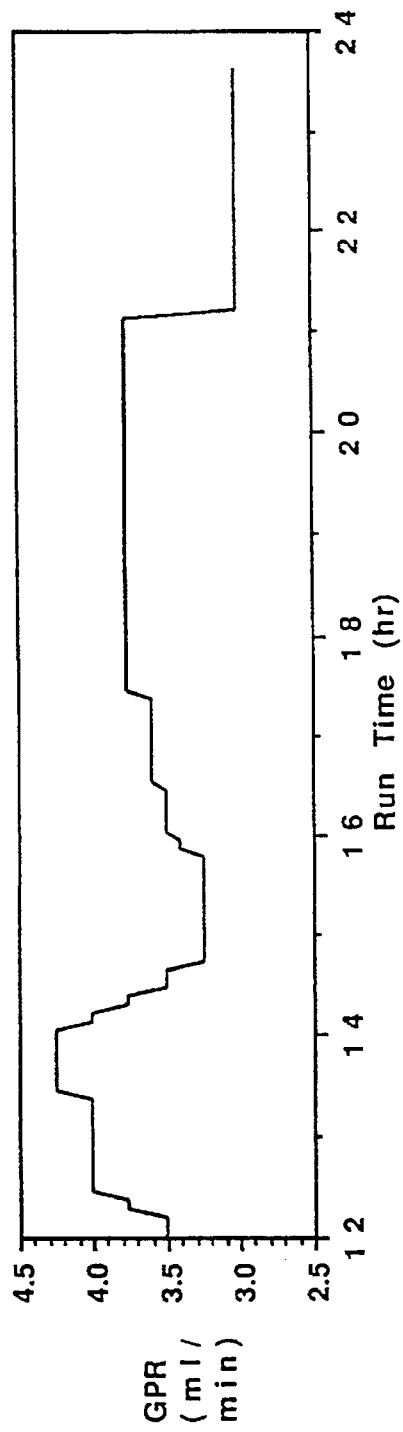

The organisms were grown in the modified 10-L fermentor as described in Example III. FIG. 28 presents the results of attempts to induce DO$_2$ instabilities with the cytochrome o oxidase deletion mutant. The time scale is 12 hours in this figure compared to the 4-hour time period required to show 12 DO$_2$ cycles in FIG. 27. The rapid approach to zero DO$_2$ characteristic of the DO$_2$ instabilities could not be induced. Both the approach to zero DO2 at 14 hours and the approach at 18.5 hours were slow with no hint of DO$_2$ instability. The redox probe output (FIG. 28B) told a similar story.

FIG. 29 presents the results obtained by following the same protocol with the cytochrome d oxidase deletion mutant. In this experiment, the lowest DO$_2$ probe reading was approximately 17%. That this corresponded to a depleted DO$_2$ condition was confirmed at 13.2 hours by briefly decreasing the agitation rate. No further decrease in the DO$_2$ reading was observed, although there was a response in the redox probe output. This example also illustrates the usefulness of the redox probe. In this experiment with the Δcyd mutated host, as with the Δcyo mutated host, there was no hint of DO$_2$ instability.

These results confirm the involvement of the two cytochrome oxidases in the DO$_2$ instabilities observed with the W3110tonA *E. coli* organism.

EXAMPLE VI

Lack of DO$_2$ Instability for Production Organisms Lacking One of the Cytochrome Oxidases It was next desired to determine if the same mutations would prevent DO$_2$ instability in a recombinant DNA production organism. The host organism 37D6 used in Example III was modified to produce three new host organisms.

In the first change, a non-kanamycin resistant degP deletion mutation was transduced into the host organism to make a kanamycin-sensitive host that would otherwise be isogenic. This mutation was effected using as the starting plasmid pKS16, which contains the periplasmic protease mutation, degP41kan$^r$, wherein a 2.3-kb PstIPstI fragment was deleted from the original 8-kb BamHI-BamHI fragment containing degP so that the gene is degP negative [Strauch et al., supra]. pKS16 was subjected to ultraviolet light mutagenesis as described in Jeffrey H. Miller, *Experiments in Molecular Genetics* (Cold Spring Harbor Laboratories, 1972), Experiment 13 on uv light mutagenesis, page 121, and the references cited therein. After mutagenesis, colonies were selected that lost kanamycin resistance. The selected-for non-kanamycin resistance mutation was moved into the chromosome of strain 37D6 by conventional transduction techniques to produce the kanamyc-insensitive host designated 40B4.

The kanamycin-linked Δcyo and Δcyd mutations were then transduced into host 40B4 to yield two new organisms, 39H8 and 39H9. These transductions were by standard methods. Strain 39H8 is isogenic to 40B4 except for having the cytochrome o mutation and being kanamycin resistant. Strain 39H9 is isogenic to 40B4 except for having the cytochrome d mutation and being kanamycin resistant. All three organisms were then transformed with the IGF-I production plasmid pBKIGF-2B.

FIG. 30 presents the results of testing for $DO_2$ instabilities with the transformed 40B4 production host in the modified 10-liter fermentor depicted in FIG. 1. Clearly, $DO_2$ instabilities were observed. Again the cycles were dramatic and regular. The relatively high $DO_2$'s experienced between 12.5 and 13.5 hours were the result of the computer control being accidentally reinstated. When the glucose feed rate was returned to manual control at the critical feed rate, the instabilities resumed their regular pattern.

In this experiment, the redox probe output was especially revealing. Even when the $DO_2$ probe reading was zero, the redox probe indicated changes in the redox potential of the medium. For example, at approximately 17 hours, the redox potential was not recovering. This suggested that the glucose feed rate had to be decreased for the $D_2$ cycles to resume. When the glucose feed rate was decreased, the cycles did indeed resume. In this experiment, it was impossible to maintain the redox probe output between approximately −50 and −100 mV. Without being limited to any one theory, this inability to maintain intermediate redox potentials would appear to be associated with the radical shifts in oxygen uptake rates.

Figure 31A:
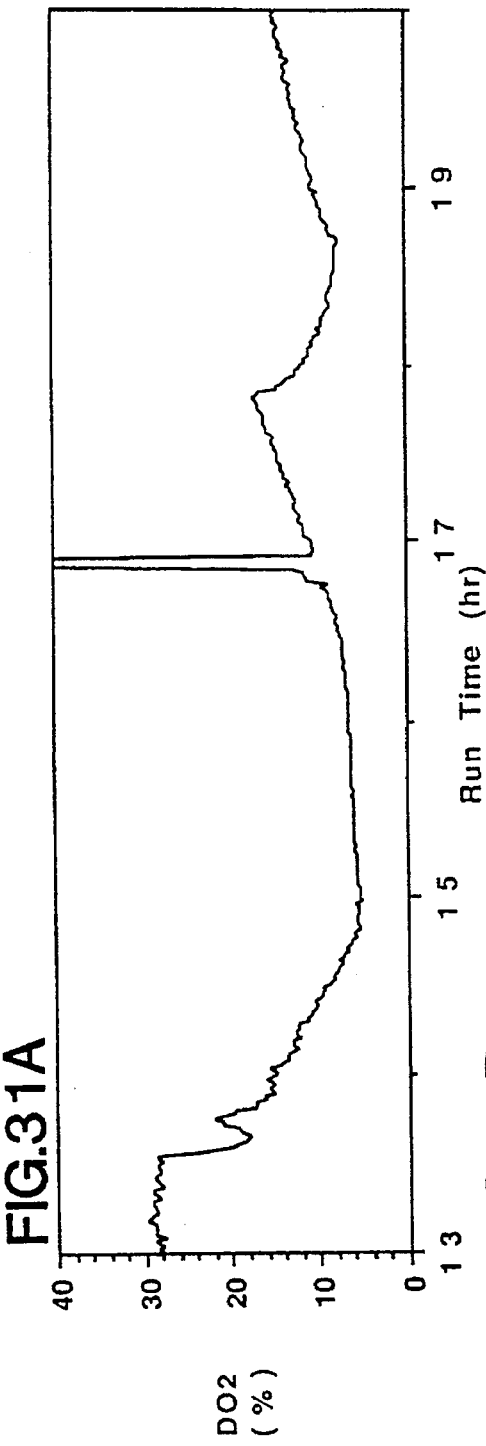
Figure 31B:
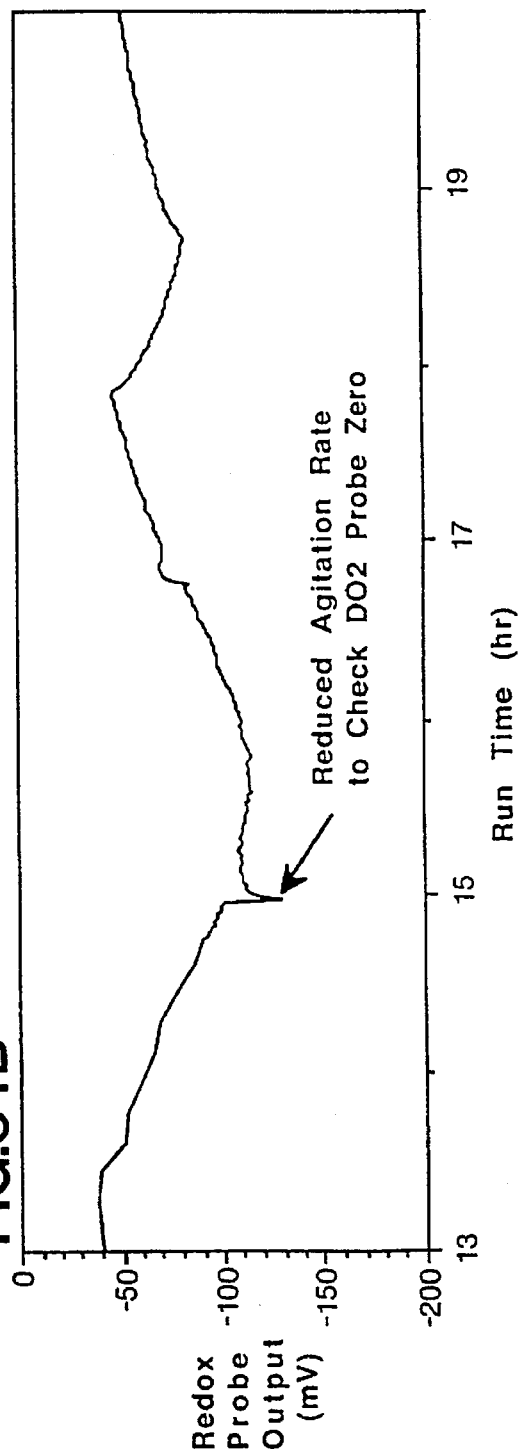

FIGS. 31 (cytochrome d oxidase deletion mutant 39H9) and FIG. 32 (cytochrome o oxidase deletion mutant 39H8) show the results of attempting to induce $DO_2$ instabilities with the cytochrome oxidase deletion mutants in the modified 10-liter fermentor depicted in FIG. 1. In neither case could $DO_2$ instabilities be generated. The one apparent discontinuity in the $DO_2$ profile in FIG. 31 was the result of a brief interruption in the glucose supply. For both mutated hosts, there was no apparent problem in controlling redox potentials that produced a probe output between −50 and −100 mV. Thus, as was seen for the untransformed wild-type host, the removal of one of the cytochrome oxidass genes prevented the $DO_2$ instabilities. These observations are consistent with the hypothesis that switching between the two aerobic respiration pathways is involved in the $DO_2$ instability.

EXAMPLE VII

Evaluation of IGF-I Production by the Cytochrome o Oxidase Deletion Mutant

To evaluate the suitability of the cytochrome-oxidase-mutated hosts for recombinant DNA protein production, the cytochrome o oxidase mutant was examined. Since the cytochrome o oxidase is the one normally used for vigorous aerobic respiration, it was anticipated that the mutant strain with the cytochrome d oxidase deletion would be the healthier host. However, this was not observed. It grew more slowly and was not able to maintain high respiration rates for as long a duration as the cytochrome o oxidass mutant. Thus, the cytochrome o oxidase deletion mutant was evaluated for its ability to express and accumulate human IGF-I.

Figure 33:
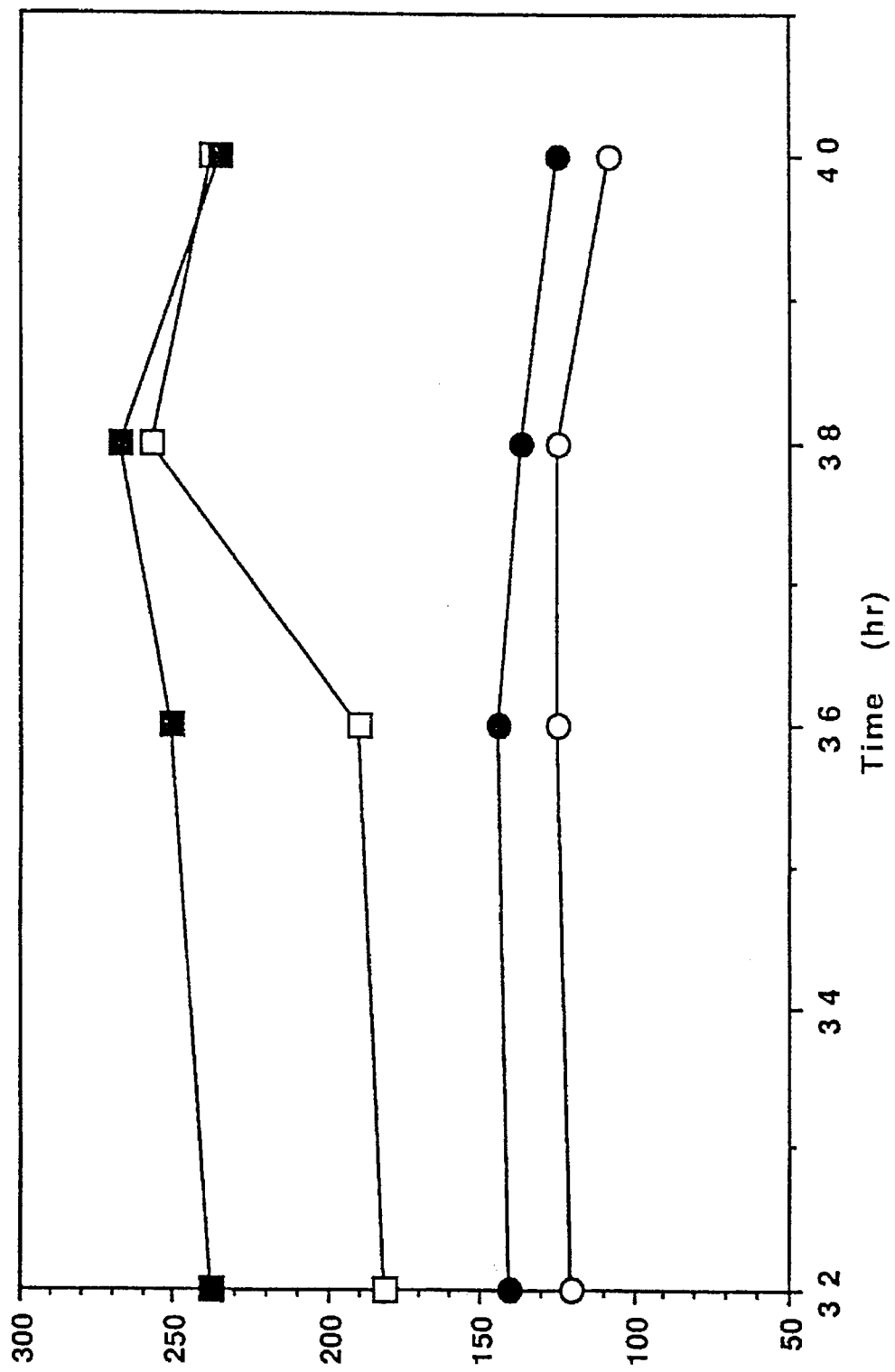
FIG. 33 illustrates 10-L fermentation results comparing growth (cell density at A550, circles) and total IGF-I production/10 (mg/L, squares) for a cytochrome o oxidase deletion mutant of strain 40B4 (open squares or circles) and strain 40B4 as an isogenic control (solid squares or circles), both the mutant and control being transformed with pBKIGF-2B.

FIG. 33 shows the total IGF-I accumulation and the cell density observed for comparison fermentations of the cytochrome o oxidase mutant strain 39H8 transformed with pBKIGF-2B and of control strain 40B4 transformed with pBKIGF-2B, conducted as described in Example I except for being performed in an unmodified 10-L fermentor. All three Rushton impellers were used as well as the full concentrations of medium salts. The complex nitrogen feed described in Example III was fed at a rate of 0.2 ml/min.

Although the final cell density was slightly lower for the mutant than for the control, the final volumetric yield of IGF-I was identical in the normal 10-liter fermentor. This demonstrates the suitability of cytochrome o oxidase hosts for recombinant protein production. It is anticipated that in larger-scale fermentors such as fermentors with about 1000-, 10,000-, or 100,000-liter capacity, the IGF-I yield would be improved for the mutant versus the control, and/or the process would be more in conformance with FDA requirements because it would not be accompanied by dramatic fluctuations in $DO_2$ concentration during the course of fermentation.

Additionally, it is anticipated that other mutations in the cytochrome o or d oxidase respiration pathways or mutations in other respiration pathways than the oxidase pathways will also allow normal production of recombinant DNA products without having the propensity to produce $DO_2$ instabilities.

---

What is claimed is:

1. A small scale fermentation apparatus that reproduces oxygen instability of large scale fermentation, comprising:

a vessel having a small volumetric capacity adapted to hold a liquid culture medium and microorganisms to be cultured therein;

a vertical shaft disposed in the center of the vessel;

two impellers connected to the vertical shaft, a top impeller and a bottom impeller, the top impeller located a distance above the bottom impeller and located sufficiently below the surface level of the liquid culture medium to provide inadequately mixed dissolved oxygen in the liquid culture medium;

a gas inlet disposed at the bottom of the vessel;

a probe for dissolved oxygen connected to the vessel in close proximity to the bottom impeller:

a redox probe connected to the vessel in close proximity to the bottom impeller; and a liquid inlet disposed at the top of the vessel through which a feed rate can be controlled to facilitate production of dissolved oxygen instabilities.

2. The fermentation apparatus of claim 1 wherein the vessel has an approximately 10-liter capacity.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 55 bases
( B ) TYPE: nucleic acid
( C ) STRANDEDNESS: single
( D ) TOPOLOGY: linear ( x i ) SEQUENCE DESCRIPTION: SEQ ID NO:1:

GGTCCCGAAA CTCTGTGCGG TGCTGAACTG GTTGACGCTC TGCAGTTTGT 50

TTGCG 55

( 2 ) INFORMATION FOR SEQ ID NO:2:

( i ) SEQUENCE CHARACTERISTICS:
      ( A ) LENGTH: 64 bases
      ( B ) TYPE: nucleic acid
      ( C ) STRANDEDNESS: single
      ( D ) TOPOLOGY: linear ( x i ) SEQUENCE DESCRIPTION: SEQ ID NO:2:

ACGTCCAGGG CTTTGAGACA CGCCACGACT TGACCAACTG CGAGACGTCA 50

AACAAACGCC ACTG 64

( 2 ) INFORMATION FOR SEQ ID NO:3:

( i ) SEQUENCE CHARACTERISTICS:
      ( A ) LENGTH: 84 bases
      ( B ) TYPE: nucleic acid
      ( C ) STRANDEDNESS: single
      ( D ) TOPOLOGY: linear ( x i ) SEQUENCE DESCRIPTION: SEQ ID NO:3:

CTAGAATTAT GATGATTACT CTGCGCAAAC TTCCTCTGGC GGTTGCCGTC 50

GCAGCGGGCG TAATGTCTGC TCAGGCCATG GCCA 84

( 2 ) INFORMATION FOR SEQ ID NO:4:

( i ) SEQUENCE CHARACTERISTICS:
      ( A ) LENGTH: 84 bases
      ( B ) TYPE: nucleic acid
      ( C ) STRANDEDNESS: single
      ( D ) TOPOLOGY: linear ( x i ) SEQUENCE DESCRIPTION: SEQ ID NO:4:

TTAATACTAC TAATGAGACG CGTTTGAAGG AGACCGCCAA CGGCAGCGTC 50

GCCCGCATTA CAGACGAGTC CGGTACCGGT CTAG 84

( 2 ) INFORMATION FOR SEQ ID NO:5:

( i ) SEQUENCE CHARACTERISTICS:
      ( A ) LENGTH: 59 bases
      ( B ) TYPE: nucleic acid
      ( C ) STRANDEDNESS: single
      ( D ) TOPOLOGY: linear ( x i ) SEQUENCE DESCRIPTION: SEQ ID NO:5:

GGCCGGTCCC GAAACTCTGT GCGGTGCTGA ACTGGTTGAC GCTCTGCAGT 50

TTGTTTGCG 59

( 2 ) INFORMATION FOR SEQ ID NO:6:

( i ) SEQUENCE CHARACTERISTICS:
      ( A ) LENGTH: 60 bases
      ( B ) TYPE: nucleic acid
      ( C ) STRANDEDNESS: single
      ( D ) TOPOLOGY: linear ( x i ) SEQUENCE DESCRIPTION: SEQ ID NO:6:

CCAGGGCTTT GAGACACGCC ACGACTTGAC CAACTGCGAG ACGTCAAACA 50

AACGCCACTG 60

( 2 ) INFORMATION FOR SEQ ID NO:7:

( i ) SEQUENCE CHARACTERISTICS:
      ( A ) LENGTH: 50 bases (B) TYPE: nucleic acid
(C) STRANDEDNESS: single
(D) TOPOLOGY: linear (xi) SEQUENCE DESCRIPTION: SEQ ID NO:7:

```
GGCCACTCTG TGCGGTGCTG AACTGGTTGA CGCTCTGCAG TTTGTTTGCG      50
```

(2) INFORMATION FOR SEQ ID NO:8:

(i) SEQUENCE CHARACTERISTICS:
(A) LENGTH: 51 bases
(B) TYPE: nucleic acid
(C) STRANDEDNESS: single
(D) TOPOLOGY: linear (xi) SEQUENCE DESCRIPTION: SEQ ID NO:8:

```
TGAGACACGC CACGACTTGA CCAACTGCGA GACGTCAAAC AAACGCCACT      50
G                                                           51
```

(2) INFORMATION FOR SEQ ID NO:9:

(i) SEQUENCE CHARACTERISTICS:
(A) LENGTH: 39 bases
(B) TYPE: nucleic acid
(C) STRANDEDNESS: single
(D) TOPOLOGY: linear (xi) SEQUENCE DESCRIPTION: SEQ ID NO:9:

```
CCTAACGCTC GGTTGCCGCC GGGCGTTTTT TATTGTTAA                  39
```

(2) INFORMATION FOR SEQ ID NO:10:

(i) SEQUENCE CHARACTERISTICS:
(A) LENGTH: 39 bases
(B) TYPE: nucleic acid
(C) STRANDEDNESS: single
(D) TOPOLOGY: linear (xi) SEQUENCE DESCRIPTION: SEQ ID NO:10:

```
GGATTGCGAG CCAACGGCGG CCCGCAAAAA ATAACAATT                  39
```

(2) INFORMATION FOR SEQ ID NO:11:

(i) SEQUENCE CHARACTERISTICS:
(A) LENGTH: 757 bases
(B) TYPE: nucleic acid
(C) STRANDEDNESS: single
(D) TOPOLOGY: linear (xi) SEQUENCE DESCRIPTION: SEQ ID NO:11:

```
GAATTCAACT TCTCCATACT TTGGATAAGG AAATACAGAC ATGAAAAATC      50
TCATTGCTGA GTTGTTATTT AAGCTTGCCC AAAAAGAAGA AGAGTCGAAT     100
GAACTGTGTG CGCAGGTAGA AGCTTTGGAG ATTATCGTCA CTGCAATGCT     150
TCGCAATATG GCGCAAAATG ACCAACAGCG GTTGATTGAT CAGGTAGAGG     200
GGGCGCTGTA CGAGGTAAAG CCCGATGCCA GCATTCCTGA CGACGATACG     250
GAGCTGCTGC GCGATTACGT AAAGAAGTTA TTGAAGCATC CTCGTCAGTA     300
AAAAGTTAAT CTTTTCAACA GCTGTCATAA AGTTGTCACG GCCGAGACTT     350
ATAGTCGCTT TGTTTTTATT TTTTAATGTA TTTGTAACTA GTACGCAAGT     400
TCACGTAAAA AGGGTATCTA GAATTATGAT GATTACTCTG CGCAAACTTC     450
CTCTGGCGGT TGCCGTCGCA GCGGGCGTAA TGTCTGCTCA GGCCATGGCC     500
```

```
GGTCCCGAAA  CTCTGTGCGG  TGCTGAACTG  GTTGACGCTC  TGCAGTTTGT   550

TTGCGGTGAC  CGTGGTTTTT  ATTTTAACAA  ACCCACTGGT  TATGGTTCTT   600

CTTCTCGTCG  TGCTCCCCAG  ACTGGTATTG  TTGACGAATG  CTGCTTTCGT   650

TCTTGCGACC  TGCGTCGTCT  GGAAATGTAT  TGCGCTCCCC  TGAAACCCGC   700

TAAATCTGCT  TAGAAGCTCC  TAACGCTCGG  TTGCCGCCGG  GCGTTTTTA    750

TTGTTAA 757
```

( 2 ) INFORMATION FOR SEQ ID NO:12:

( i ) SEQUENCE CHARACTERISTICS:
        ( A ) LENGTH: 94 amino acids
        ( B ) TYPE: amino acid
        ( D ) TOPOLOGY: linear ( x i ) SEQUENCE DESCRIPTION: SEQ ID NO:12:

```
Met  Ile  Thr  Leu  Arg  Lys  Leu  Pro  Leu  Ala  Val  Ala  Val  Ala  Ala
 1              5                        10                       15

Gly  Val  Met  Ser  Ala  Gln  Ala  Met  Ala  Gly  Pro  Glu  Thr  Leu  Cys
                    20                       25                       30

Gly  Ala  Glu  Leu  Val  Asp  Ala  Leu  Gln  Phe  Val  Cys  Gly  Asp  Arg
                    35                       40                       45

Gly  Phe  Tyr  Phe  Asn  Lys  Pro  Thr  Gly  Tyr  Gly  Ser  Ser  Ser  Arg
                    50                       55                       60

Arg  Ala  Pro  Gln  Thr  Gly  Ile  Val  Asp  Glu  Cys  Cys  Phe  Arg  Ser
                    65                       70                       75

Cys  Asp  Leu  Arg  Arg  Leu  Glu  Met  Tyr  Cys  Ala  Pro  Leu  Lys  Pro
                    80                       85                       90

Ala  Lys  Ser  Ala
                94
```

( 2 ) INFORMATION FOR SEQ ID NO:13:

( i ) SEQUENCE CHARACTERISTICS:
        ( A ) LENGTH: 485 bases
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
GAATTCATGA  GATTTCCTTC  AATTTTTACT  GCAGTTTTAT  TCGCAGCATC    50

CTCCGCATTA  GCTGCTCCAG  TCAACACTAC  AACAGAAGAT  GAAACGGCAC   100

AAATTCCGGC  TGAAGCTGTC  ATCGGTTACT  TAGATTTAGA  AGGGGATTTC   150

GATGTTGCTG  TTTTGCCATT  TTCCAACAGC  ACAAATAACG  GGTTATTGTT   200

TATAAATACT  ACTATTGCCA  GCATTGCTGC  TAAAGAAGAA  GGGGTATCTT   250

TGGATAAAAG  AGGTCCGGAA  ACTCTGTGCG  GCGCTGAGCT  GGTTGACGCT   300

CTGCAGTTCG  TATGTGGTGA  TCGAGGCTTC  TACTTCAACA  AACCGACTGG   350

GTACGGATCC  TCCTCTCGTC  GTGCTCCGCA  AACCGGCATC  GTTGATGAAT   400

GCTGTTTTCG  GTCCTGTGAC  CTTCGCCGTC  TGGAAATGTA  CTGCGCTCCG   450

CTGAAACCGG  CTAAGTCTGC  ATAGTCGACG  AATTC        485
```

( 2 ) INFORMATION FOR SEQ ID NO:14:

( i ) SEQUENCE CHARACTERISTICS:
        ( A ) LENGTH: 30 bases
        ( B ) TYPE: nucleic acid ( C ) STRANDEDNESS: single
( D ) TOPOLOGY: linear ( x i ) SEQUENCE DESCRIPTION: SEQ ID NO:14:

CATGGCCGGT CCGGAAACTC TGTGCGGCGC   30

( 2 ) INFORMATION FOR SEQ ID NO:15:

( i ) SEQUENCE CHARACTERISTICS:
( A ) LENGTH: 22 bases
( B ) TYPE: nucleic acid
( C ) STRANDEDNESS: single
( D ) TOPOLOGY: linear ( x i ) SEQUENCE DESCRIPTION: SEQ ID NO:15:

CGGCCAGGCC TTTGAGACAC GC   22

( 2 ) INFORMATION FOR SEQ ID NO:16:

( i ) SEQUENCE CHARACTERISTICS:
( A ) LENGTH: 51 bases
( B ) TYPE: nucleic acid
( C ) STRANDEDNESS: single
( D ) TOPOLOGY: linear ( x i ) SEQUENCE DESCRIPTION: SEQ ID NO:16:

CATGGCCGGT CCCGAAACTC TGTGCGGTGC TGAACTGGTT GACGCTCTGC   50

A   51

( 2 ) INFORMATION FOR SEQ ID NO:17:

( i ) SEQUENCE CHARACTERISTICS:
( A ) LENGTH: 43 bases
( B ) TYPE: nucleic acid
( C ) STRANDEDNESS: single
( D ) TOPOLOGY: linear ( x i ) SEQUENCE DESCRIPTION: SEQ ID NO:17:

CGGCCAGGGC TTTGAGACAC GCCACGACTT GACCAACTGC GAG   43

( 2 ) INFORMATION FOR SEQ ID NO:18:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( x i ) SEQUENCE DESCRIPTION: SEQ ID NO:18:

CATGGCCTCC CCATATTC   18

( 2 ) INFORMATION FOR SEQ ID NO:19:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( x i ) SEQUENCE DESCRIPTION: SEQ ID NO:19:

CGGAGGGGTA TAAGGAGC   18

( 2 ) INFORMATION FOR SEQ ID NO:20:

( i ) SEQUENCE CHARACTERISTICS:
( A ) LENGTH: 67 bases
( B ) TYPE: nucleic acid ( C ) STRANDEDNESS: single
( D ) TOPOLOGY: linear ( x i ) SEQUENCE DESCRIPTION: SEQ ID NO:20:

TCGTCGTGCT CCCCAGACTG GTATTGTTGA CGAATGCTGC TTTCGTTCTT 50

GCGACCTGCG TCGTCTG 67

( 2 ) INFORMATION FOR SEQ ID NO:21:

( i ) SEQUENCE CHARACTERISTICS:
( A ) LENGTH: 70 bases
( B ) TYPE: nucleic acid
( C ) STRANDEDNESS: single
( D ) TOPOLOGY: linear ( x i ) SEQUENCE DESCRIPTION: SEQ ID NO:21:

AGAACGCTGG ACGCAGCAGA CCTTTACATA ACGCGAGGGG ACTTTGGGCG 50

ATTTAGACGA ATCTTCGAGG 70